(12) United States Patent
Zheng et al.

(10) Patent No.: US 12,393,009 B2
(45) Date of Patent: Aug. 19, 2025

(54) VIBRATION DAMPENING STRUCTURE, DETECTION SYSTEM AND SEQUENCING SYSTEM

(71) Applicant: GeneMind Biosciences Company Limited, Guangdong (CN)

(72) Inventors: Jiao Zheng, Guangdong (CN); Zefei Jiang, Guangdong (CN); Zhiliang Zhou, Guangdong (CN); Guangming Wang, Guangdong (CN); Songzhen Zhang, Guangdong (CN)

(73) Assignee: Genemind Biosciences Company Limited, Shenzen (CN)

(*) Notice: Subject to any disclaimer, the term of this patent is extended or adjusted under 35 U.S.C. 154(b) by 820 days.

(21) Appl. No.: 17/763,164

(22) PCT Filed: Jul. 14, 2020

(86) PCT No.: PCT/CN2020/101908
§ 371 (c)(1),
(2) Date: Mar. 23, 2022

(87) PCT Pub. No.: WO2021/057200
PCT Pub. Date: Apr. 1, 2021

(65) Prior Publication Data
US 2022/0373780 A1 Nov. 24, 2022

(30) Foreign Application Priority Data
Sep. 24, 2019 (CN) .......................... 201910907555.7

(51) Int. Cl.
*G01N 3/00* (2006.01)
*C12Q 1/6869* (2018.01)
(Continued)

(52) U.S. Cl.
CPC ......... *G02B 21/362* (2013.01); *C12Q 1/6869* (2013.01); *G02B 21/06* (2013.01); *G02B 21/18* (2013.01); *G02B 27/646* (2013.01)

(58) Field of Classification Search
None
See application file for complete search history.

(56) References Cited

U.S. PATENT DOCUMENTS

2007/0273877 A1  11/2007  Kawano et al.
2009/0280559 A1  11/2009  McCarthy
(Continued)

FOREIGN PATENT DOCUMENTS

CN  101970876 A  2/2011
CN  204356321 U  5/2015
(Continued)

OTHER PUBLICATIONS

EPO Examination Report, dated May 2, 2025, for European Patent Application No. 20 868 405.0-1001. (15 pages).
(Continued)

*Primary Examiner* — Jyoti Nagpaul
(74) *Attorney, Agent, or Firm* — Seed Intellectual Property Law Group LLP

(57) ABSTRACT

A vibration damping structure (60), a detection system and a sequencing system. The vibration damping structure (60) is used in the detection system. The vibration damping structure (60) comprises a main body (62) and a support body (64), the main body (62) is connected to the detection system by means of the support body (64), the main body (62) comprises an imaging module (10), an upper layer structure (66), a lower layer structure (68) and an intermediate structure (70), the imaging module (10) is mounted on the upper layer structure (66), the lower layer structure (68) bears the upper layer structure (66) by means of the intermediate structure (70), and the natural frequency of the main body (62) is greater than or equal to $\sqrt{2}$ times the internal excitation frequency.

20 Claims, 24 Drawing Sheets

(51) Int. Cl.
    *G02B 21/06*     (2006.01)
    *G02B 21/18*     (2006.01)
    *G02B 21/36*     (2006.01)
    *G02B 27/64*     (2006.01)

(56) References Cited

U.S. PATENT DOCUMENTS

| | | |
|---|---|---|
| 2012/0182412 A1 | 7/2012 | He |
| 2013/0239690 A1* | 9/2013 | Tadano ............ G01R 33/56358 73/644 |
| 2016/0223461 A1 | 8/2016 | Jaffe et al. |

FOREIGN PATENT DOCUMENTS

| | | |
|---|---|---|
| CN | 205317635 U | 6/2016 |
| CN | 205368376 U | 7/2016 |
| CN | 106525856 A | 3/2017 |
| CN | 109799595 A | 5/2019 |
| CN | 109971629 A | 7/2019 |
| CN | 209052715 U | 7/2019 |
| JP | 2012095582 A | 5/2012 |
| KR | 20190012950 A | 2/2019 |

OTHER PUBLICATIONS

Translation of International Search Report of International Application PCT/CN2020/101908, mailed on Oct. 15, 2020. (2 pages).

* cited by examiner

Spot distribution from FoV 1   Spot distribution from FoV 2   Spot distribution from FoV 3

Image plane: 0.000 mm

Image plane: 3.250 mm

Image plane: 6.500 mm

VIBRATION DAMPENING STRUCTURE, DETECTION SYSTEM AND SEQUENCING SYSTEM

CROSS REFERENCE TO RELATED APPLICATIONS

The present application claims priority and benefit to Chinese patent application No. 201910907555.7 filed with China National Intellectual Property Administration on Sep. 24, 2019, which is incorporated herein by reference in its entirety.

TECHNICAL FIELD

The present application relates to the field of machinery, and in particular to a vibration damping structure, a detection system and a sequencing system.

BACKGROUND

Mechanical vibration is a ubiquitous natural physical phenomenon, and it can be generated by internal interaction inside a mechanism and by external excitation transmission as well. In most cases, mechanical vibration poses negative effect and even causes safety failures in severe cases.

A detection system comprising an imaging module realizes detection based on image acquisition and image data analysis, and is generally sensitive to vibration. In designing and testing a detection system, including designing and testing hardware component module and system integration, vibration damping, vibration isolation design and the like generally need to be considered and vibration evaluation needs to be performed, so that the designed component module and/or system can effectively isolate and/or attenuate interference of external and internal vibration factors.

In a sequencing system/sequencing platform for detecting target nucleic acid molecules in a reaction device based on an optical imaging system, the sequencing system comprises an imaging module. The imaging module is used for photographing the nucleic acid molecules in the reaction device (such as a flowcell) during sequencing, and the resulting images are analyzed to obtain a sequencing result.

Generally, the imaging module and/or sequencing system is very sensitive to vibration since the imaging module captures signals from a single nucleic acid molecule or a cluster of molecules. During imaging/sequencing, it is necessary to effectively isolate and attenuate the interference of external and/or internal vibration factors of the imaging module or the sequencing system, so as to ensure that the imaging/sequencing can stably obtain clear images of nucleic acid molecules, and thus guarantee the accuracy and reliability of the sequencing result.

Therefore, there is a need to provide a vibration damping structure, a detection system and/or a sequencing system.

SUMMARY

Embodiments of the present application provide a vibration damping structure, a detection system and a sequencing system.

The present application provides a vibration damping structure used in a detection system, wherein the vibration damping structure comprises a body and a support; the body is connected with the detection system through the support, and the body comprises an imaging module, an upper structure, a lower structure and an intermediate structure, wherein the imaging module is mounted on the upper structure, the lower structure carriers the upper structure through the intermediate structure, and a natural frequency of the body is greater than or equal to $\sqrt{2}$ times an internal excitation frequency.

In the vibration damping structure described above, considering that two-dimensional movement in the X/Y direction is involved for the body, an upper-lower double-layer structure is adopted for the body, which can effectively suppress the vibration of the whole platform, and meanwhile, a natural frequency of the body is greater than or equal to $\sqrt{2}$ times an internal excitation frequency, which can further effectively suppress internal excitation and thereby improve vibration damping effect of the whole vibration damping structure.

The present application provides a detection system comprising the vibration damping structure of any of the above embodiments.

The present application provides a sequencing system comprising the vibration damping structure of any of the above embodiments.

In the detection system and the sequencing system described above, considering that two-dimensional movement in the X/Y direction is involved for the body, an upper-lower double-layer structure is adopted for the body, which can effectively suppress the vibration of the whole platform, and meanwhile, a natural frequency of the body is greater than or equal to $\sqrt{2}$ times an internal excitation frequency, which can further effectively suppress internal excitation and thereby improve vibration damping effect of the whole vibration damping structure.

The additional aspects and advantages of the embodiments of the present application will be partially set forth in the following description, and will partially become apparent from the following description or be appreciated by practice of the embodiments of the present application.

BRIEF DESCRIPTION OF THE DRAWINGS

The aforementioned and/or additional aspects and advantages of the embodiments of the present application will become apparent and easily understood from the description of the embodiments in reference to the following drawings, among which.

DETAILED DESCRIPTION

Figure 1:
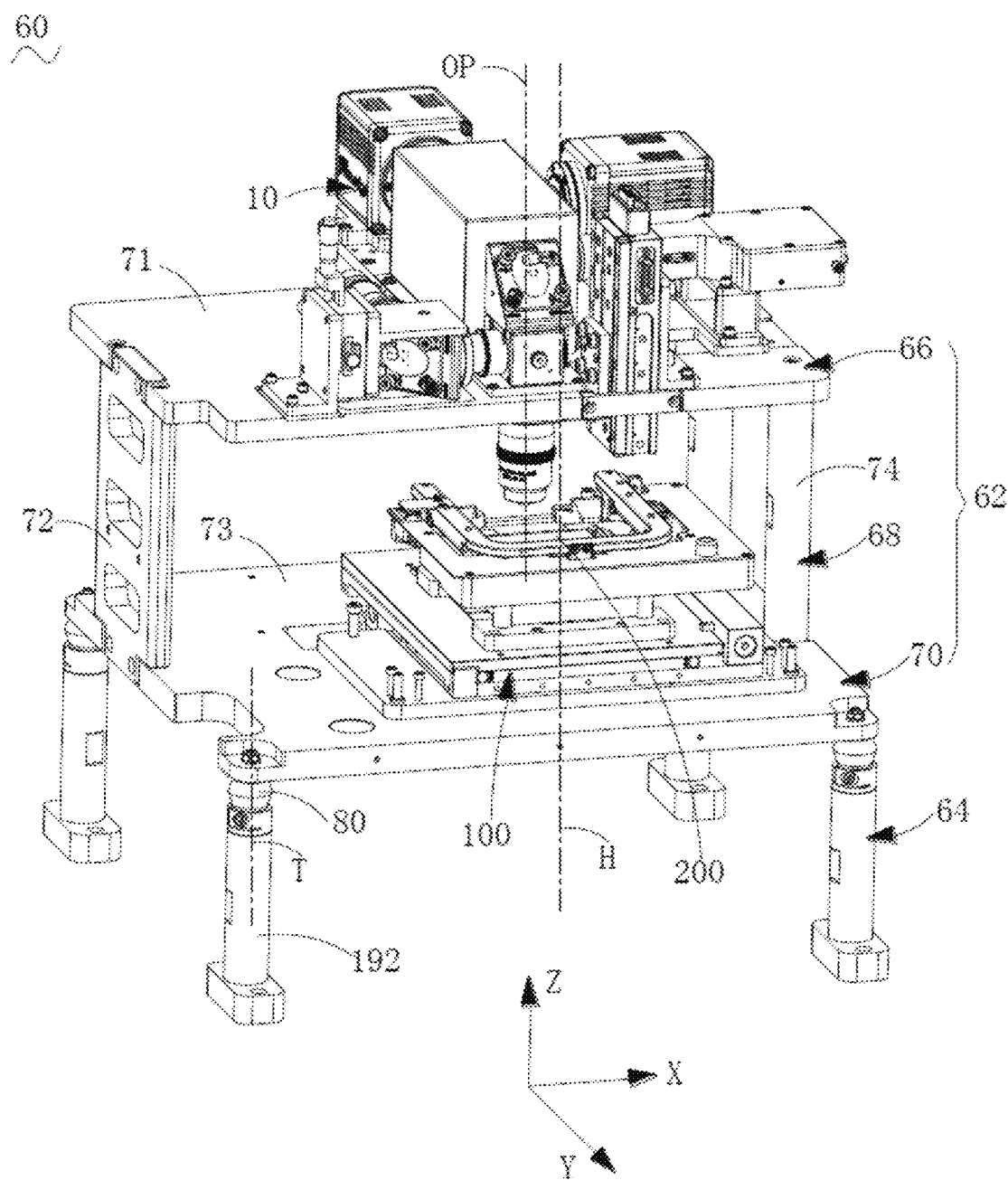
FIG. 1 is a structural schematic view of a vibration damping structure according to an embodiment of the present application.

The embodiments of the present application are described in detail below, and the examples of the embodiments are shown in the accompanying drawings, throughout which identical or similar reference numerals represent identical or similar elements or elements having identical or similar functions. The embodiments described below by reference to the accompanying drawings are exemplary and are merely intended to illustrate the present application, but should not be construed as limiting the present application.

In the description of the present application, it should be understood that the terms "first" and "second" are used for description purpose only rather than construed as indicating or implying relative importance or implicitly indicating the number or sequence of indicated technical features. Therefore, features defined with "first", "second", etc., may explicitly or implicitly include one or more of the features. In the description of the present application, unless otherwise specifically defined, "a plurality of" means two or more than two.

In the description of the present application, it should be noted that unless otherwise clearly specified and defined, "connect" should be comprehended in its broad sense. For example, "connect" may be "fixedly connect", "detachably connect" or "integrally connect"; "mechanically connect", "electrically connect" or "communicate with each other"; or "directly interconnect", "indirectly interconnect through an intermediate", "the communication between the interiors of two elements" or "the interaction between two elements". For those of ordinary skill in the art, the specific meanings of the aforementioned terms in the present application can be understood according to specific conditions.

The following disclosure provides many different embodiments or examples for implementing different structures of the present application. To simplify the disclosure of the present application, components and settings of specific examples are described below. In addition, the present application may repeat reference numbers and/or reference letters in different examples. Such repetition is intended for simplicity and clarity rather than for indicating the relationship between various embodiments and/or settings discussed.

"Sequence determination" used in the embodiments of the present application refers to nucleic acid sequence determination, including DNA sequencing and/or RNA sequencing, and/or including long fragment sequencing and/or short fragment sequencing. The "sequence determination" refers to sequencing. Generally, in nucleic acid sequence determination, a template can be extended by one base through one cycle of sequencing, wherein the base is selected from at least one of A, T, C, G and U. In sequencing by synthesis and/or sequencing by ligation, the sequencing includes extension (base extension), information collection (photographing/image acquisition) and radical cleavage. The substrate for the sequencing is a "nucleotide analogue", also called a terminator. It is an analogue of A, T, C, G and/or U, and is capable of pairing with a specific type of base following the complementary base pairing rule and terminating the binding of the next nucleotide analogue/substrate to the template strand as well.

Referring to FIGS. 1-4, a vibration damping structure 60 provided in an embodiment of the present application is used in a detection system. The vibration damping structure 60 comprises a body 62 and a support 64. The body 62 is connected with the detection system through the support 64, and the body 62 comprises an imaging module 10, an upper structure 66, a lower structure 68 and an intermediate structure 70. The imaging module 10 is mounted on the upper structure 66, the lower structure 68 carries the upper structure 66 through the intermediate structure 70, and a natural frequency of the body 62 is greater than or equal to V times an internal excitation frequency. The vibration damping structure 60 can be used in any imaging-based detection system for detecting an analyte, for example, in a biomolecular detection and analysis device such as a microscope, and more specifically, in an imaging-based sequencing platform such as a commercially available BGI or ILLUMINA sequencing platform.

For the vibration damping structure 60 with the above characteristics, considering that two-dimensional movement or three-dimensional movement in the X/Y/Z direction is involved for the body 62 when the vibration damping structure 60 is used in the detection system, a double-layer structure formed by connecting the upper structure 66, the intermediate structure 70 and the lower structure 68 is adopted, which can effectively suppress or reduce the influence of external excitation and/or internal excitation on the vibration damping structure 60, and meanwhile, a natural frequency of the body 62 of the vibration damping structure is greater than or equal to $\sqrt{2}$ times an internal excitation frequency, which can further effectively suppress or reduce the influence of internal excitation and thereby improve vibration damping effect of the whole vibration damping structure 60. The "internal excitation" is a concept defined relative to the external excitation. As used herein, vibrations generated by the interaction of internal structure/components/connection of the vibration damping structure 60 can be referred to as internal excitation, and vibrations generated externally of the vibration damping structure 60 and capable of influencing or being transmitted to the vibration damping structure 60 can be referred to as external excitation.

Specifically, the body 62 can be connected to the detection system by the support. In an embodiment of the present application, the detection system is illustrated as a sequencing system 300. It would be appreciated that in other embodiments, the detection system can also be another detection system that is sensitive to vibrations. Referring to FIGS. 1-4, in the illustrated embodiment, the body 62 comprises a carrier module 100 configured to carry and/or move a reaction device 200. The carrier module 100 is mounted on a lower structure 68, and the reaction device is detachably mounted on the carrier module 100. An imaging module 10 is configured to photograph the reaction device 200 fixedly placed on the carrier module 100. A fluid path system is provided in the sequencing system 300, and a reaction reagent/solution can be introduced into the reaction device 200 through the fluid path system. The reaction device 200 is provided with one or more channels in which the reaction reagent/solution or the like is located, a target nucleic acid molecule is immobilized in the reaction device 200 in advance, and a nucleotide analogue/substrate is placed in the reaction reagent/solution. The imaging module 10 is provided above the reaction device 200, so that during the sequencing of a nucleic acid molecule, an image of the nucleic acid molecule with an optically detectable label, such as a fluorescent molecule, in a specific position (Field of View, FOV) of the reaction device 200 can be acquired. The reaction device 200 is, for example, a flowcell, or comprises a flowcell and a plastic frame in which the flowcell can be mounted. It would be appreciated that the detection system may be other systems that comprise the imaging module 10.

In some embodiments, the imaging module 10 comprises an automatic focusing module. When the automatic focusing module is used to focus on a specific position of the reaction device 200, the imaging module 10 is immobilized, and the carrier module 100 drives the reaction device 200 to move in a plane perpendicular to an optical axis OP according to information/instructions of the automatic focusing module, so that the imaging module 10 can acquire images of different positions on the reaction device 200. In one example, the imaging module 10 is a total internal reflection fluorescence microscopy system, which is susceptible to various factors, including vibrations, during signal acquisition, and is sensitive to vibrations, such that vibrations generated by an excitation source (both external and internal) of the sequencing system can have a significant effect on the imaging performance.

For the vibration damping structure 60 provided in the sequencing system 300, the excitation that affects the performance is mainly divided into two parts: external excitation that comes from the outside and is generated by the surrounding environment, and internal excitation that comes from the inside and is primarily caused by movement of the imaging module 10 and/or the carrier module 100. In one example, the natural frequency of the vibration damping structure 60 in the sequencing system 300 is made not equal to the external excitation frequency.

In one specific example, for the vibration damping structure 60 in the sequencing system 300, the external excitation includes vibrations generated by a series of factors during normal operation of the sequencing system 300, such as walking of people, communication between people, vibration of air conditioner, and operation of other modules/structures of the sequencing system such as internal fan and pump, and also includes low frequency vibrations transmitted via ground, etc. This part of excitation will be transmitted to the body 62, including the imaging module 10, via the support 64 of the sequencing system 300, causing the vibration damping structure 60 to vibrate as a whole.

In one example, the vibration damping structure 60 provided in the sequencing system 300 comprises a carrier module 100, and the internal excitation of the vibration damping structure 60 is primarily from the movement of the imaging module 10 and/or the carrier module 100 while the sequencing system is running Specifically, the movement of the carrier module 100 includes XY two-dimensional movement or XYZ three-dimensional movement, and the movement of the imaging module 10 includes excitation generated when a camera and a fan are in operation. The carrier module 100 provides movement of the reaction device 200 in a two-dimensional direction of XY or three directions of XYZ, so that the imaging module 10 can acquire images of test areas of the entire reaction device 200; generally, fluorescent molecules are fragile, the light emitting behavior of the fluorescent molecules is susceptible to various factors, and especially a single or a few fluorescent molecules are quite sensitive to light intensity, duration of lightening, and the like, so that the carrier module 100 is required to respond quickly, and movement featuring high speed and sudden stop will bring movement excitation to the entire system.

This part of excitation acts within the vibration damping structure 60 and causes interaction within the structure to generate vibrations.

Frequency, amplitude and phase are three important parameters for evaluating vibration signals, wherein the frequency corresponds to reciprocal of a period, the amplitude refers to a maximum position that a mechanism moves relative to an equilibrium position during vibration, and the phase describes the relative position relationship between a vibration signal and a trigger pulse, and generally a positive peak value of the vibration signal is generated after the trigger pulse. In one example, the effectiveness of the designed vibration damping structure 60 is evaluated by the applicant using the quality of the images acquired by the imaging module 10. Specifically, in the sequencing system 300 comprising the imaging module 10, the vibration damping structure 60 is designed primarily to reduce the effect of vibration on imaging, and thus the vibration signal can be evaluated by evaluating the quality of the images. In one example, the sequencing system 300 acquires signals from multiple fields of view of the reaction device by moving the carrier module 100, and identifies bases/determines nucleic acid sequences by using acquired signals, i.e., information of light-emitting positions (spots or dots) on the reaction device; if the carrier module 100 vibrates during the exposure process of the camera, the imaging position of an object may shift, and the dots may jitter and may have tails in severe cases, i.e., the image may be blurred due to movement, so that it is possible to evaluate whether the vibration damping structure 60, including the carrier module 100, is at rest, or whether the vibration signals are so reduced that they do not affect sequencing, by determining whether the image is clear.

Figure 5:
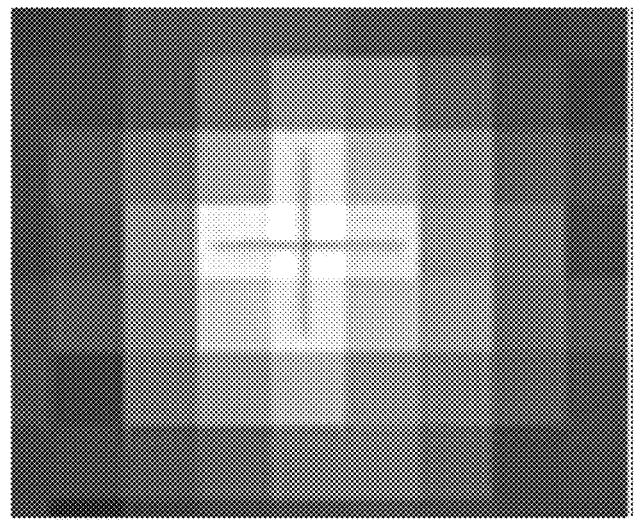
FIG. 5 is a spot image resulting from imaging of light source by an imaging module according to an embodiment of the present application.

There are many methods for determining whether an image is clear, and there is no limitation for this in this embodiment. In one example, image definition is estimated by calculating image sharpness. In the sequencing system 300 that performs sequencing based on fluorescence detection, such as a single-molecule fluorescence detection platform, a spot in an image corresponds to one or a few fluorescent molecules, and the intensity distribution of the spot matches or approximates to a Gaussian distribution, as shown in FIG. 5. The higher the definition, the sharper the Gaussian distribution. However, the intensity distribution of the spot is no longer characterized by a Gaussian distribution if the vibration of the carrier module 100 causes the image to move. In view of this imaging characteristic, in the present embodiment, it is evaluated that whether the carrier module 100 vibrates (further described later).

In some examples, the upper structure 66 of the vibration damping structure 60 comprises an upper plate 71 for mounting the imaging module 10, and the imaging module 10 can be composed of five parts, i.e., a laser module, an automatic focusing module, an illuminator module, an objective lens module and a camera module.

In some examples, the lower structure 68 of the vibration damping structure 60 comprises a lower plate 73 for mounting the carrier module 100, the carrier module 100 is for carrying the reaction device 200, and the carrier module 100 can provide positioning and clamping of the reaction device 200 to allow it to be butted to a liquid path system of the sequencing system 300. The reaction device 200 with a high surface evenness is beneficial to stable focus tracking when images are continuously acquired in sequencing. Preferably, because the working distance of the objective lens in the imaging module 10 is relatively small, the positioning of the reaction device 200 needs to meet certain requirements in order to prevent damage and to ensure the repeatability. The use of the carrier module 100 to adjust the position of the reaction device 200 will be further illustrated later.

The carrier module 100 comprises a high-precision two-dimensional movement platform and a two-stage pitch adjustment structure, which realizes the butting of the reaction device 200 to the imaging module 10, provides two-dimensional movement for the reaction device 200, and enables the field of view in acquisition of the imaging module 10 to cover the whole or a part of the test area of the reaction device 200; the surface of the reaction device 200 is perpendicular to an optical axis of the objective lens when images of different fields of view are acquired. Preferably, an optical axis of the imaging module 10 is not only perpendicular to the surface of the reaction device 200, but also perpendicular to a moving direction of the two-dimensional moving platform, so that the laser in the imaging module 10 can sufficiently and uniformly irradiate the whole FOV, and thus the spots (fluorescent dots) are symmetrically and uniformly excited.

Referring to FIG. 1, in embodiment 1, the intermediate structure 70 comprises a first connecting member 72 and a second connecting member 74, and the upper structure 66 and the lower structure 68 each have left and right sides. The first connecting member 72 and the second connecting member 74 are a plate-shaped structure and a column-shaped structure, respectively. One of the first connecting member 72 and the second connecting member 74 connects the left side of the lower structure 68 and the left side of the upper structure 66, and the other connects the right side of the lower structure 68 and the right side of the upper structure 66.

Specifically, in the illustrated embodiment, the number of the first connecting member 72 is one, and that of the second connecting members 74 is two. The first connecting member 72 connects the left side of the lower structure 68 and the left side of the upper structure 66, and the second connecting members 74 connect the right side of the lower structure 68 and the right side of the upper structure 66. It would be appreciated that in other embodiments, the first connecting member 72 may connect the right side of the lower structure 68 and the right side of the upper structure 66, and the second connecting member 74 may connect the left side of the lower structure 68 and the left side of the upper structure 66.

Figure 2:
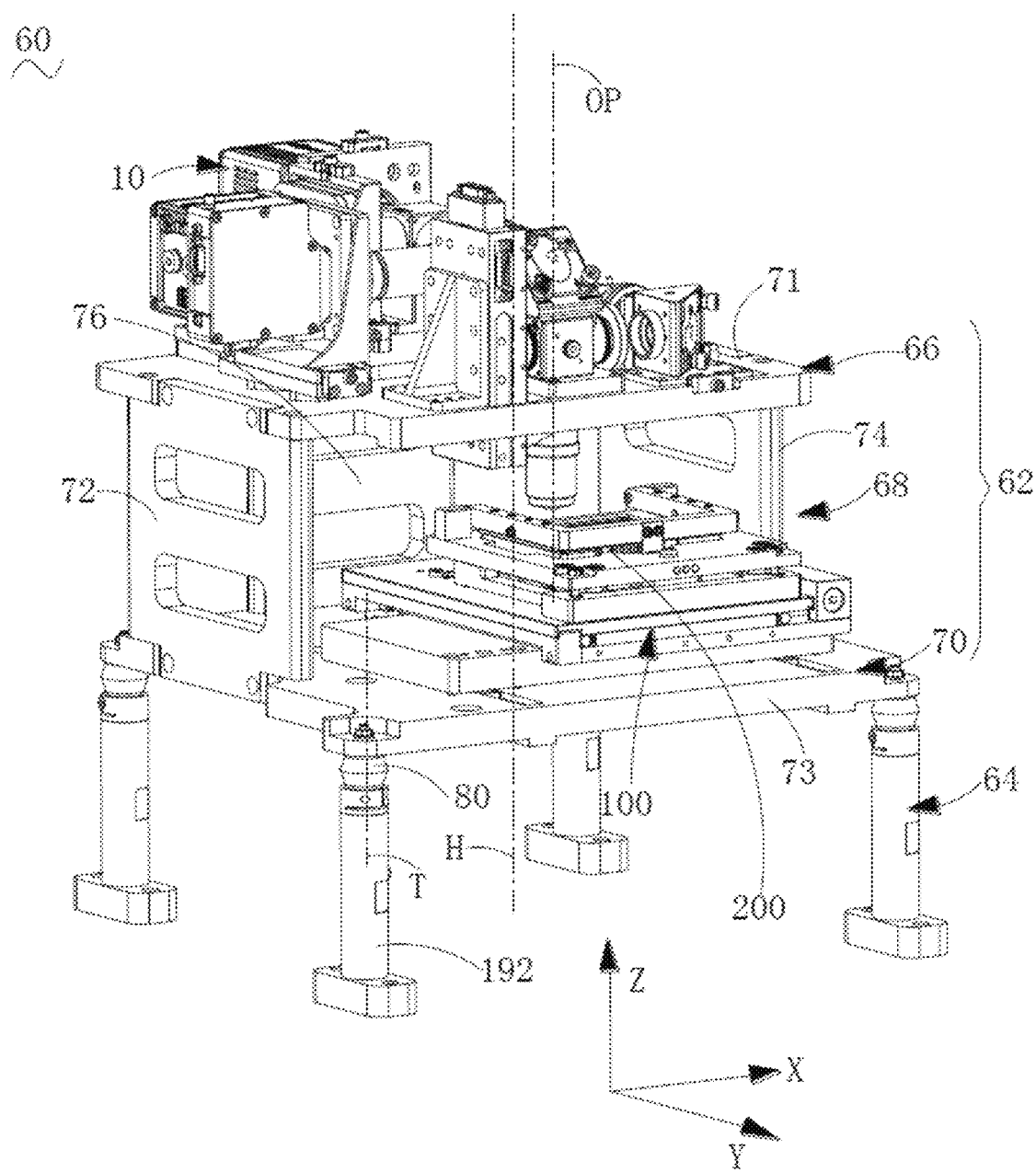
FIG. 2 is another structural schematic view of a vibration damping structure according to an embodiment of the present application.

Referring to FIG. 2, in embodiment 2, the intermediate structure 70 comprises a first connecting member 72 and a second connecting member 74, and the upper structure 66 and the lower structure 68 each have left and right sides. The first connecting member 72 and the second connecting member 74 are both plate-shaped structures.

One of the first connecting member 72 and the second connecting member 74 connects the left side of the lower structure 68 and the left side of the upper structure 66, and the other connects the right side of the lower structure 68 and the right side of the upper structure 66.

Specifically, in the illustrated embodiment, the first connecting member 72 connects the left side of the lower structure 68 and the left side of the upper structure 66, and the second connecting member 74 connects the right side of the lower structure 68 and the right side of the upper structure 66. It would be appreciated that in other embodiments, the first connecting member 72 may connect the right side of the lower structure 68 and the right side of the upper structure 66, and the second connecting member 74 may connect the left side of the lower structure 68 and the left side of the upper structure 66.

Specifically, in embodiment 1, since the two second connecting members 74 used in the double-layer structure are isotropic and only one relatively thin first connecting member 72 is provided on the left side, there is a concern that the strength in the X direction is insufficient. Therefore, in embodiment 2, the two second connecting members 74 on one side are changed into a plate-shaped structure, which is substantially the same as the structure of the first connecting member 72. Preferably, the first connecting member 72 and the second connecting member 74 are symmetrically arranged along a center line H of the body 62, i.e., the first connecting member 72 and the second connecting member 74 symmetrically connect the upper plate 71 and the lower plate 73, thus enhancing the strength of the vibration damping structure 60 in the X direction.

Further, the intermediate structure 70 comprises a third connecting member 76. The third connecting member 76 is a plate-shaped structure, the upper structure 66 and the lower structure 68 each have a rear side, and the third connecting member 76 connects the rear side of the lower structure 68 and the rear side of the upper structure 66. This further enhances the strength of the vibration damping structure 60 in the X direction and also can increase the strength in the Y direction.

In one specific embodiment, the first connecting member 72, the second connecting member 74 and the third connecting member 76 are each a part of an integrated structure. For example, the integrated structure may be similar to a tank without a front face; the upper structure 66 and the lower structure 68 are like the top and bottom, respectively, of the tank, the first connecting member 72 and the second connecting member 74 are like two side structures, respectively, of the tank, and the third connecting member 76 is like the rear of the tank; the first connecting member 72, the second connecting member 74 and the third connecting member 76 are each a part of one structure.

By testing the above structures, it is found that the vibration damping structures 60 of the embodiments 1 and 2 can effectively damp/resist vibration, and relatively, the vibration damping structure 60 of embodiment 2 has a better vibration damping effect than the vibration damping structure 60 of embodiment 1. It is believed by the applicant that, relatively speaking, the mass distribution may be relatively non-uniform in the vibration damping structure 60 of embodiment 1, while in the structure of embodiment 2, positions of various components of the imaging module 10 in the upper structure 66 are rearranged, such that the center of mass is on the center line H of the entire body 62 or the offset of the center of mass from the center line is within a desired range, and thus the mass distribution is relatively uniform.

Materials of the upper plate 71, the lower plate 73 and the intermediate structure 70 of embodiments 1 and 2 may be aluminum alloy. Further, the lower plate 73 is heavier than the upper plate 71, so that the center of gravity can be shifted downward, increasing the stability of the vibration damping structure 60.

Figure 3:
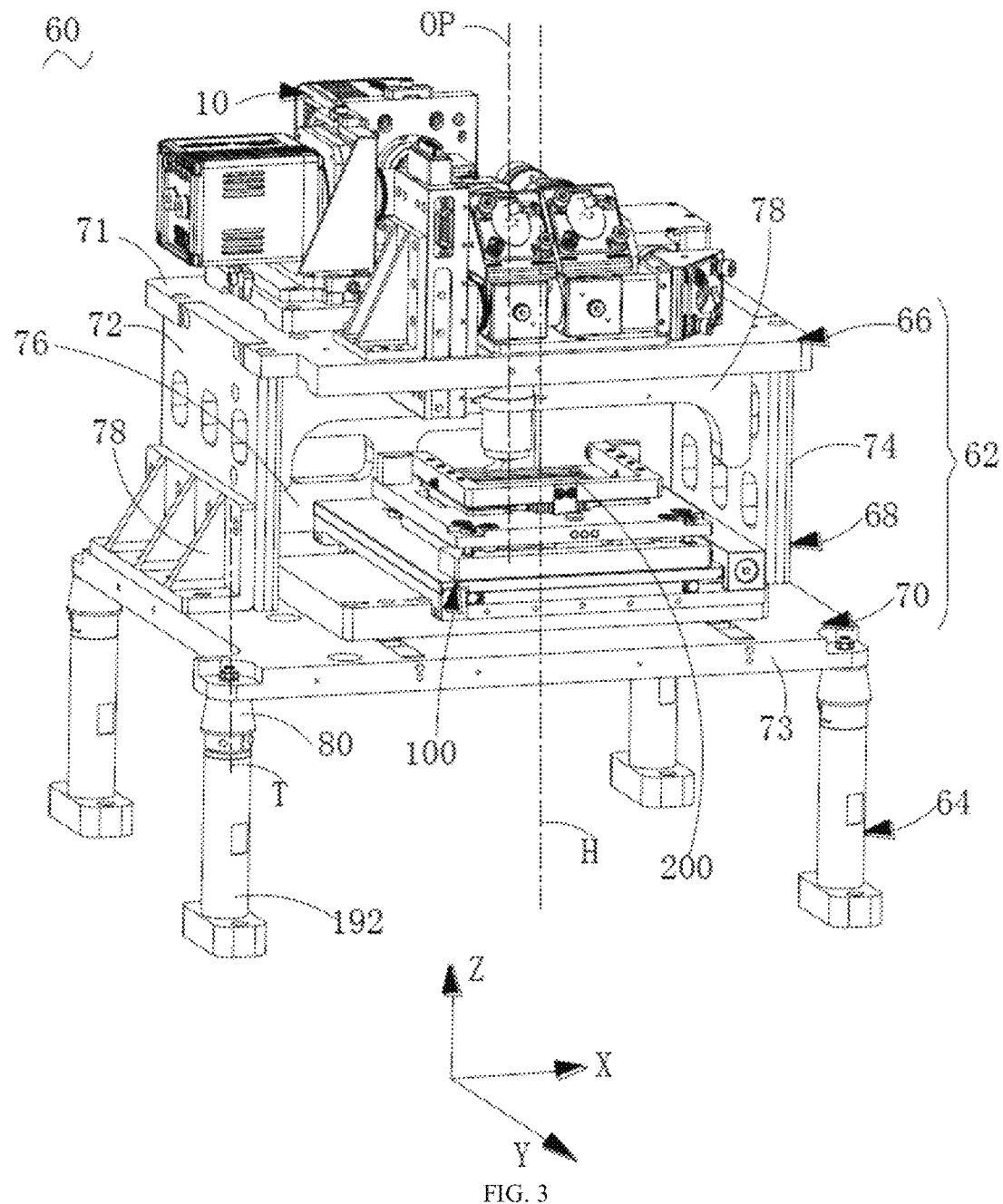
FIG. 3 is yet another structural schematic view of a vibration damping structure according to an embodiment of the present application.
Figure 4:
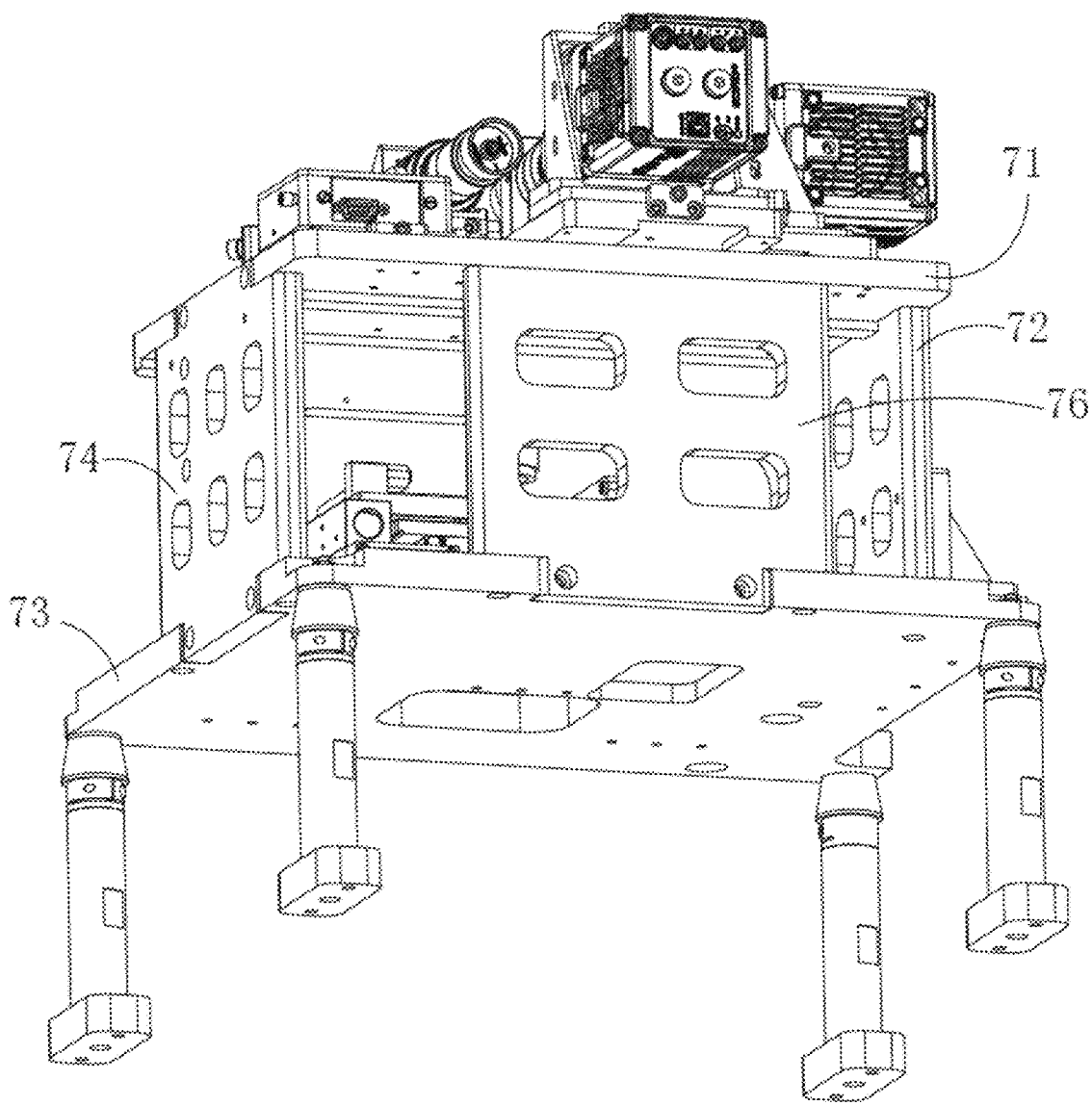
FIG. 4 is still another structural schematic view of a vibration damping structure according to an embodiment of the present application.

Referring to FIGS. 3 and 4, in embodiment 3, the vibration damping structure 60 comprises reinforcing members 78, and the reinforcing members 78 are capable of lowering the center of mass of the body 62. The reinforcing member 78 connects the first connecting member 72 and the lower structure 68, and the reinforcing member 78 connects the first connecting member 72, the upper structure 66 and the second connecting member 74.

Specifically, since Z-direction high-precision movement of the objective lens comes from the axis Z mounted on the upper plate 71, the thickness of the upper plate 71 can be increased to ensure the stability of the axis Z during installation and positioning. Since most of the FOVs involved in sequencing are in the X direction, the excitation caused by the two-dimensional movement platform is substantially in the X direction. In order to further enhance the strength of the entire vibration damping structure 60 in the X direction, in the illustrated embodiment, the number of the reinforcing members 78 is two. A cross beam is provided in the middle as one of the reinforcing members 78 and it connects the first connecting member 72, the upper structure 66 and the second connecting member 74, and another reinforcing member 78 is provided on the left side and it connects the first connecting member 72 and the lower structure 68.

More specifically, the reinforcing member 78 connects an outer side of the first connecting member 72 and an upper side of the lower structure 68. The reinforcing member 78 connects an inner side of the first connecting member 72, a lower side of the upper structure 66 and an inner side of the second connecting member 74.

It would be appreciated that in other embodiments, the reinforcing member 78 connects the first connecting member 72 and the lower structure 68, or the reinforcing member 78 connects the first connecting member 72, the upper structure 66 and the second connecting member 74.

In order to lower the center of mass of the body 62, the material of the lower plate 73 and the intermediate structure 70 may be changed to steel. Preferably, in embodiments 1-3, the density of the material of the lower plate 73 and the density of the material of the intermediate structure 70 being greater than that of the upper plate 71 can lower the center of mass of the body 62, which is beneficial to the stability of the vibration damping structure 60. It would be appreciated that the density of the material of the lower plate 73 or the density of the material of the intermediate structure 70 being greater than that of the upper plate 71 can also lower the center of mass of the body 62.

In any of embodiments 1-3, if the first connecting member 72, the second connecting member 74 and/or the third connecting member 76 are plate-shaped structures, the plate-shaped structure(s) may have one or more through holes/hollow holes, and the plate-shaped structure can adjust the balance of the strength of the vibration damping structure 60 in the X, Y and/or Z directions by comprising the through holes or hollow holes.

In any of embodiments 1-3, the support 64 comprises vibration damping members 80 and supporting legs 192, the detection system comprises a supporting substrate 83 (see FIG. 6), the body 62 is mounted on the vibration damping members 80, and the vibration damping members 80 are mounted on the supporting substrate 83 through the supporting legs 192. Thus, the body 62 is butted to the detection system, isolating external excitation to a great extent.

Specifically, the vibration damping member 80 may comprise vibration-proof gel pads (e.g., silicone). The number of the vibration-proof gel pads may be four, the number of the supporting legs 192 may be four, and each supporting leg 192 connects a corresponding vibration-proof gel pad and the lower structure 68.

Preferably, the principal axis T of the vibration damping member 80 is parallel to the direction of optical axis OP of the imaging module 10. In any of embodiments 1-3, the principal elastic axis T of each vibration-proof gel pad is parallel to the Z-axis direction.

The following further illustrates the vibration damping structure 60, the sequencing system 300 and/or the connections between the vibration damping structure 60 and other modules of the sequencing system based on the application of the vibration damping structure 60 of embodiments 1-3 to the sequencing system 300. The sequencing system 300 realizes sequence determination of a nucleic acid molecule by acquiring signals from nucleotides (nucleotide analogues, if not otherwise specified) bound to the nucleic acid molecule on the reaction device 200, wherein the nucleotides carry optically detectable labels, e.g., fluorescent molecules.

Specifically, four vibration damping members 80 of the same type may be used to support the imaging module 10, the vibration damping members 80 and the supporting legs 192 constitute the support 64, and the principal elastic axes of the four vibration damping members 80 are all along the Z-axis direction or parallel to the Z-axis direction; the upper structure 66, the lower structure 68, the intermediate structure 70 and the imaging module 10 constitute the body 62.

The vibration damping structure 60 of the sequencing system can be divided into two parts, i.e., a body 62 and a support 64. Specifically, the vibration damping structure comprises the following parts.

(1) An imaging module 10: The imaging module is composed of a laser module, an automatic focusing module, an illuminator module, an objective lens module and a camera module. The laser module provides laser with proper power for the imaging module 10, and the laser can be coupled by a coupler to obtain parallel coupled laser; the illuminator module allows the coupled laser to enter an objective lens at a proper angle; the automatic focusing module enables Z-axis linkage of the objective lens and allows the reflected fluorescence in each field of view (FOV for short, namely a pixel window of an image) to be converged on a focal plane of the objective lens; the objective lens module transmits the coupled light transmitted in the upstream section to a target plane at a proper angle to realize total internal reflection; the camera module receives the reflected light to realize acquisition of fluorescent dots (spots or dots) in the FOV.

(2) A reaction device module: The reaction device module comprises a reaction device 200 and a reaction device clamp and provides positioning and clamping of the target reaction device 200 to allow it to be butted to a liquid path system. A reaction device 200 with high evenness is preferred to ensure stable focus tracking of the reaction device 200 (e.g., a flowcell) during the whole sequencing process. The positioning of the reaction device 200 needs to meet certain requirements in order to prevent damage and to ensure the repeatability in the case that the working distance of the objective lens in the imaging module is relatively small.

(3) A carrier module 100: The carrier module comprises a high-precision two-dimensional movement platform and a two-stage pitch adjustment structure, and it connects the reaction device module and the imaging module 10, provides two-dimensional or three-dimensional movement for the reaction device 200, and enables the field of views of the objective lens to cover the entire detection area of the reaction device 200. For all the fields of view, the surface of the reaction device 200 is perpendicular to an optical axis of the objective lens. An optical axis of the imaging module 10 is not only perpendicular to the surface of the reaction device 200, but also perpendicular to a moving direction of the two-dimensional micro-movement platform, so that the laser in the system can sufficiently and uniformly irradiate the whole FOV plane, and the thus fluorescent dots are symmetrically and uniformly excited.

(4) A support 64: The support comprises four vibration-proof gel pads and supporting legs 192, which realizes the butting of the imaging module 10 to the whole machine, isolating external excitation to a great extent. The sequencing system 300 identifies base sequence information primarily by imaging, and the support 64 serves as a medium for connection to the whole machine, and preferably, is expected to greatly attenuate external excitation or excitation brought by the while machine.

As can be seen from the above, the sequencing system 300 captures signals of fluorescent dots in the reaction device 200 through the imaging module 10, and then converts the optical signals into corresponding base information, thereby determining corresponding nucleic acid sequence.

The human genome has a total of 23 chromosome pairs, i.e., 22 autosome pairs and one sex chromosome pair, and contains about 3.16 billion base pairs in total. In order to determine the sequence of the human genome, the genome is often determined multiple times (sequencing depth) to improve the reliability of the sequencing result, and there is a requirement for the throughput (the amount of reads that can be obtained) of the sequencing system 300.

In some examples, the requirement for the throughput is met by allowing the reaction device 200 to contain multiple channels, i.e., have a larger reaction/detection area.

Generally, the structure or system design needs to take into account the relative displacement of the objective lens and the reaction device 200 in the X/Y directions since each channel contains hundreds of FOVs; considering the unevenness of the surface of the reaction device 200, it is preferred to add a Z-axis dimension to realize automatic focus tracking during sequencing.

When a related structure or system is designed, the three-dimensional movement is decomposed, which facilitates fast and accurate sequencing, shortens the image (FOV) acquisition time, and is particularly suitable for a single-molecule sequencing system 300. In the single-molecule sequencing system 300, a fluorescent signal of a single molecule (a single molecule or a few molecules) is very fragile (for example, long-time exposure can cause fast quenching of fluorescence) and thus fast image acquisition is needed; in one example, the carrier module 100 carrying the reaction device 200 is relatively heavy, and the carrier module 100 is provided with two-dimensional movement in the X/Y directions in view of the convenience in carrying and placing the reaction device 200 by an operator; the objective lens is relatively light, and it is provided with Z-direction high-precision movement in view of the fact that the objective lens needs to be protected.

Further, the whole vibration damping structure 60 is designed to be a double-layer structure (as in embodiment 1) with a plate-shaped first connecting member 72 and two column-shaped second connecting members 74 in between, which facilitates a large range of movement in the X/Y directions; as shown in FIGS. 1-4 and 6, the upper double-layer structure is referred to as a body, and four vibration-proof gel pads are connected with a supporting substrate 83 by four cylindrical supporting legs 192; in one example, most of the whole vibration damping structure 60 is made of aluminum alloy; the four vibration-proof gel pads are used as the support 64 to connect to the double-layer structure, so that the suppression of vibrations by the vibration damping structure 60 is enhanced, and the support 64 can effectively isolate the upper double-layer structure from vibrations.

In some examples, since the X/Y two-dimensional platform and axis Z are in movement during sequencing, vibration characteristics of the entire vibration damping structure 60 can be known from dynamic characteristics of the two-dimensional platform and axis Z in the working positions. Therefore, at initial design stage, the applicant sets both the X/Y two-dimensional platform and axis Z at the most common working positions: the X/Y two-dimensional platform is in a state of photographing for objective lens imaging most of the time, and the working position of the X/Y two-dimensional platform used is one when the objective lens is in the middle position of the flow channel of the reaction device 200; the axis Z is in an objective lens focus tracking state most of the time, so that the working position of the axis Z is one that corresponds to a theoretical focal plane.

Since the two cylindrical second connecting members 74 connecting the two layers are isotropic and only one relatively thin first connecting member 72 is provided on the left side, there is a concern that the strength in the X direction is insufficient. Therefore, the two cylindrical second connecting members 74 in embodiment 1 of the structure of the single-molecular gene sequencing system are changed to a thin plate-shaped second connecting member 74 symmetrical to the existing second connecting member on the other side, and further, a plate-shaped third connecting member 76 is added on the back side, thereby enhancing the strength in the X direction of the whole mechanism.

Considering the non-uniform mass distribution in embodiment 1, positions of the modules in the upper structure are rearranged to allow the center of mass to be on the center line of the whole mechanism as much as possible, thereby completing the design of the embodiment 2 of the structure of the single-molecule gene sequencing system, as shown in FIG. 2.

The Z-direction high-precision movement of the objective lens comes from axis Z arranged on the upper plate 71, and the thickness of the upper plate 71 is increased to ensure the stability of the axis Z during installation and positioning; since most of the FOVs involved in sequencing are in the X direction, the excitation caused by the two-dimensional platform is substantially in the X direction; in order to further enhance the strength of the whole mechanism in the X direction, a beam is supposed to be added in the middle to serve as a reinforcing rib, and another reinforcing rib is supposed to be added on the left side; in order to lower the center of mass of the body 62, the material of the lower plate 73 and the connecting plate for the intermediate structure 70 is changed to steel, so as to form embodiment 3 of the structure of the single-molecular gene sequencing system, as shown in FIGS. 3 and 4.

Therefore, structural schemes for three single-molecule gene sequencing systems are designed, and the influence of vibration on the structures is further evaluated subsequently.

The magnitude and change in vibration experienced by the vibration damping structure 60 can be measured using known methods, including using commercially available measuring equipment such as a vibration meter, and there is no limitation for this in the present application.

In some examples, the applicant indirectly evaluates the vibration damping performance of the vibration damping structure 60 by evaluation of the quality of the acquired images. It is found in test that the evaluation method is simple and direct, the test platform is easy to build, less equipment is required, and the operation steps are simple; the larger the amplitude is and the more significant the image difference is, the more accurate the evaluation is. Meanwhile, the method can also test and verify whether the built sequencing system 300 is reliable or whether it can realize preset functions. Specifically, the sequencing system 300 has an imaging function by means of the imaging module 10 contained therein, and thus it has inherent adaptability in evaluating the vibration of the system simply and intuitively through images. More directly, the vibration suppression effect of the sequencing system 300/vibration damping structure 60 can be determined by observing whether the image is blurred.

If the carrier module 100 vibrates during the exposure of the camera, the imaging position of the object will shift, and the dots will jitter and may have tails when the image is observed, so that the image is blurred visually. By determining whether the image is clear, it can be evaluated whether the carrier module 100 is already at rest or is in a state of not affecting signal acquisition (or has negligible effect).

The method for determining whether the image is clear is not limited in this embodiment. In one example, the applicant evaluates image definition by calculating image sharpness. FIG. 5 shows the intensity distribution of an ideal dot in the image, which is a Gaussian distribution or approximates to a Gaussian distribution.

The higher the definition, the sharper the peak of the Gaussian distribution. However, if the image moves due to vibration of the carrier module 100, pixels in a small imaging area of the camera (e.g., 3×3 pixels, which is approximately the size of a fluorescent molecule in an ideal state on the image plane) receive an intensity signal from the same signal source at different time. The intensity value of the signal source is then evenly distributed among n pixels in the imaging area. Therefore, the difference between the pixels in the imaging area becomes small and the intensity distribution is no longer characterized by a Gaussian distribution. By virtue of this imaging characteristic, an indirect measurement scheme for evaluating vibration can be established.

The single-molecular gene sequencing system is a sequencing system for identifying a single base through a total internal reflection fluorescence imaging system (Tirf). A single-molecular base signal is extremely weak, and its microscopic imaging requires a high magnification, high NA and small depth of field, and it is extremely sensitive to external interference including environmental vibration. The excitation affecting the single-molecule gene sequencing system is mainly divided into two parts: external excitation that comes from the outside and is generated by the surrounding environment, and internal excitation that comes from the inside and is caused by the imaging module 10.

(1) External excitation: During normal operation of the system, a series of factors, such as walking of people, communication between people, vibration of air conditioner, and operation of fan and pump in the whole machine, can generate external excitation, and external excitation also includes low-frequency vibration transmitted via ground. This part of excitation is transmitted to the single-molecular gene sequencing system platform via the supporting legs 192, causing the system platform to vibrate as a whole.

Generally, the frequency of earth pulsation-type ground vibration is mainly 0-1 Hz, the frequency of vibration caused by walking of laboratory workers is 1-3 Hz, the vibration caused by the ventilating duct, the transformer and the motor is 6-65 Hz, and the building itself typically oscillates at a frequency of 10-100 Hz.

External excitation can be tested through an experiment. In one example, the applicant arranges a triaxial acceleration sensor probe on the support 64 installed in the sequencing system 300, normal working condition is established, the walking of people and communication between people are not required to be shielded, the whole machine is in an on state, and the internal fan and pump of the sequencing system 300 are in an operation state. The experiment shows that with regard to external excitation, the first-order peak in the X direction is 4.5 Hz, the first-order peak in the Y direction is 4 Hz, and the first-order peak in the Z direction is 11.5 Hz. The excitation frequency of the excitation source in the environment can thus be known, and the data can be used as a comparison basis for subsequent finite element analysis.

(2) Internal excitation: The sequencing system 300 identifies a base sequence mainly by using a camera to acquire, via the objective lens, a fluorescent dot excited by laser in the reaction device 200, so the whole imaging module 10 is a whole, and if any component in the optical path vibrates relative to other parts, image acquisition will be affected. Internal excitation affecting the imaging module 10 mainly includes: movement of two-dimensional micro-movement platform, Z-axis movement, operation of camera and fan, etc.

Analysis of System Response Characteristic Under External Excitation

With regard to external excitation, generally a vibration system for which vibration isolation measures have been adopted no longer vibrates greatly, and for a single-molecule gene sequencing system positioned on a bottom plate, a dynamic model can be simplified according to a single-stage vibration isolation mode. By the simplification as an ideal rigid body dynamics model, it is convenient to observe the essential law of vibration suppression, and then a complex problem, namely optimization of the vibration suppression, is analyzed.

Figure 7:
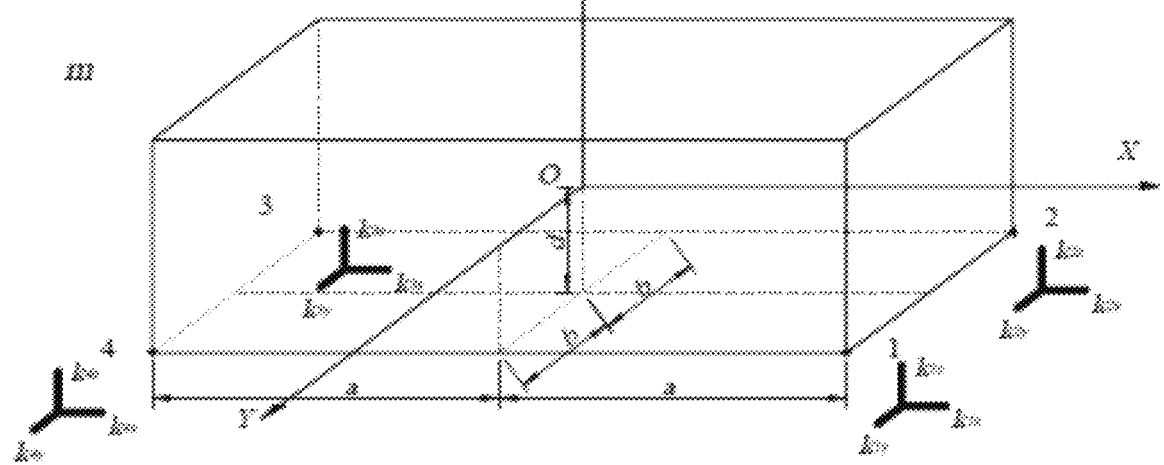
FIGS. 7-11 are drawings related to vibration analysis of the vibration damping structure according to an embodiment of the present application.

FIG. 7 shows a simplified model of a single-molecule gene sequencing system.

The body 62 of the single-molecule gene sequencing system is a vibration isolation target of the support 64. Since the mass and rigidity of the body 62 are much greater than the support 64 supporting it, the body 62 can be simplified as a rigid body, and the weight of the vibration-proof gel pads can be ignored, thereby forming a simplified model of the body 62, i.e., the vibration-proof gel pads are simplified as four mass points symmetrically distributed to support the body 62 which is simplified as a rigid body.

Assuming that the mass of the body 62 is m, the center of mass of the body 62 is taken as the origin O of the coordinate system xyz, and Ixx, Iyy and Izz are the moments of inertia of the body 62 in the X/Y/Z directions, respectively, relative to the center of mass O; four vibration-proof gel pads are defined as mass points i=1, 2, 3 and 4, respectively, and according to the coordinate values of the vibration-proof gel pads in FIG. 7, each vibration-proof gel pad is simplified as a spring and a damping structure, so that values of rigidity and damping corresponding to the three directions can be simplified as $k_{ix}$, $k_{iy}$, $k_{iz}$, $c_{ix}$, $c_{iy}$, and $c_{iz}$, respectively.

A single-stage passive vibration isolation system is thus obtained, and it has six degrees of freedom. Assuming that initial positions are all 0, and the body 62 is in a small displacement vibration state under the excitation; u, v and w are linear displacements in the X, Y and Z directions, respectively, and $\alpha$, $\beta$ and $\gamma$ are angular displacements around the axes X, Y and Z, respectively; the influence of the damping C is ignored, and six independent movement differential equations can be obtained according to the momentum theorem and the momentum moment theorem of classical mechanics, which are shown as follows.

$$m\ddot{u}+(\Sigma_{i=1}^{4}k_{ix})u+(\Sigma_{i=1}^{4}k_{ix}d)\beta-(\Sigma_{i=1}^{4}k_{ix}b)\gamma=0 \quad (3\text{-}1)$$

$$m\ddot{v}+(\Sigma_{i=1}^{4}k_{iy})v+(\Sigma_{i=1}^{4}k_{iy}a)\gamma-(\Sigma_{i=1}^{4}k_{iy}d)\alpha=0 \quad (3\text{-}2)$$

$$m\ddot{w}+(\Sigma_{i=1}^{4}k_{iz})w+(\Sigma_{i=1}^{4}k_{iz}b)\alpha-(\Sigma_{i=1}^{4}k_{iz}a)\beta=0 \quad (3\text{-}3)$$

$$I_{xx}\ddot{\alpha}+(\Sigma_{i=1}^{4}k_{ix}d^2+\Sigma_{i=1}^{4}k_{iz}b^2)\alpha-(\Sigma_{i=1}^{4}k_{iy}d)v+(\Sigma_{i=1}^{4}k_{iz}b)w-(\Sigma_{i=1}^{4}k_{iz}ab)\beta-(\Sigma_{i=1}^{4}k_{iy}ad)\gamma=0 \quad (3\text{-}4)$$

$$I_{yy}\ddot{\beta}+(\Sigma_{i=1}^{4}k_{ix}d^2+\Sigma_{i=1}^{4}k_{iz}a^2)\beta+(\Sigma_{i=1}^{4}k_{ix}d)u-(\Sigma_{i=1}^{4}k_{iz}a)w-(\Sigma_{i=1}^{4}k_{iz}ab)\alpha-(\Sigma_{i=1}^{4}k_{ix}bd)\gamma=0 \quad (3\text{-}5)$$

$$I_{xx}\ddot{\gamma}+(\Sigma_{i=1}^{4}k_{ix}b^2+\Sigma_{i=1}^{4}k_{iy}a^2)\gamma-(\Sigma_{i=1}^{4}k_{ix}b)u+(\Sigma_{i=1}^{4}k_{iy}a)v-(\Sigma_{i=1}^{4}k_{iy}ad)\alpha-(\Sigma_{i=1}^{4}k_{ix}bd)\beta=0 \quad (3\text{-}6)$$

where m represents mass of the body; u represents displacement of the body along the axis X; v represents displacement of the body along the axis Y; w represents displacement of the body along the axis Z; $k_{ix}$ represents rigidity of the body in the X direction; $k_{iy}$ represents rigidity of the body in the Y direction; $k_{iz}$ represents rigidity of the body in the Z direction; a represents half of the length of the body; b represents half of the width of the body; d represents half of the height of the body; $I_{xx}$ represents rotational inertia in the X direction relative to the center of mass; $I_{yy}$ represents rotational inertia in the Y direction relative to the center of mass; $I_{zz}$ represents rotational inertia in the Z direction relative to the center of mass; a represents angular displacement of the body around the axis X; $\beta$ represents angular displacement of the body around the axis Y; $\gamma$ represents angular displacement of the body around the axis Z.

The above 6 independent movement differential equations are based on the 6 degrees of freedom, i.e., u, v, w, $\alpha$, $\beta$ and $\gamma$, and for ease of calculation, the six differential equations are simplified, and it can be assumed that: $l_{11}=\Sigma_{i=1}^{4}k_{ix}$; $l_{22}=\Sigma_{i=1}^{4}k_{iy}$; $l_{33}=\Sigma_{i=1}^{4}k_{iz}$; $l_{44}=\Sigma_{i=1}^{4}k_{iy}d^2+\Sigma_{i=1}^{4}k_{iz}b^2$; $l_{55}=\Sigma_{i=1}^{4}k_{ix}d^2+\Sigma_{i=1}^{4}k_{iz}a^2$; $l_{66}=\Sigma_{i=1}^{4}k_{ix}b^2+\Sigma_{i=1}^{4}k_{iy}a^2$; $l_{16}l_{61}=-\Sigma_{i=1}^{4}k_{ix}b$; $l_{15}=l_{51}=\Sigma_{i=1}^{4}k_{ix}$; $l_{24}=l_{42}=-\Sigma_{i=1}^{4}k_{iy}d$; $l_{26}=l_{62}=\Sigma_{i=1}^{4}k_{iy}a$; $l_{34}=l_{43}=\Sigma_{i=1}^{4}k_{iz}b$; $l_{35}=l_{53}=\Sigma_{i=1}^{4}k_{iz}a$; $l_{45}=l_{54}=-\Sigma_{i=1}^{4}k_{iz}ab$; $l_{46}=l_{64}=-\Sigma_{i=1}^{4}k_{iy}ad$; $l_{56}=l_{65}=-\Sigma_{i=1}^{4}k_{ix}bd$; which can be expressed in matrix form as follows:

$$\begin{bmatrix} m & 0 & 0 & 0 & 0 & 0 \\ 0 & m & 0 & 0 & 0 & 0 \\ 0 & 0 & m & 0 & 0 & 0 \\ 0 & 0 & 0 & I_{xx} & 0 & 0 \\ 0 & 0 & 0 & 0 & I_{yy} & 0 \\ 0 & 0 & 0 & 0 & 0 & I_{xx} \end{bmatrix} \begin{bmatrix} \ddot{u} \\ \ddot{v} \\ \ddot{w} \\ \ddot{\alpha} \\ \ddot{\beta} \\ \ddot{\gamma} \end{bmatrix} + \begin{bmatrix} l_{11} & 0 & 0 & 0 & l_{15} & l_{16} \\ 0 & l_{22} & 0 & l_{24} & 0 & l_{26} \\ 0 & 0 & l_{33} & l_{34} & l_{35} & 0 \\ 0 & l_{42} & l_{43} & l_{44} & l_{45} & l_{46} \\ l_{51} & 0 & l_{53} & l_{54} & l_{11} & l_{56} \\ l_{61} & l_{62} & 0 & l_{64} & l_{65} & l_{11} \end{bmatrix} \begin{bmatrix} u \\ v \\ w \\ \alpha \\ \beta \\ \gamma \end{bmatrix} = \begin{bmatrix} 0 \\ 0 \\ 0 \\ 0 \\ 0 \\ 0 \end{bmatrix} \quad (3\text{-}7)$$

after damping and excitation effect are introduced, the matrices can be simplified as follows:

$$M\{\ddot{X}\}+C\{\dot{X}\}+K\{X\}=\{F\} \quad (3\text{-}8)$$

where M represents mass matrix of the body; C represents damping matrix of the body; K represents rigidity matrix of the body; $\{\ddot{X}\}$ represents absolute acceleration vector of a node;

$\{\dot{X}\}$ represents absolute velocity vector of a node; $\{X\}$ represents absolute displacement vector of a node $\{F\}$ represents excitation vector.

A basic equivalent excitation vector is introduced: $\{F(t)\}=C\{X_0\}\omega_j \cos \omega_j t+K\{X_0\}\sin \omega_j t$ (3-9), where $\omega_j$ represents excitation frequency.

It can be assumed that: $[\Psi]=[\{\varphi_n\}]$ (3-10), $\Omega=\text{diag}[\{2\xi_n\omega_n\}]$ (3-11), and $\Lambda=\text{diag}[\{\omega_n^2\}]$ (3-12), where $[\Psi]$ represents eigen vector matrix (composed of principal modes); $\{\varphi_n\}$ represents the $n^{th}$ order modality; $\xi_n$ represents the $n^{th}$ order damping; $\Omega$ represents eigenvalue matrix obtained by multiplying twice the damping ratio by natural frequency; Λ represents eigenvalue matrix composed of natural frequency squared.

For small damping systems that satisfy the decoupling condition, there is a regularization relationship:

$$[\Psi]^T C[\Psi] = \Omega \quad (3\text{-}13),$$

$$[\Psi]^T K[\Psi] = \Lambda \quad (3\text{-}14);$$

and then by multiplying both sides of equation (3-9) by $[\Psi]^T$, the equation can be simplified as follows:

$[\Psi]^T\{F(t)\} = \Omega\{\tilde{X}_0\}\omega_j \cos \omega_j t + K\{\tilde{X}_0\}\sin \omega_j t$ (3-15); it can be assumed that:

$$\lambda_n = \omega_j/\omega_n, \sin\theta_n = \frac{2\xi_n\lambda_n^3}{\sqrt{\left[1 - \lambda_n^2 + (2\xi_n\lambda_n)^2\right]^2 + (2\xi_n\lambda_n^3)^2}}, \text{ and }$$

$$\cos\theta_n = \frac{1 - \lambda_n^2 + (2\xi_n\lambda_n)^2}{\sqrt{\left[1 - \lambda_n^2 + (2\xi_n\lambda_n)^2\right]^2 + (2\xi_n\lambda_n^3)^2}},$$

where n represents corresponding orders.

By decoupling in modal coordinates, equivalent excitation force can be obtained:

$$q_n = \sqrt{\frac{1 + (2\xi_n\lambda_n)^2}{(1 - \lambda_n^2)^2 + (2\xi_n\lambda_n)^2}} \tilde{x}_{0_n}\sin(\omega_j t - \theta_n). \quad (3\text{-}16)$$

Under fundamental sinusoidal displacement excitation, the $i^{th}$ component of $\{X\}$ is:

$$x_i = \left(\sum_{n=1}^{6} \varphi_i^n \tilde{x}_{0_n} \sqrt{\frac{1 + (2\xi_n\lambda_n)^2}{(1 - \lambda_n^2)^2 + (2\xi_n\lambda_n)^2}} \cos\theta_n \sin\omega_j t\right) - \quad (3\text{-}17)$$

$$\left(\sum_{n=1}^{6} \varphi_i^n \tilde{x}_{0_n} \sqrt{\frac{1 + (2\xi_n\lambda_n)^2}{(1 - \lambda_n^2)^2 + (2\xi_n\lambda_n)^2}} \sin\theta_n \cos\omega_j t\right),$$

where i can be 1-6 for representing 6 degrees of freedom, respectively; $\varphi_i^n$ represents $\{\varphi_n\}$ the $i^{th}$ component of the n-order modality.

Under basic excitation, the dynamic response amplitude-frequency characteristic of the system is as follows:

$$\tilde{x}_i(\omega) = \left[\left(\sum_{n=1}^{6} \varphi_i^n \tilde{x}_{0_n} \sqrt{\frac{[1 + (2\xi_n\lambda_n)^2]\cos^2\theta_n}{(1 - \lambda_n^2)^2 + (2\xi_n\lambda_n)^2}}\right)^2 + \left(\sum_{n=1}^{6} \varphi_i^n \tilde{x}_{0_n} \sqrt{\frac{[1 + (2\xi_n\lambda_n)^2]\sin^2\theta_n}{(1 - \lambda_n^2)^2 + (2\xi_n\lambda_n)^2}}\right)^2\right]^{1/2} \quad (3\text{-}18)$$

The sequencing system 300 is an underdamping system with a damping ratio of 0<ξn<1. Frequency ratio λ is a system parameter related to excitation frequency wj and natural frequency wn of the vibration damping structure 60. When the excitation frequency wj is smaller than the natural frequency wn of the vibration damping structure 60, the frequency ratio λ is less than 1; when the excitation frequency wj is equal to the natural frequency wn of the system, the frequency ratio λ is 1; when the excitation frequency wj is greater than the natural frequency wn of the vibration damping structure 60, the frequency ratio λ is greater than 1.

According to (3-18), the amplitude of $\tilde{x}_i(\omega)$ for each degree of freedom is a curve with an inflection point related to λ, and when λ=1, the corresponding $\tilde{x}_i(\omega)$ reaches its maximum value, that is, the system platform with the corresponding degree of freedom generates resonance, and at this time, the vibration isolator does not damp the vibration, but aggravates the vibration of the platform.

The goal of the design is to avoid resonant frequency for each degree of freedom, and to minimize the effect on the imaging module 10 by allowing the support 64 to absorb vibrations transmitted externally or internally as much as possible. Thus, when the natural frequency of the vibration damping structure 60 does not equal to the external excitation frequency, the effect of the external excitation on the sequencing system 300 can be effectively reduced.

Analysis of System Response Characteristic Under Internal Excitation

For external excitation, the body 62 connected with the support 64 in the sequencing system platform is simplified as a rigid body; for internal excitation, the body 62 can be analyzed separately as a target object. What mainly needs to be done is to allow the relative displacement of the objective lens and the reaction device 200 under the excitation action to meet the requirement for automatic focus tracking of the imaging module 10.

$F_N = K_s X_s$ (3-19), where $F_N$ represents internal excitation; $K_s$ represents rigidity of the body; $X_s$ represents deformation of the body.

On the premise that the internal excitation is constant, according to the formula (3-19), the deformation of the body 62 $X_s$ is inversely proportional to the rigidity of the body 62 $K_s$, and a proper rigidity of the body 62 is required to obtain a very small $X_s$.

$$w_s = \sqrt{\frac{K_s}{M_s}} = \sqrt{\frac{F_N}{M_s X_s}}, \quad (3\text{-}20)$$

where $w_s$ represents natural frequency of the body; $M_s$ represents mass of the body.

According to the formula (3-20), on the premise that the mass is constant, the rigidity of the body 62 is in direct proportion to the natural frequency of the body 62, and increasing the natural frequency $w_s$ increases the rigidity of the body 62. On the premise that the natural frequency is constant, the rigidity of the body 62 is in direct proportion to the mass, and increasing the mass of the body 62 increases the rigidity of the body 62.

Thus, a strong vibration suppression effect can be achieved by increasing the natural frequency of the body 62 in the presence of internal excitation.

Based on the above analysis results for the external and internal excitation, it is necessary to analyze the excitation composition in detail and then analyze the structural model based on the actual excitation if vibration isolation of internal and external excitation is desired.

Analysis of Vibration Isolation Design for External Excitation

External excitation is tested through an experiment. A triaxial acceleration sensor probe is arranged on a bottom plate for mounting a single-molecular gene sequencing system platform, normal working condition is established, the walking of people and communication between people are not required to be shielded, the whole machine is in an on state, and the internal fan and pump are in an operation state.

Figure 8:
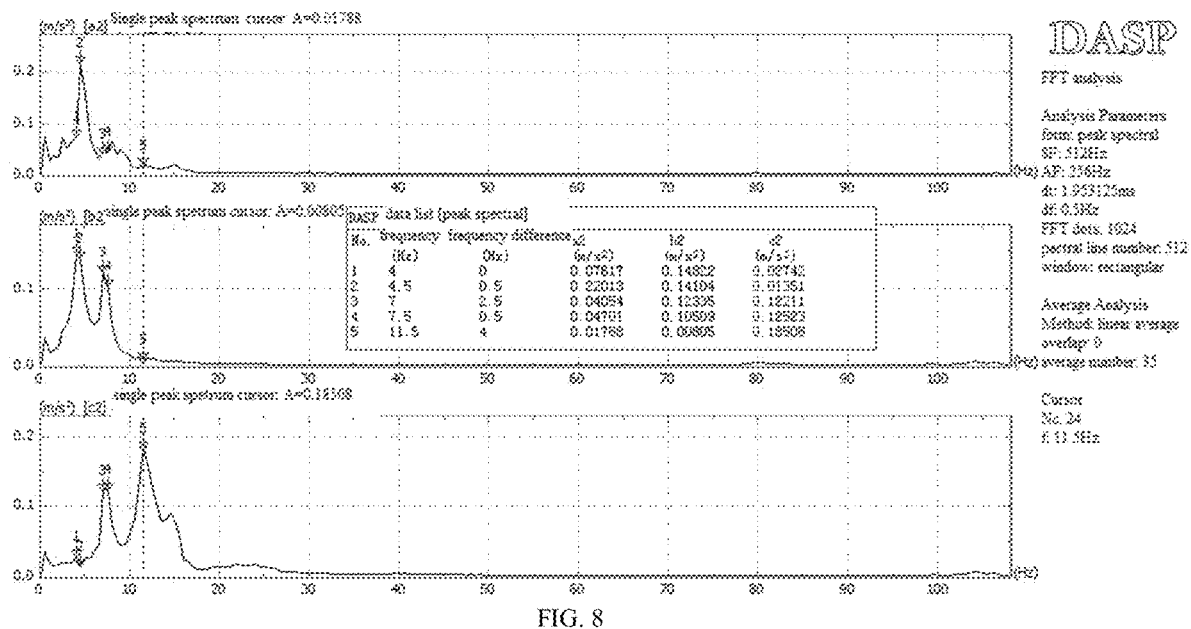

In the test, a cloud intelligent data acquisition analyzer (INV3062C1) and an ultra-low frequency acceleration vibration pickup (941B) are used. Through its own DASP intelligent data acquisition and signal analysis system, it can be concluded that the environmental excitation under this working condition is as shown in FIG. 8. As can be seen from the figure, the sampling frequency of the experiment is designed by adopting the Nyquist sampling theorem, the number of FFT points is 1024, the number of spectral lines is 512, the first-order peak of external excitation in the X direction is 4.5 Hz, the first-order peak in the Y direction is 4 Hz, and the first-order peak in the Z direction is 11.5 Hz.

Therefore, the excitation frequency distribution of the excitation sources in the environment can be known. The environmental excitation in the X/Y/Z directions is of low frequency, and the rubber vibration-proof gel pads can be used for isolating the excitation, so that the rigidity can be easily realized in the three directions. The support 64 is provided with a metal guide rod, so that its horizontal stability can be ensured. When the system structure is designed, it needs to be ensured that the natural frequency of the system for each degree of freedom does not equal to its corresponding excitation frequency, so as to avoid resonance, and the residual vibration can be damped through the support 64.

Analysis of Vibration Isolation Design for Internal Excitation

The internal excitation is mainly in the body 62. The imaging module 10 is mounted on the upper plate 71 and as a whole, there's no other internal interaction inside the imaging module except for the vibration caused by the rotation of the cooling fan of camera, and thus the internal excitation can be ignored; the axis Z as a movement mechanism can drive the objective lens to allow it to be in a focus tracking state all the time when in operation, the moving distance of the objective lens can be adjusted based on the evenness of the flowcell during focus tracking, and the excitation generated is relatively small because the objective lens is relatively light and the acceleration is small.

Figure 9:
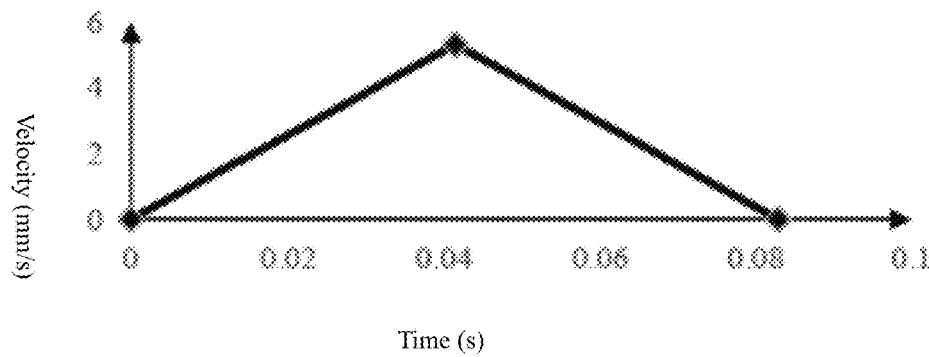

The two-dimensional micro-movement platform provides movement in XY two-dimensional directions for the flowcell, and can provide enough field of view for the objective lens to enable it to cover the test area of the whole flowcell. A single-molecule fluorescence signal is fragile, and long exposure can cause fluorescence to be rapidly quenched, and therefore the micro-movement platform is required to respond quickly. However, movement featuring high speed and sudden stop will bring movement excitation to the entire system. This part of excitation acts within the platform and causes mutual vibration inside it. During normal operation, the two-dimensional micro-movement platform has the largest influence on the vibration, and therefore the movement mechanism of the platform is mainly analyzed; a velocity-time curve VT for moving one FOV is shown in FIG. 9.

The two-dimensional micro-movement platform follows an S-shaped curve in a channel, the movement distance between two FOVs is 0.22 mm, the maximum velocity is 12.8 mm/s, the maximum acceleration time is 0.1 s, and the converted acceleration a is 0.128 m/s2.

Figure 10:
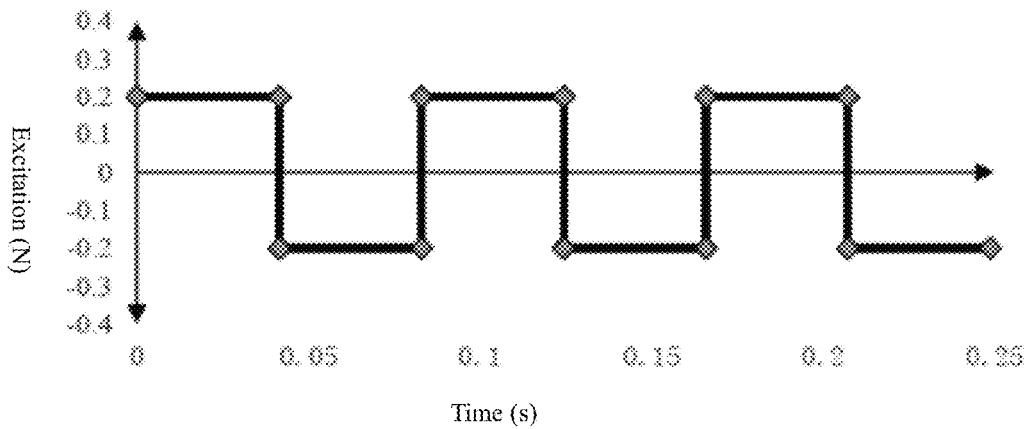

Considering the symmetry of the structure, forward movement in the X direction is regarded as a calculation target. Load of the micro-movement platform is measured to be about 2 kg, and it can be inferred from the movement trajectory that the excitation is a rectangular wave, as shown in FIG. 10.

Figure 11:
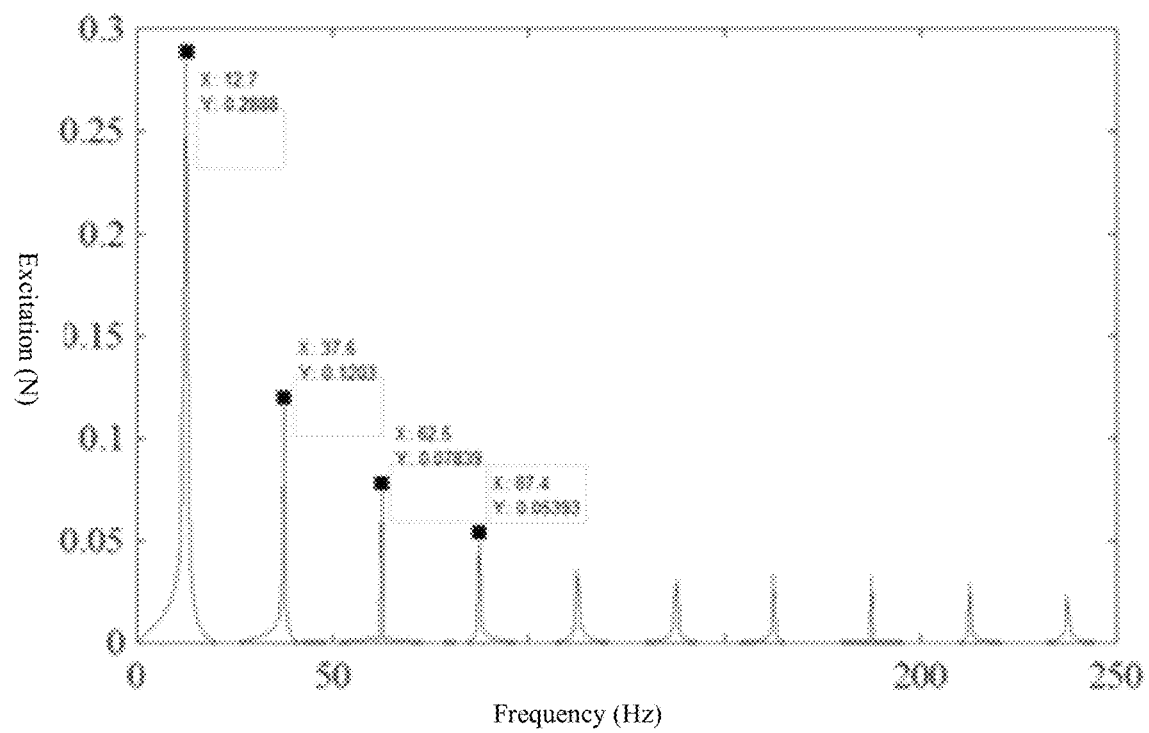

For the ease of subsequent modal analysis, the time domain signal needs to be converted into a frequency domain signal, and the conversion can be processed through matlab. According to the rectangular wave excitation obtained above, the time interval for the sampling of rectangular frame is 2 s, and the corresponding power spectral density curve can be obtained through standard function Fourier transform, as shown in FIG. 11.

The mass of the body 62 (Ms) is 50 kg, and FN1 is 0.2 N according to the calculation for movement excitation of the two-dimensional micro-movement platform. By analysis based on the above, the acceptable movement blur of the single-molecule gene sequencing system in the X/Y directions (ΔY) is less than or equal to 291 nm, namely Xs1 is less than or equal to 291 nm, and the corresponding natural frequency can be obtained according to the formula (3-20).

$$w_{s1} = \sqrt{\frac{F_{N1}}{M_s X_{s1}}} \geq \sqrt{\frac{0.2}{50^*291^*10^{-9}}} \text{ Hz} \approx 117 \text{ Hz} \quad (3\text{-}21)$$

Similarly, it is known that the load of the Z-axis movement platform is 300 g, and according to relevant data of the Z-axis movement platform, its maximum velocity is 12.8 mm/s and its maximum acceleration time is 0.2 s. Thus, the acceleration a is 0.064 m/s2, which is converted into Z-axis movement excitation FN2 (0.0192 N), and the maximum acceptable displacement of the single-molecular gene sequencing system in the Z direction (Xs2) is less than or equal to 400 nm according to analysis of the depth of field of the objective lens, and the corresponding natural frequency can be obtained according to the formula (3-20).

$$w_{s2} = \sqrt{\frac{F_{N2}}{M_s X_{s2}}} \geq \sqrt{\frac{0.0192}{50^*400^*10^{-9}}} \text{ Hz} \approx 31 \text{ Hz} \quad (3\text{-}22)$$

Therefore, according to the analysis result, if a proper vibration isolation effect for the internal excitation is desired, it is necessary that the first-order natural frequency of the body 62 in the X/Y directions is much greater than 117 Hz, and a very good vibration isolation effect can be achieved in the case of 165 Hz or more. The first-order natural frequency of the body 62 in the Z direction is far greater than 31 Hz, and a good vibration isolation effect can be achieved in the case of 44 Hz or more. To sum up, when the natural frequency of the main body 62 is greater than or equal to $\sqrt{2}$ times the internal excitation frequency, a better vibration isolation effect can be achieved, that is, the natural frequency of the main body 62 is greater than or equal to $\sqrt{2}$ times the internal excitation frequency along each of the X, Y and Z directions.

Evaluating whether the carrier module 100 vibrates using images:

Specifically, a group of dynamically photographed images are used to record information about fluorescent dots, the current state of the two-dimensional micro-movement platform is determined according to the resolution of the information about the fluorescent dots, and the movement trajectory of the micro-movement platform is matched. Without considering the time line of the movement process, the influence is determined to be caused by vibration focus tracking if the image remains blurred.

A certain movement trajectory is set for the two-dimensional micro-movement platform in software, so that the two-dimensional micro-movement platform drives the reaction device 200 to move along a set target trajectory according to certain acceleration, frequency and path. In order to distinguish between vibration states conveniently and amplify a boundary between vibration and stillness, the two-dimensional micro-movement platform stops for a period of time after moving by one FOV to allow it to be fully stopped and stabilized.

In order to ensure the accuracy of the process, the times of repetition of the experiment are generally increased; meanwhile, the camera photographs continuously according to a recordable minimum exposure time to continuously record the state of the images during the process of start to stop of the two-dimensional movement platform, and images dynamically photographed are output to record the information about the fluorescence dots.

Figure 12:
FIGS. 12-24 are drawings related to evaluating whether a carrier module vibrates using an image according to an embodiment of the present application.

In this process, the objective lens moves in an S-shaped curve in a channel relative to the reaction device 200, and covers 2×50 FOVs, and the partial trajectory chart is shown in FIG. 12. As the lens makes a round trip, two rows of FOVs are involved, with 50 FOVs in each row. The distance between two FOVs is 0.22 mm, the acceleration a is 0.128 m/s$^2$, and the retention time for each FOV is 1 s.

After the software setting is completed, a qualified reaction device 200 is prepared, and the dot shape and density are ensured to meet the requirements. The reaction device 200 is placed on the carrier module 100 and clamped well and coated with corresponding lens oil, and it needs to be sure that no bubbles are present in the process. The two-dimensional micro-movement platform is moved to allow the objective lens to be in a specified channel. 532 nm laser is started, and a proper focal plane is found manually, so that fluorescent dots in an FOV are in the clearest state. Then the focal plane is made fixed for subsequent automatic focus tracking. The exposure time of the camera is set to 30 ms, and then the test is started, and a group of 3000 pictures can be output after the photographing is finished. The same experiment was performed on three sequencing systems 300 of embodiments 1-3, so that multiple groups of experimental results can be obtained.

Image Processing Scheme

Although it is known that the image definition can be evaluated by calculating the image sharpness, there are tens of thousands of fluorescent molecules in an image window, and both desired information points and background noise caused by various impurities are present. Therefore, image processing is needed to denoise and refine the image and to output a desired overall sharpness value, and this part can be realized by programming in C++ language.

(1) Image acquisition: when the reaction device 200 is used for carrying out experimental tests in a built instrument, a series of images can be obtained, and the software acquires image information from a specified folder and imports the image information into a program.

(2) Image denoising: it refers to a measure to denoise and enhance continuously acquired images.

The dots (spots/signal dots) in one FOV image are as dense as stars and are in tens of thousands, and the dots are different in brightness and are mingled with interference such as adsorption and background noise. Therefore, generally, it is first necessary to eliminate the interference and find spots that meet requirements. The image denoising method used in this embodiment is mainly for the purpose of removing the background influence in the image. For the calculation of the image background, the morphological opening operation in the image processing is used in the experiment, and the result of the image opening operation is regarded as the image background. A denoised image is obtained by subtracting the calculated background image from the original image.

(3) Signal locating: this is for locating all point light source signals in the image.

Figure 13:
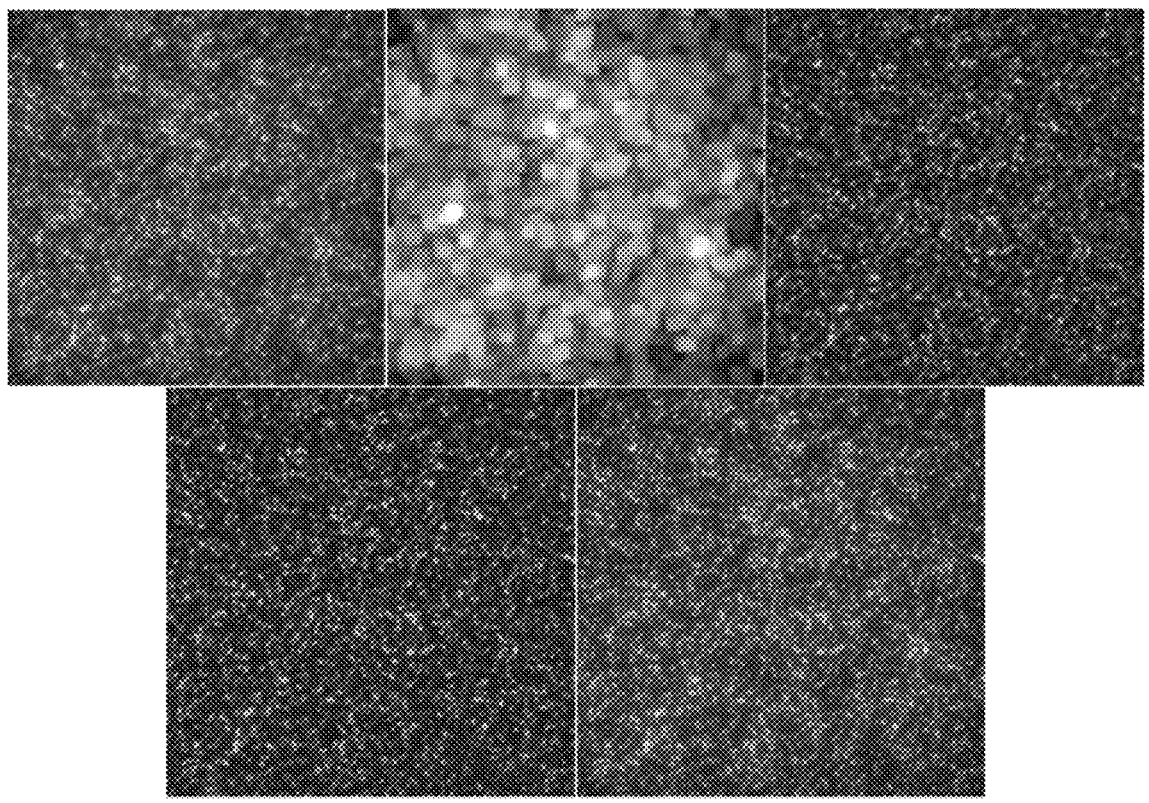

Locating each signal point in the image needs to be firstly based on the imaging characteristic of the signal points. The gray values of the signal points are in Gaussian distribution, and values at the central area are greater than those at the edge area. Almost positions of all signal points in the image can be found using the above characteristic, but many noise points are also located at the same time. In order to filter out the influence of noise points, further screening of candidate points found in the previous step is required. Specifically, the confidence of each signal point is determined according to the information such as the signal-to-noise ratio of each signal point position, and the distribution of imaging gray values, so that the signal points with low confidence are filtered out. FIG. 13 shows, from left to right and from top to bottom, the original image (acquired image), the background image, the denoised image, the image with the signal points and the noise points located and the image with the signal points with low confidence filtered out as described above.

(4) Sharpness calculating: the sharpness value of each point light source signal is calculated, and a representative sharpness value of point light source is selected as the definition value of the image to be output.

After each signal point is located, the sharpness value of each signal point in the image needs to be calculated, so that the sharpness value of the image can be further determined. The sharpness value of each signal point can be calculated according to the following steps: a. fitting an intensity value on the central position of the signal point according to the intensity distribution of the area near the center of the signal point; b. calculating the interpolation average of the intensity value at the central position and the intensity values of the adjacent regions as the sharpness value of the signal point, wherein the difference of the light source center to 8 adjacent regions at the edge area is calculated, and then the difference is divided by average gray value of a 3×3 region, and the calculation can be carried out according to the formula (5-1).

Score=9×(8Center−edge[8])/(Center+edge[8])    (5-1), where Score represents sharpness value of the image; center represents the intensity value of the center; edge[8] refers to intensity values of 8 adjacent regions at the edge of the light source.

According to the above steps, the sharpness values (Scores) of all signal points can be calculated. The Scores of all the points are sorted in ascending order, and the Score at the 90th quantile is taken as the definition value ImageScore to evaluate the definition of the whole image. Definition values for a set of sample images are obtained using the above method, as shown in FIG. 14.

The reason for selecting the Score at the 90th quantile is that the randomness of the luminescence of a single molecular point is high, and interference such as impurity noise points possibly exists in the central calculation region; in order to avoid the interference of the noise points which are not completely filtered out in the signal point locating process, the 90th quantile of the sharpness values of all the signal points is selected as the sharpness value ImageScore of the image. It would be appreciated that values corresponding to other quantiles may also be selected as sharpness values of the image. FIG. 14 shows a set of sample images with different definition values, which are, from left to right and top to bottom, images with ImageScore values of 0, 1.49, 2.03, 2.51 and 3.01, respectively.

Figure 14:
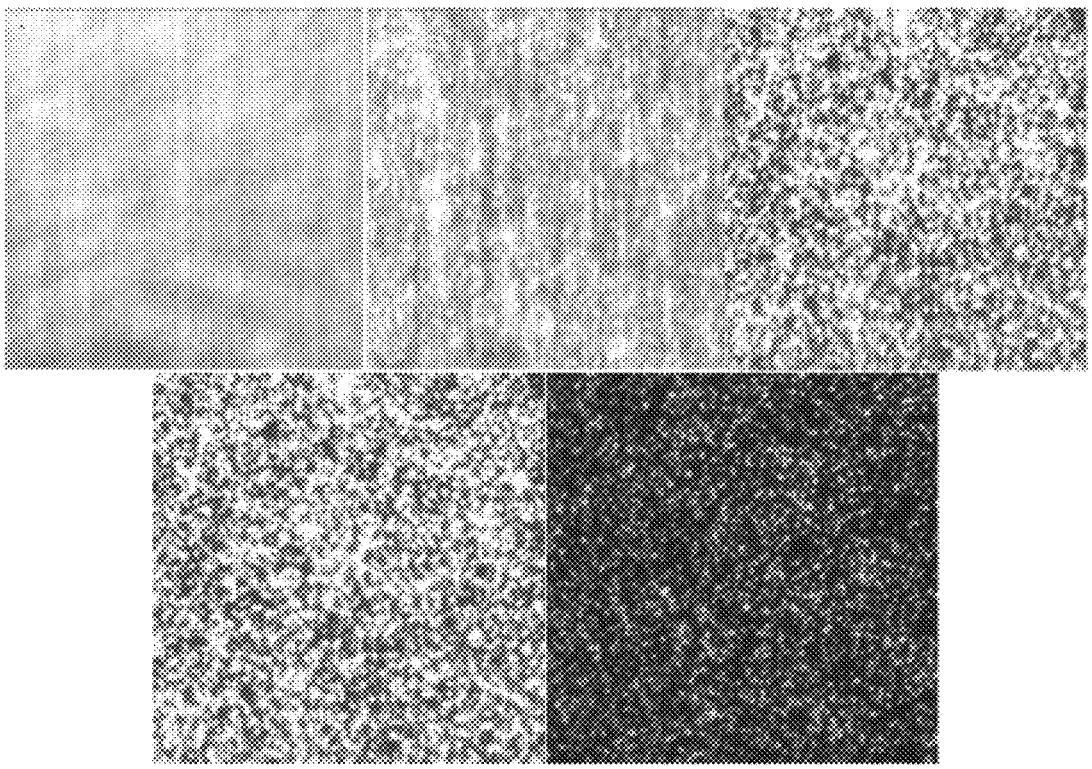

As can be seen from FIG. 14, ImageScore is an image evaluation index, and the higher the value is, the clearer the corresponding image is. In general, dots in a picture of 2.0 or more are relatively clear, while a picture is blurred below 1.5. The ImageScore can accurately determines the definition of an image, and can be used for evaluating whether the platform vibrates after reaching a specified position.

(5) In data processing, the ImageScore value obtained in the last step is output to a specified file for subsequent evaluation.

Data Processing Scheme

Figure 15:
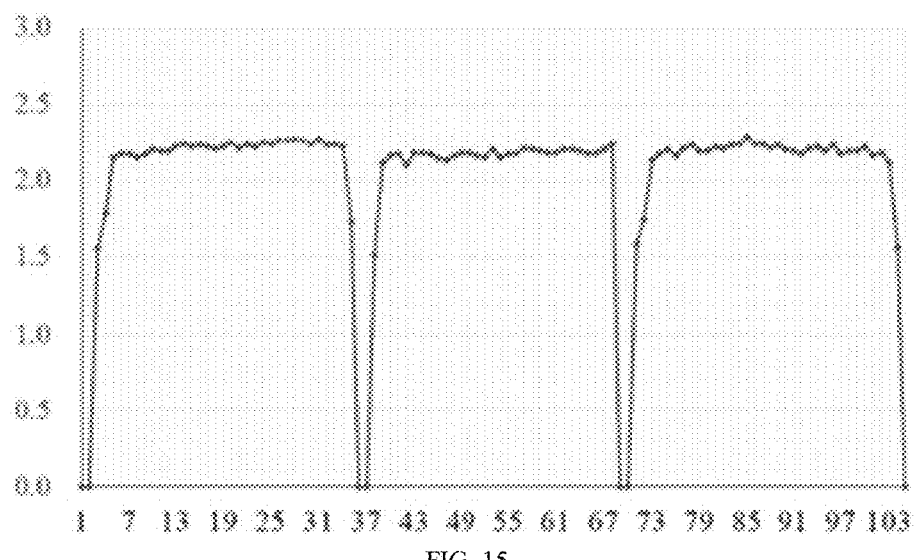

A stack of images output in the test are processed, an ImageScore value is obtained for each image. It can be found from a curve plotted with the ImageScore values that the values show periodical change, and two periods are cut out, as shown in FIG. 15, wherein the abscissa represents the number of the images, and the ordinate represents the ImageScore value corresponding to the image.

According to observation, it is found that the curve fluctuation and the movement of the two-dimensional micro-movement platform change periodically. The ImageScore value is rapidly reduced and is even 0 when the two-dimensional micro-movement platform starts to move; during the process from the platform's start of stopping to its stabilization, the corresponding ImageScore value is gradually increased; when the platform stabilizes, the corresponding ImageScore value will be a maximum one in the process of becoming stabilized.

According to the rule, the FOV with a sharply decreased ImageScore value can be found first, and the FOV corresponds to the starting point of the movement of the two-dimensional micro-movement platform. Then, based on this FOV, a previous FOV of an FOV where ImageScore value starts to become stabilized is found. Since the ImageScore of stable state is also a fluctuating value, this fluctuating condition needs to be avoided in criterion for determining points before stabilization; if the difference between the ImageScore values of two consecutive points after a point is not greater than 0.3, the point is the required FOV. Then, according to this criterion, the number of FOVs needed from start of moving to becoming stabilized (Nw) is counted. This process can be done by importing the ImageScore data into Matlab and then programming.

The exposure time of the camera is 30 ms, which means that the time consumed by each point is 30 ms, and then the exposure time is multiplied by the number of FOVs required for becoming stabilized (Nw) counted above, thus obtaining the time required by the two-dimensional micro-movement platform from the start of moving to becoming stabilized.

Since the minimum image acquisition exposure time for this camera is 30 ms, its corresponding resolution is as such. During testing, the starting time of each movement of the two-dimensional micro-movement platform and that of the exposure of the camera cannot be guaranteed to be the same, and the real situation is that in most cases they are in a mismatched state, namely the two-dimensional micro-movement platform may not start until the camera is in the 30 ms of exposure. Therefore, delay in exposure mismatch needs to be considered when the time of becoming stabilized Tw and the time of real movement of the two-dimensional micro-movement platform are compared. The time Ts required by the two-dimensional micro-movement platform from start of movement to the end in each period is about 90 ms, and in view of the delay in exposure mismatch, the comparison time Td required by the two-dimensional micro-movement platform from start of movement to the end in each period is Ts±30 ms, namely 60-120 ms.

Analysis of Results

On the premise that the experimental conditions are the same, three sequencing systems 300 comprising the vibration damping structures 60 of embodiments 1-3, respectively, are subjected to the same experimental test for multiple times, so that multiple sets of experimental data results can be obtained. The comparison of the experimental data shows that the tendency of results of all the instruments is consistent, demonstrating the success in the repeatability verification. The results of each sequencer are analyzed below independently.

Analysis of Experimental Results of Vibration Damping Structure 60 of Embodiment 1

Figure 16:
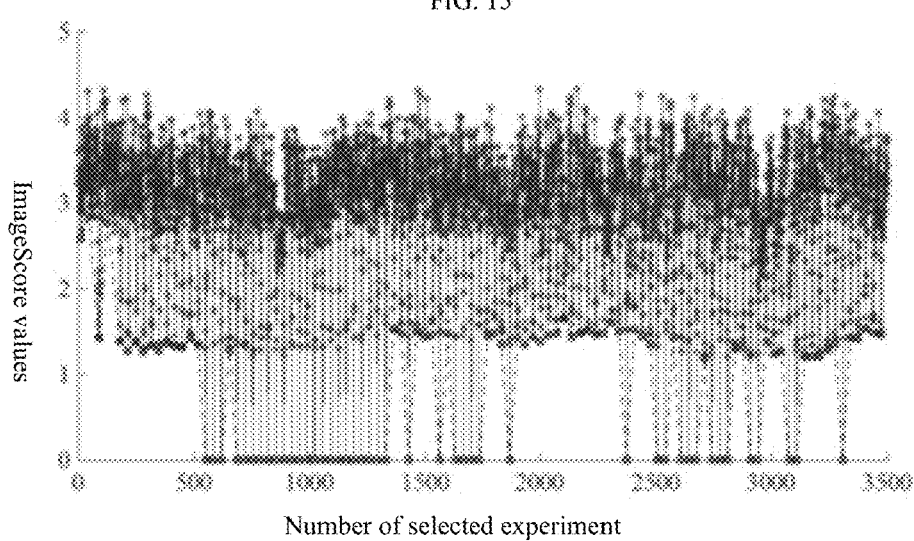

A plurality of experiments are performed according to the steps described above, and one experiment is selected, and the curve of ImageScore values corresponding to the selected experiment can be obtained through data processing, as shown in FIG. 16. As shown in the curve, the ImageScore values also show periodical change, but they are always in an unstable fluctuation state, which shows that the structure is sensitive to vibration and relatively weak in vibration damping.

Figure 17:
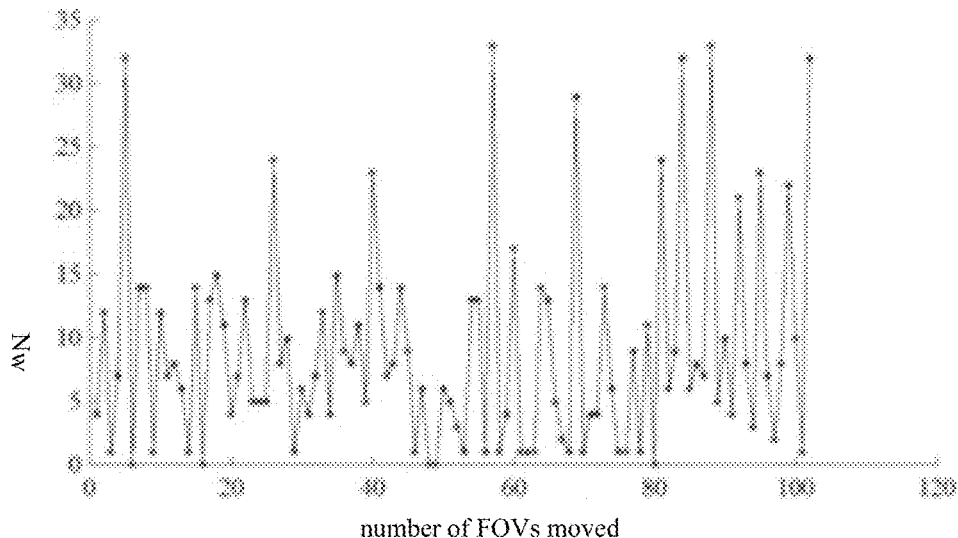
Figure 18:
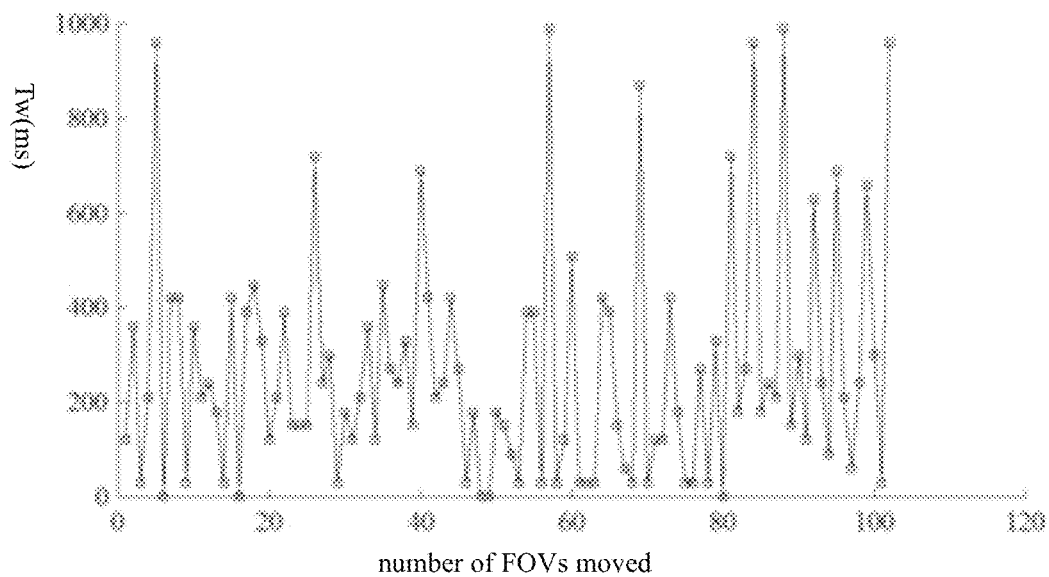

Through matlab processing, the number of FOVs required for becoming stabilized (Nw) can be obtained, and an output curve is shown in FIG. 17, wherein the abscissa represents the number of the FOVs moved, and the ordinate represents the Nw (number of images/FOVs required for stabilization). Then, a graph of the time for becoming stabilized (Tw) can be obtained, as shown in FIG. 18.

From the figure, it can be found that the Tw (time for becoming stabilized) fluctuates greatly in the whole process, from as short as 60 ms to as long as 990 ms, and the calculated average value is 270 ms, which is far greater than the comparison time Td (60-120 ms) required by the two-dimensional micro-motion platform from the start of movement to the end.

Therefore, it can be determined that the sequencing system 300 comprising the vibration damping structure 60 of embodiment 1 needs a long time to recover focus tracking stability after the two-dimensional micro-movement platform is in place, and as can be seen from the curve of the ImageScore values, the amplitude value of the ImageScore value changes greatly when the ImageScore value is in a stable state, which indicates that the instrument is always in a relatively unstable state, is susceptible to outside interference, and cannot well meet the requirement for vibration suppression.

Analysis of Experimental Results of Vibration Damping Structure 60 of Embodiment 2

Figure 19:
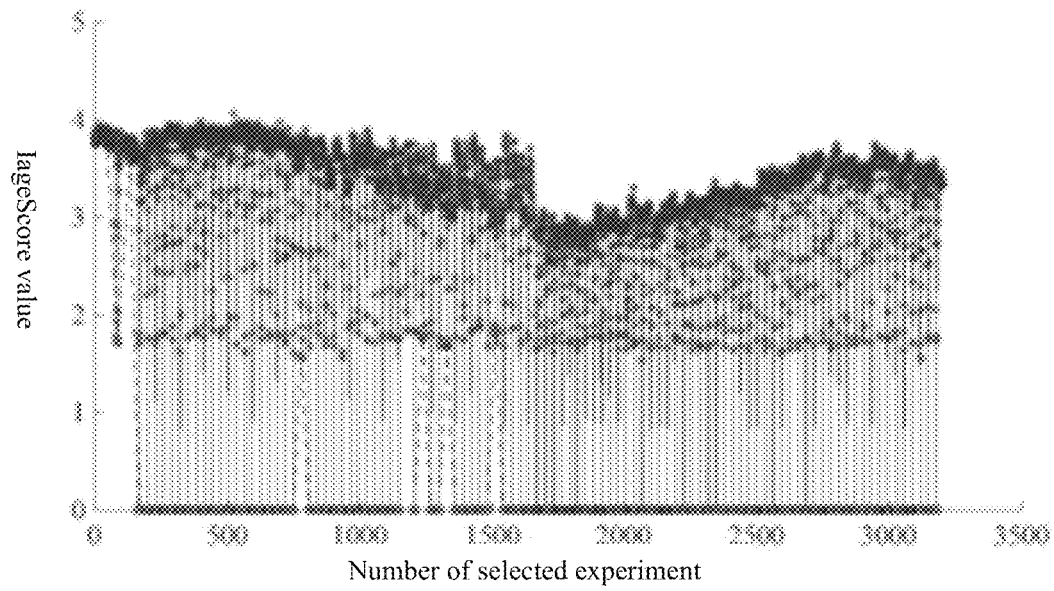

Similarly, a plurality of experiments are performed according to the steps described above, and one experiment is selected, and the curve of ImageScore values of the selected experiment can be obtained through data processing, as shown in FIG. 19.

The tail part at the start of the curve is caused by the asynchronous start times of the two-dimensional micro-movement platform and photographing. However, the data processing result is not affected. As can be seen from the figure, the first four extreme points are all obtained before the two-dimensional micro-movement platform has not formally moved, so that the subsequent statistics can exclude the first four cycles. According to observation of the figure, it can be found that the curve of ImageScore values is more regular than the former group, and the fluctuation value in the stable state is smaller than that of the former group.

Figure 20:
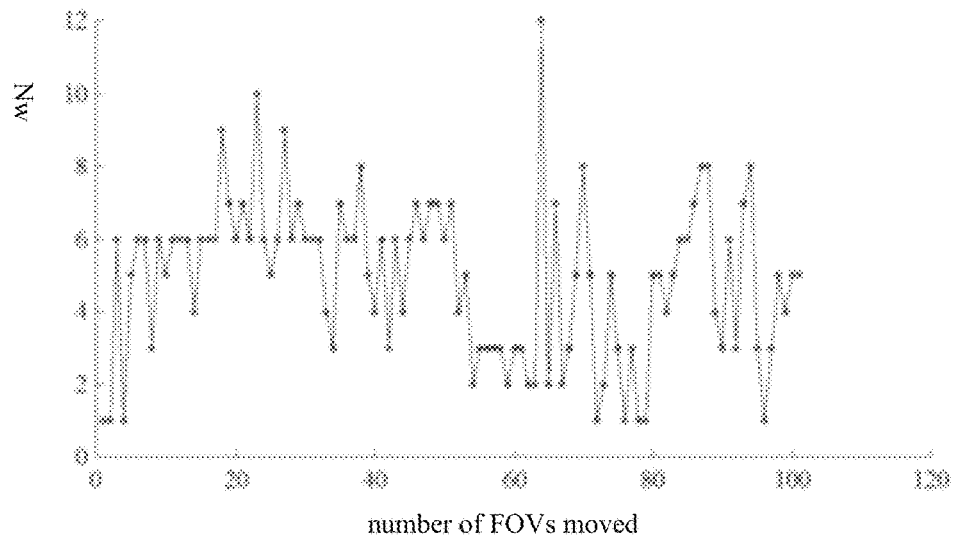
Figure 21:
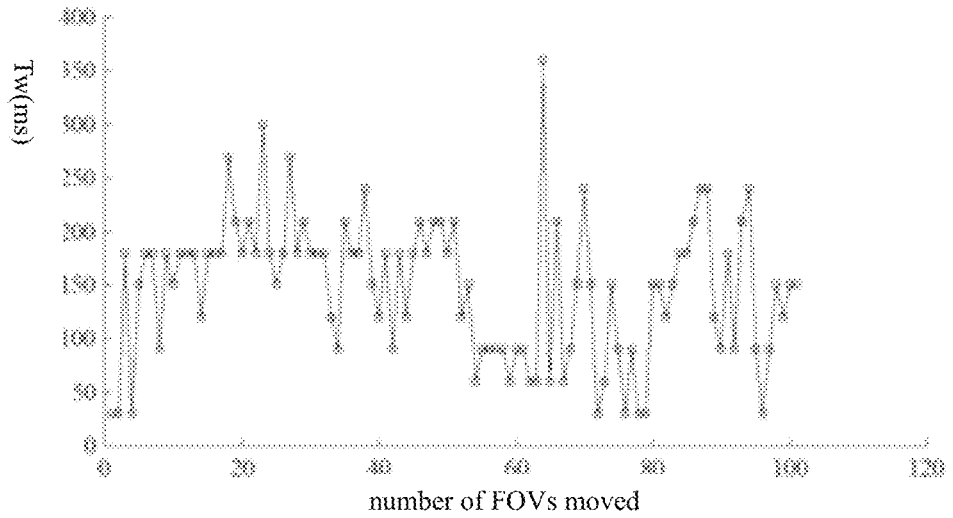

Through matlab processing, the Nw (number of FOVs required for becoming stabilized) is obtained, as shown in FIG. 20. Consistent with the conclusion for the curve of ImageScore values described above, the data of the first four cycles may not be included in statistics. Then, a graph of the Tw (time for becoming stabilized) can be obtained, as shown in FIG. 21.

From the figure, it can be found that except for the first four cycles, the Tw (time for becoming stabilized) fluctuates greatly for the subsequent 97 cycles, from as short as 60 ms to as long as 360 ms, and the calculated average value is 151 ms, which is greater than the comparison time Td (60-120 ms) required by the two-dimensional micro-movement platform from the start of movement to the end. Therefore, it can be determined that the sequencing system 300 comprising the vibration damping structure 60 of embodiment 2 needs more than 30 milliseconds to recover the focus tracking stability after the two-dimensional micro-movement platform is in place. According to the comparison between the curves of ImageScore, the vibration damping structure 60 of embodiment 2 is more stable and further suppresses vibrations compared to the sequencing system 300 comprising the vibration damping structure 60 of embodiment 1.

Analysis of Experimental Results of Vibration Damping Structure 60 of Embodiment 3

Figure 22:
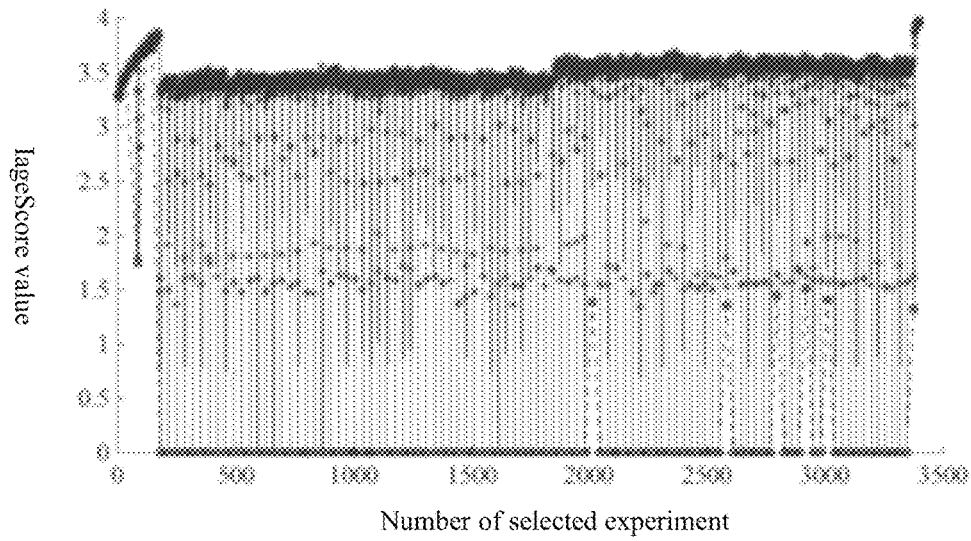

A plurality of experiments are performed according to the steps described above, and one experiment is selected, and the curve of ImageScore values of the selected experiment can be obtained through data processing, as shown in FIG. 22.

The tail parts at the start and the end of the curve are caused by the asynchronous start times of the two-dimensional micro-movement platform and photographing. However, the data processing result is not affected. As can be seen from the figure, the first five extreme points are all obtained before the two-dimensional micro-movement platform has not formally moved, so that the subsequent statistics can exclude the first five cycles.

Figure 23:
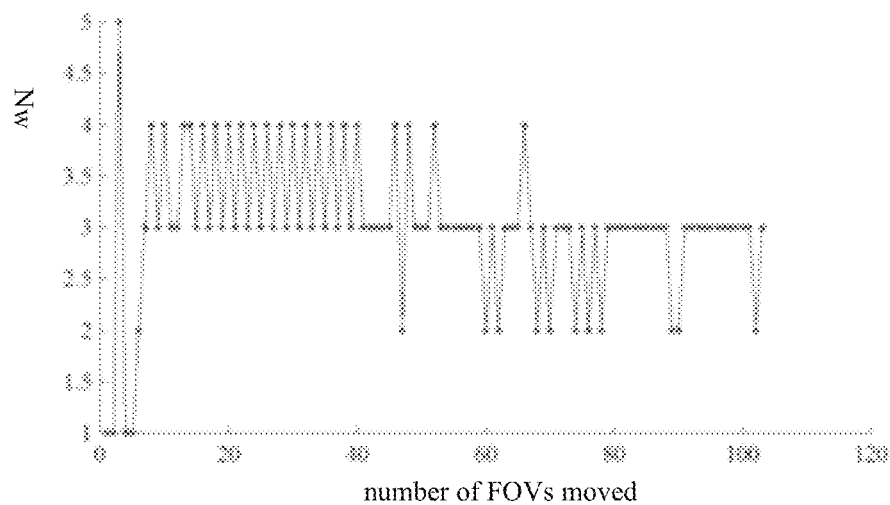
Figure 24:
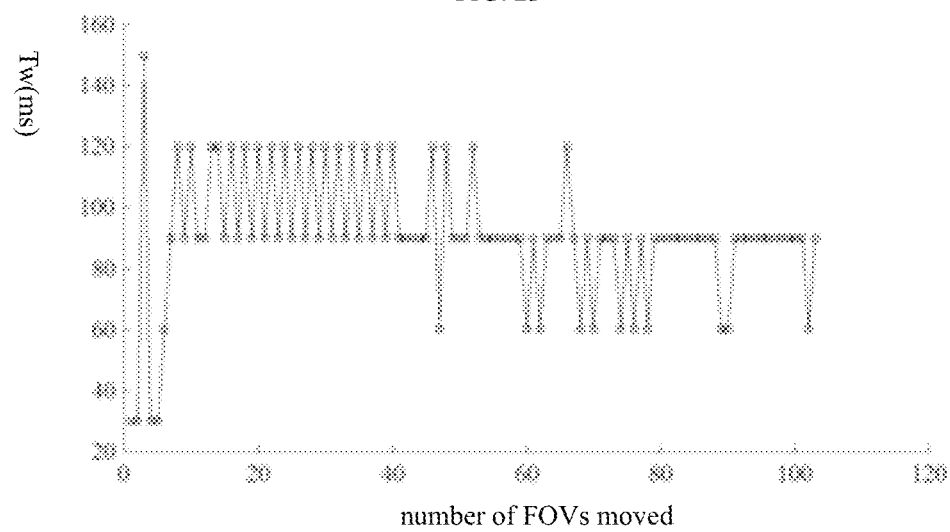

Through matlab processing, the Nw (number of FOVs required for becoming stabilized) is obtained, as shown in FIG. 23. Consistent with the conclusion for the curve of ImageScore values described above, the data of the first five cycles may not be included in statistics. Then, a graph of the Tw (time for becoming stabilized) can be obtained, as shown in FIG. 24.

From the figure, it can be found that except for the first five cycles, the Tw (time for becoming stabilized) is between 60 ms to 120 ms for the subsequent 98 cycles, and the average value is 92.8 ms. Therefore, it can be determined that almost no image blurring caused by vibration is found for the single-molecule gene sequencing system 300 comprising the vibration damping structure 60 of embodiment 3 after the two-dimensional micro-movement platform is in place, and the requirement for vibration suppression is further met.

Figure 6:
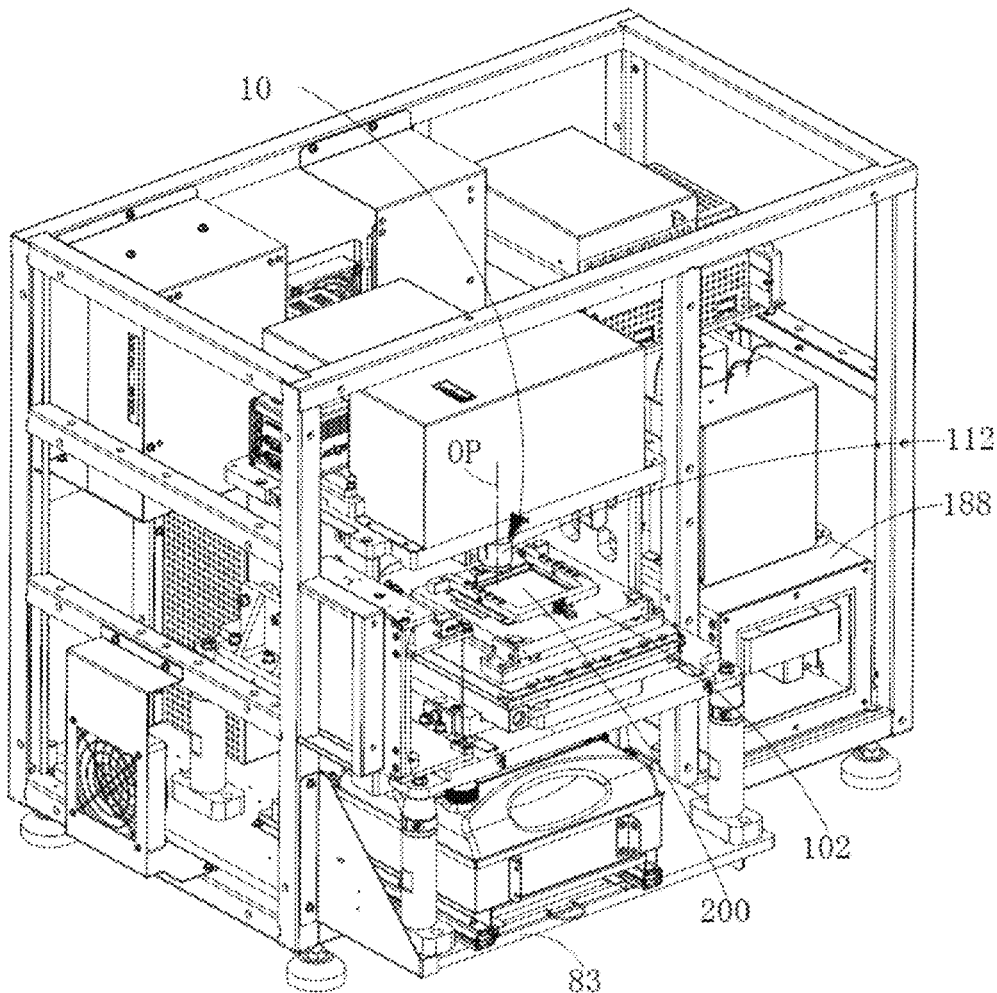
FIG. 6 is a structural schematic view of a sequencing system according to an embodiment of the present application.

As shown in FIG. 6, a sequencing system 300 provided in an embodiment of the present application comprises the vibration damping structure 60 according to any of the above embodiments. In the illustrated embodiment, the vibration damping structure 60 in the sequencing system 300 is the vibration damping structure 60 of embodiment 3. It would be appreciated that in other embodiments, the sequencing system 300 may also comprise the vibration damping structure 60 of any of embodiments 1-2.

Figure 25:
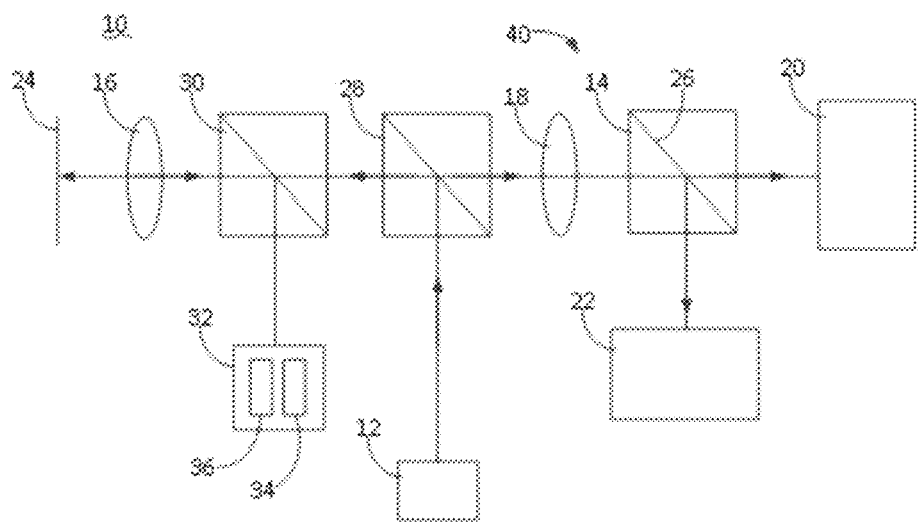
FIG. 25 is a structural schematic view of an imaging module according to an embodiment of the present application.

As shown in FIG. 25, an imaging module 10 according to an embodiment of the present application comprises a first light source 12, a first lens 16 and a light splitting module 40, wherein the light splitting module 40 comprises a first splitter 14, a second lens 18, a first camera 20 and a second camera 22. The first lens 16 is configured to receive a first light beam from the first light source 12 and allow the light beam to be incident on a sample 24 after being collimated, and to receive a light beam from the sample 24 and collimate the light beam. The second lens 18 is configured to focus the collimated light beam from the first lens 16 to the first camera 20 and the second camera 22. The first splitter 14 is configured to split the focused light beam from the second lens 18 into a second light beam and a third light beam. The first camera 20 is configured to receive the second light beam. The second camera 22 is configured to receive the third light beam. The imaging module 10 of the present embodiment can be applied to any of embodiments 1-3 of the vibration damping structure 60 described above.

In the imaging module 10 above, the second lens 18 focuses light, and then the first splitter 14 splits the light into the second light beam and the third light beam, so that the use of optical elements can be reduced, the length of splitting optical path is short, and thus the length of total optical path of the imaging module 10 is shortened, which is beneficial to miniaturization of the imaging module 10 and industrialization.

Specifically, the sample 24 can be a target nucleic acid sample, which can be placed in a reaction device 200, such as a flowcell. The first light source 12 may be a laser light source. In one example, the flowcell comprises a substrate with channels and glass provided thereon. When the sequencing system 300 is used for sequencing, under certain conditions, a target nucleic acid, an enzyme, a fluorescently-labeled nucleotide reagent or solution, etc., are mixed in the channels to react; then the first light source 12 emits laser, and the laser is incident on a specific FOV of the flowcell via the first lens 16 and excites fluorophores in the FOV to emit fluorescence; the fluorescence is focused by the first lens 16 and the second lens 18 to the first splitter 14, and the first splitter 14 splits the focused fluorescence beam into a second light beam and a third light beam; the first camera 20 receives the second light beam, and the second camera 22 receives the third beam to acquire a first image and a second image of the FOV, respectively.

Figure 26:
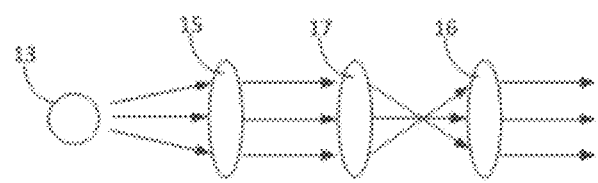
FIG. 26 is a structural schematic view of a first light source according to an embodiment of the present application.

In an example, referring to FIG. 26, the first light source 12 may comprise a first light emitter 13 and a third lens 15. The first light beam is a collimated light beam formed when a light beam emitted from the first light emitter 13 passes through the third lens 15, and the first light beam is focused on a back focal plane of the first lens 16 by a fourth lens 17 and then is incident on the sample 24 after being collimated by the first lens 16. In one example, the first light source 12 further comprises an optical fiber coupler, such as a single mode optical fiber coupler. Specifically, the imaging module 10 is a total internal reflection imaging module, and the collimated light beam (parallel light beam) passing through the first lens 16 is incident on the surface of the flowcell at an angle larger than the critical angle to cause total internal reflection, and an evanescent field (evanescent wave) is generated at a lower surface of the glass of the flowcell. Fluorescence emitted by the excited fluorescent molecules in the evanescent field is received by the first lens 16.

When a light beam emitted by the first light source 16 excites fluorophores of the sample 24 to emit light, a light beam received by the first lens 16 from the sample 24 is the light beam emitted by the sample 24.

Image sensors of the first camera 20 and the second camera 22 may be a CCD or a CMOS. Preferably, the image sensors of the first camera 20 and the second camera 22 are of the same type, e.g., both CCD or both CMOS. The first splitter 14 may be a dichroic mirror.

The second light beam is a transmitted beam of the first splitter 14, and the third light beam is a reflected beam of the first splitter 14.

Figure 27:
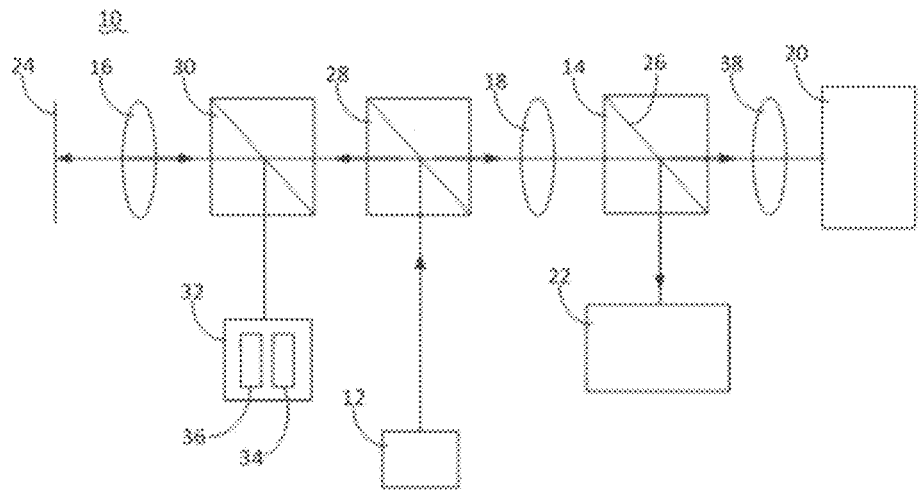
FIG. 27 is another structural schematic view of an imaging module according to an embodiment of the present application.

In some embodiments, the first camera 20 and the second camera 22 are positioned at an angle of 90 degrees or 270 degrees relative to each other. Thus, the first camera 20 and the second camera 22 can be configured into the imaging module 10 within a limited space. Specifically, in the orientation shown in FIG. 25, the first splitter 14 has a first reflection surface 26, and an included angle between the first reflection surface 26 and a horizontal plane is 45 degrees. One part of the light beam incident on the first reflection surface 26 in a horizontal direction is reflected and turned by 90 degrees to reach the second camera 22, and another part of the light beam incident on the first reflection surface 26 in the horizontal direction passes through the first reflection surface 26 and is incident on the first camera 20. In FIGS. 25 and 27, the first camera 20 and the second camera 22 are positioned relative to each other at an angle of 90 degrees in a clockwise direction and at an angle of 270 degrees in a counterclockwise direction. In one example, the sample is provided with two fluorescent labels, such as Cy3 and Atto647N, with emission bands of 550-620 nm and 650-750 nm, respectively (peaks at about 564 nm and 670 nm, respectively). The first splitter 14 is a dichroic mirror having a high transmittance for light of wavelength 550-620 nm and a high reflectance for light of wavelength above 650 nm.

The nucleotide reagents with fluorescent labels include A, T, C and G nucleotide reagents, and different nucleotide reagents can be placed in different containers. In one example, four nucleotides carry the same fluorescent label, and each cycle of sequencing comprises four base extensions during DNA sequencing, wherein the four base extensions refer to adding the four nucleotides, respectively, and obtaining corresponding images.

In one example, four nucleotides are in pairs of two and are provided with a first fluorescent label and a second fluorescent label, respectively, and the first fluorescent label and the second fluorescent label can be excited to emit different fluorescence. Two-color sequencing is performed by using the four nucleotides, and each cycle of sequencing comprises two base extensions. When sequencing is performed by using a sequencing system 300 comprising the imaging module 10, under certain conditions, a target nucleic acid, an enzyme, two nucleotide reagents or solutions with the first fluorescent label and the second fluorescent label, respectively, etc., are mixed in channels to react, the first light source 12 simultaneously emits a first laser and a second laser to be incident to a specific FOV of the flowcell via the first lens 16, and the first fluorescent label and the second fluorescent label in the FOV are excited by the first laser and the second laser, respectively, to emit a first fluorescent and a second fluorescence, respectively. The first fluorescence and the second fluorescence are converged to the first splitter 14 (a dichroic mirror) through the first lens 16 and the second lens 18, and the dichroic mirror separates the converged first and second fluorescence. The first fluorescence is focused onto an image plane of the first camera 20, and the second fluorescence is focused onto an image plane of the second camera 22, thereby obtaining a first image and a second image of the FOV formed by the first fluorescence and the second fluorescence, respectively. Base calling/sequencing is realized based on the sequence of adding nucleotides and the information of the first image and the second image in different cycles of sequencing.

In another example, four nucleotides contain fluorescent label a, fluorescent label b, dual fluorescent label a-b and no label, respectively, and the fluorescent label a and the fluorescent label b can be excited to emit different fluorescence. Four-color sequencing is performed by using the four nucleotides, and each cycle of sequencing comprises a base extension. When sequencing is performed by using a sequencing system 300 comprising the imaging module 10, under certain conditions, a target nucleic acid, an enzyme, the above four nucleotide reagents or solutions, etc., are mixed in channels to react, the first light source 12 simultaneously emits a first laser and a second laser to be incident to a specific FOV of the flowcell via the first lens 16, and the fluorescent labels in the FOV are excited by the first laser and the second laser, respectively, to emit fluorescence. The fluorescence is converged to the first splitter 14 (a dichroic mirror) through the first lens 16 and the second lens 18, and the dichroic mirror divides the fluorescence into fluorescence from the fluorescent label a and fluorescence from the fluorescent label b. The fluorescence from the fluorescent label a is focused onto an image plane of the first camera 20, and the fluorescence from the fluorescent label b is focused onto an image plane of the second camera 22, thereby obtaining a first image and a second image of the FOV, respectively. Base calling/sequencing is realized based on the information of the first images and the second images of different cycles of sequencing and the information of the first images and the second images of the same cycle of sequencing.

In some embodiments, the first lens 16 comprises one or more lenses, and the second lens 18 comprises one or more lenses. Specifically, in the microscope system, the one or more lenses of the first lens 16 constitute an objective lens, and the one or more lenses of the second lens 18 constitute a tube lens. In other embodiments, the first lens 16 comprises one or more lenses, or the second lens 18 comprises one or more lenses.

In some embodiments, the imaging module 10 comprises a second splitter 28, and the second splitter 28 is configured to receive the first light beam from the first light source 12 and divert the first light beam to the first lens 16, such that the first light beam is merged into an optical path (an imaging optical path) in which an optical axis of the first lens is located. Thus, the arrangement of the second splitter 28 can allow the first light source 12 to be located outside the optical path in which the optical axis of the first lens 16 is located, so that the elements of the imaging module 10 can be compactly and reasonably arranged, which is beneficial to the miniaturization of the imaging module 10 and industrial application.

Specifically, the second splitter 28 is configured to deflect the first light beam by 90 degrees. Thus, it is convenient to arrange the position of the first light source 12, including the relative positions of the components it contains.

In some embodiments, the imaging module 10 comprises a third splitter 30 and an automatic focusing module 32. The automatic focusing module 32 is configured to emit a fourth light beam and to receive the fourth light beam reflected by the sample 24, and the third splitter 30 is configured to receive the fourth light beam and to divert the fourth light beam to the first lens 16, and is further configured to receive the fourth light beam reflected by the sample 24 and to divert the fourth light beam to the automatic focusing module 32. Thus, focusing may be achieved using the automatic focusing module 32, enabling image acquisition using the imaging module 10.

Specifically, the automatic focusing module 32 comprises a second light source 34 and a receiver 36. The second light source 34 is configured to emit the fourth light beam to the third splitter 30, and the receiver 36 is configured to receive the fourth light beam collimated by the first lens 16. In one example, the second light source 34 may be an infrared light source. The receiver 36 may be a photodiode. In focusing, the second light source 34 emits the fourth light beam, which is then diverted to the first lens 16 by the third splitter 30 and focused to the sample 24 by the first lens 16. The fourth light beam reflected by the sample 24 is incident to the third splitter 30 after being collimated by the first lens. At this time, by determining the change in the information of the fourth light beam reflected by the sample 24 and received by the receiver 36, the platform carrying the sample can be moved to allow the sample 24 to be closer to or away from the first lens 16, thereby achieving focusing.

In one example, the receiver 36 comprises a sensor, such as a two-dimensional PSD sensor, and the second light source 34 comprises an LED light source and a mask positioned in front of the LED light source; light emitted by the LED light source irradiates the mask to obtain a spot with a specific pattern, wherein the spot with the specific pattern is transferred to the first lens 16 through the third splitter 30 and then converged on the sample 24, and the spot reflected by the sample 24 finally reaches the sensor; the automatic focusing module 32 further comprises a signal processing module, wherein the sensor is connected to the signal processing module, through which the information of the spot is obtained. Further, the automatic focusing module 32 further comprises a signal output module for outputting change in the information of the spot, so that the platform carrying the sample drives the sample to move to an object plane of an imaging optical path (e.g., a fluorescence optical path).

Figure 28:
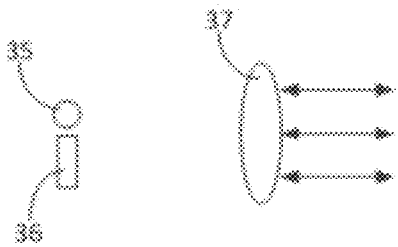
FIG. 28 is a structural schematic view of a second light source according to an embodiment of the present application.

In some embodiments, referring to FIG. 28, the second light source 34 comprises a second light emitter 35 and a fifth lens 37, wherein the fourth light beam is a collimated light beam formed when a light beam emitted from the second light emitter 38 passes through the fifth lens 37, and the fourth light beam reflected by the sample 24 is converged to the receiver 36 through the fifth lens 37.

In some embodiments, referring to FIG. 27, the second light beam is a light beam formed when a focused light beam from the second lens 18 transmits through the first splitter 14, and the imaging module 10 comprises a compensation lens 38, wherein the compensation lens 38 is located between the first splitter 14 and the first camera 20, and the compensation lens 38 is configured to compensate for astigmatism caused by the second light beam.

Figure 29:
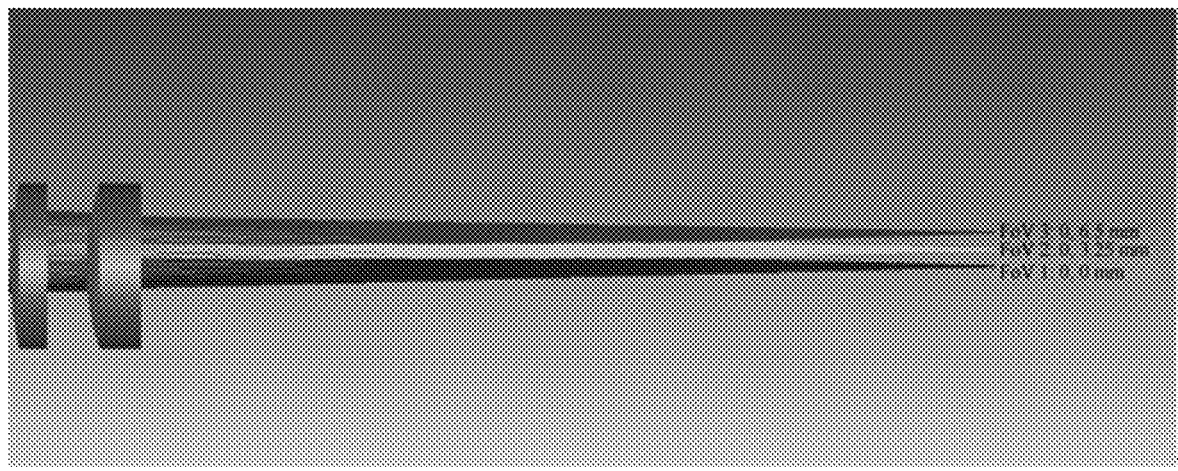
FIG. 29 is a schematic view showing the simulation results of the spot size of the imaging light beam when the imaging module according to an embodiment of the present application does not comprise a first splitter.
Figure 29:
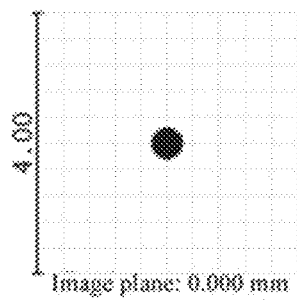
Figure 29:
Figure 29:
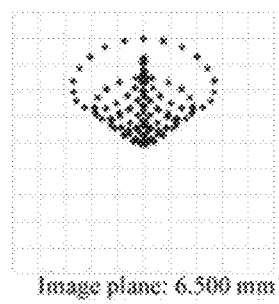
Figure 30:
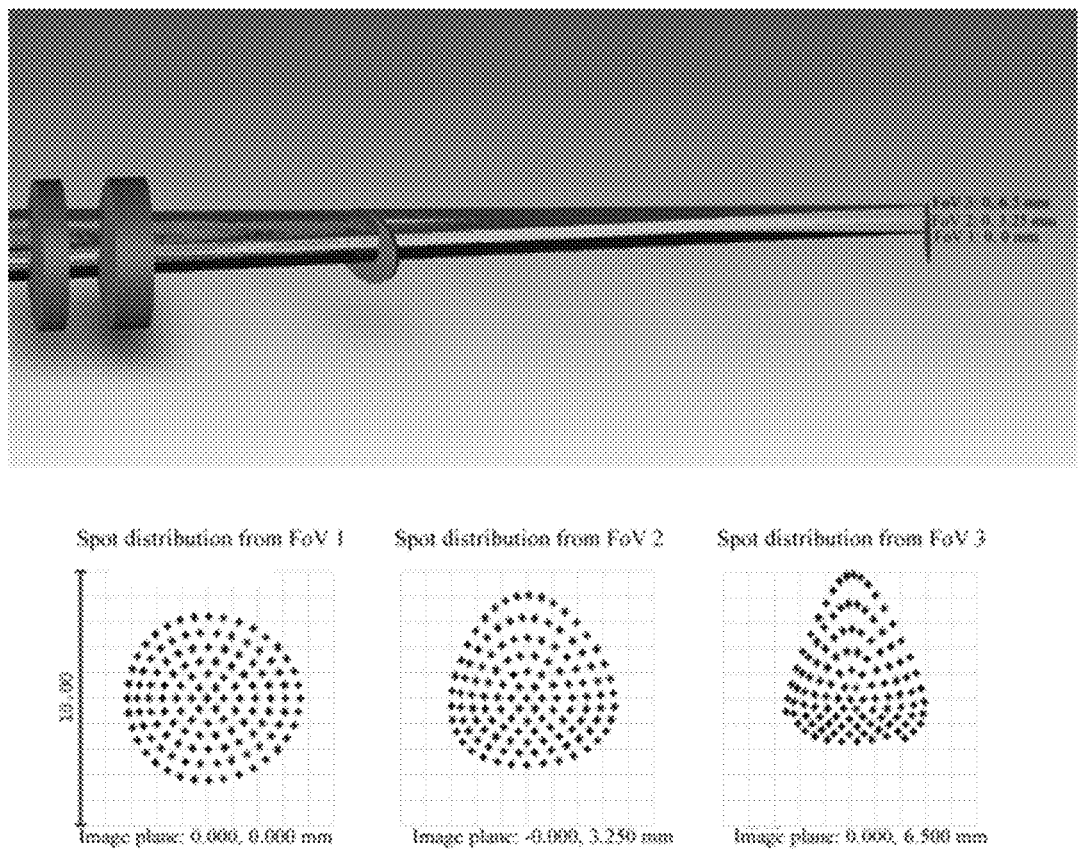
FIG. 30 is a schematic view showing the simulation results of the spot size of the imaging light beam when the imaging module according to an embodiment of the present application comprises a first splitter.

Specifically, in some examples, when imaging simulation is performed on the focused light beam of the second lens 18 by using software (e.g., Zemax), it is found that, the absence and the presence of the first splitter 14 after the second lens 18 (i.e., not performing light splitting and performing light splitting) will result in imaging simulation results shown in FIG. 29 and FIG. 30, respectively, and it can be seen that compared with a spot (a speckle) formed by a light beam after passing through the second lens 18 only, a spot (a speckle) formed by a light beam from the same FOV after passing through the second lens 18 and the first splitter 14 shows significantly increased astigmatism. For example, spots at coordinates (0, 0), (0, 3.250) and (0, 6.500) in FIG. 30 are larger than spots at corresponding coordinates in FIG. 29. By using root mean square radius (RMS radius), the size of a spot actually imaged by an imaging module can be quantitatively reflected. The RMS radius is an important radius parameter, and is a square root of the quadratic sum of the coordinates of the speckles (with reference to the center point) divided by the number of speckles. This radius reflects the size of a typical speckle, so as to quantitatively reflect the actual size of speckles of the system. In addition, GEO radius represents the diameter of a speckle. It is clear that, for the spots formed by the focusing of beams from the same FOV, FIG. 30 demonstrates a more significant dispersion with a larger RMS radius compared with FIG. 29.

Figure 31:
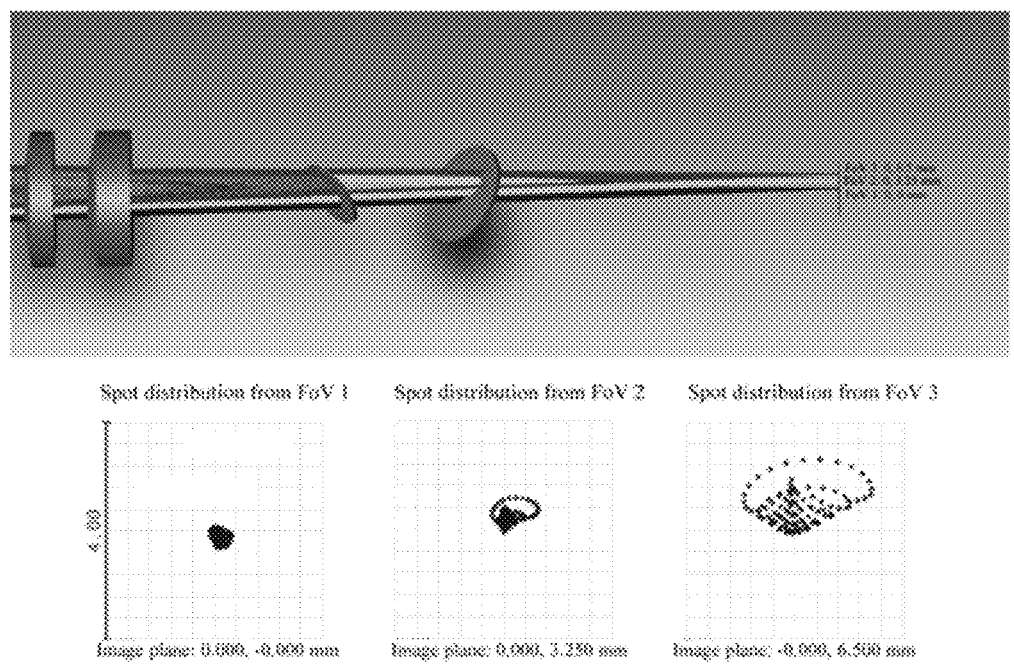
FIG. 31 is a schematic view showing the simulation results of the spot size of the imaging light beam when a compensation lens is introduced into the imaging module according to an embodiment of the present application.
Figure 31:
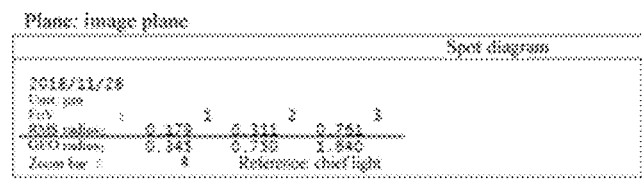

Based on this, in some examples, the applicant introduced a compensation lens 38 at any position between the second lens 18 and the first camera in the hope of compensating for astigmatism caused by imaging after transmission of a light beam. After the compensation lens 38 is introduced, referring to FIG. 31, for the spots formed by light beams from the same FOV, the spot size of FIG. 31 is significantly smaller than that of FIG. 30, and at the same coordinate, the spot size of FIG. 31 approaches or even is smaller than that of FIG. 29 in terms of the RMS radius.

Figure 32:
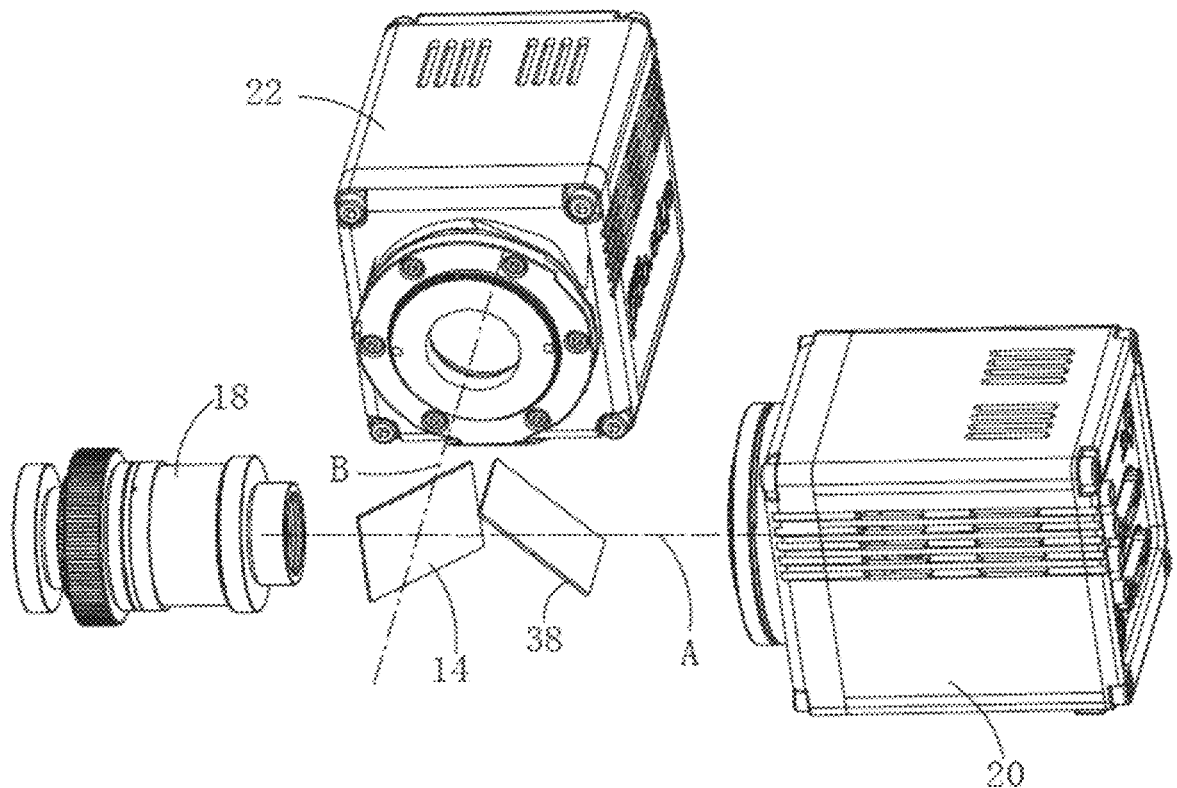
FIG. 32 is a partial three-dimensional perspective view of an imaging module according to an embodiment of the present application.
Figure 33:
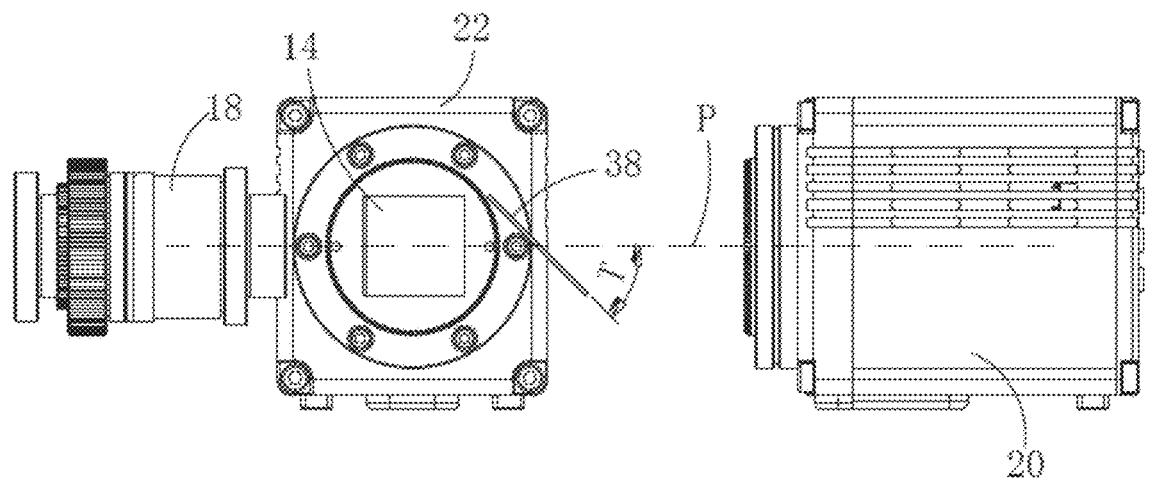
FIG. 33 is a front view of the imaging module of FIG. 32.
Figure 34:
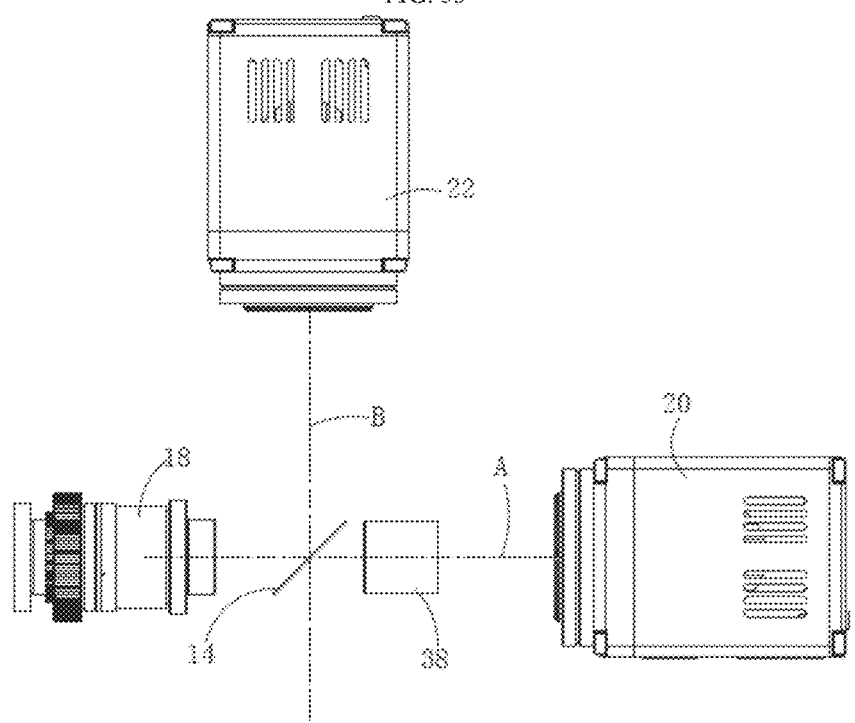
FIG. 34 is a top view of the imaging module of FIG. 32.

The compensation lens 38 may be a parallel plate or a dichroic mirror. In the embodiments of FIGS. 32-34, the compensation lens 38 is a dichroic mirror. The compensation lens 38 is at an included angle T of 45 degrees to a plane P perpendicular to the first splitter 14, and the plane P is defined by an optical axis A of the second light beam and an optical axis B of the third light beam.

Figure 35:
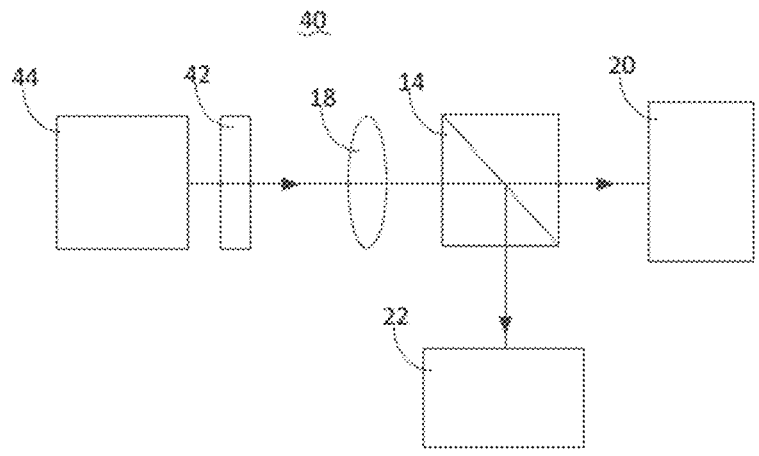
FIG. 35 is a structural schematic view of a light splitting module according to an embodiment of the present application during adjustment.

An embodiment of the present application further provides a method for calibrating an imaging module, wherein, referring to FIG. 35, an imaging module 10 comprises a light splitting module 40 comprising a second lens 18, a first splitter 14, a first camera 20 and a second camera 22, and the second lens 18, the first splitter 14 and the first camera 20 are sequentially arranged along an optical axis of the second lens 18, the method comprising: emitting a collimated light beam to the second lens 18 using a collimator 50 comprising a reticle 42, the reticle 42 comprising one or more patterns; converging the collimated light beam to the first splitter 14 through the second lens 18 and splitting the converged light beam into a second light beam and a third light beam through the first splitter 14; receiving, by the first camera 20, the second light beam to acquire a first image of the patterns; receiving, by the second camera 22, the third light beam to acquire a second image of the patterns; and adjusting an angle and/or position of the first camera 20 and/or the second camera 22 to align the contrasts of the first image and the second image.

According to the method for calibrating the imaging module, the light splitting module 40 is adjusted as a module independent from the whole imaging module 10, so that the space constraint on the adjustment of the whole imaging module can be relieved, and a plurality of cameras can be arranged perpendicularly to an optical axis simply and conveniently, thereby facilitating quick calibration of an imaging module comprising a splitting optical path.

Figure 36:
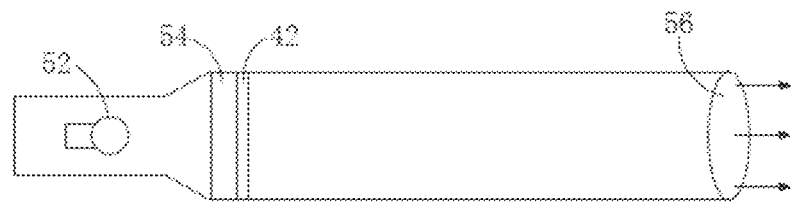
FIG. 36 is a structural schematic view of a collimator according to an embodiment of the present application.

Specifically, referring to FIG. 36, the collimator 50 further comprises a third light source 52, a ground glass 54 and an objective lens 56, the third light source 52, the ground glass 54, the reticle 42 and the objective lens 56 are sequentially arranged, and a light beam emitted by the third light source 52 sequentially passes through the ground glass 54, the reticle 42, and the objective lens 56 and is incident on the second lens 18. The collimated light beam emitted from the collimator 50 is a parallel light beam, and the parallel light beam passes through the second lens 18 and then is incident on the first splitter 14 and split into the second light beam and the third light beam.

The first image of the patterns of the reticle 42 acquired by the first camera 20 are consistent in contrast with the second image of the patterns of the reticle 42 acquired by the second camera 22, indicating that the plane of an image sensor of the first camera 20 is perpendicular to the optical axis of the second lens 18, and the plane of an image sensor of the second camera 22 is perpendicular to the optical axis of the splitting optical path.

Figure 37:
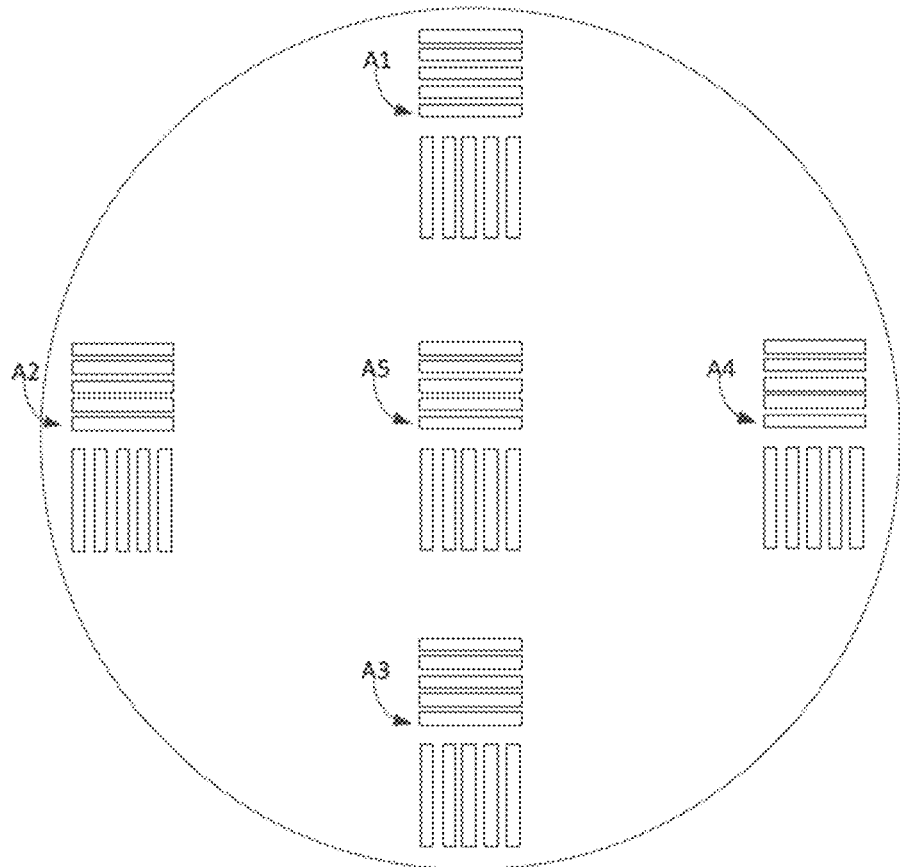
FIG. 37 is a schematic view showing patterns of a reticle with resolution line pairs according to an embodiment of the present application.

The reticle 42 is a customized reticle 42 with resolution line pairs designed by the applicant. Referring to FIG. 37, the reticle with resolution line pairs comprises 5 patterns A1-A5 distributed at different positions. When the contrasts are consistent for corresponding images of patterns A1-A5 of the reticle 42 acquired by the first camera 20 and the second camera 22, it is determined that the plane of the image sensor of the first camera 20 is perpendicular to the optical axis of the second lens 18, and the plane of the image sensor of the second camera 22 is perpendicular to the optical axis of the light beam reflected by the first splitter 14, which meets the requirements for image acquisition in sequence determination.

If MTF values (modulation transfer function values) of a plurality of images of the patterns are the same, it is determined that the contrasts of the images are the same. In some examples, if the difference of two or more MTF values is less than 10%, preferably less than 5%, the MTF values are determined to be the same. Specifically, in the first image and the second image, the MTF values of the images of the patterns A1-A5 are 0.80, 0.80, 0.80, 0.78, 0.80, 0.78, 0.80, 0.80, 0.80 and 0.80, respectively; therefore, the contrast of the first image and the contrast of the second image are determined to be consistent, and the imaging module 10 is calibrated. The closer the MTF value approaches 1, the better the performance of the imaging module 10.

The reticle 42 has a plurality of patterns, as shown in FIG. 37. The size of the first image or the second image is the size of a circle formed by images of the 5 patterns A1-A5. When the imaging module 10 is designed, it is required that the size of the first image and/or the second image is not less than forty percent of the size of an image actually required by the imaging module 10 for imaging. Thus, when imaging is performed by using the imaging module 10, images of high quality can be acquired, and the requirements for sequence determination are met.

Specifically, the size of the first image may refer to the size of an image formed by the distribution of images of a plurality of patterns on the first camera 20. The size of the second image may refer to the size of an image formed by the distribution of the images of a plurality of patterns on the second camera 22. Preferably, the size of the first image and/or the second image is not less than fifty percent of the size of an image actually acquired by imaging with the imaging module.

Figure 38:
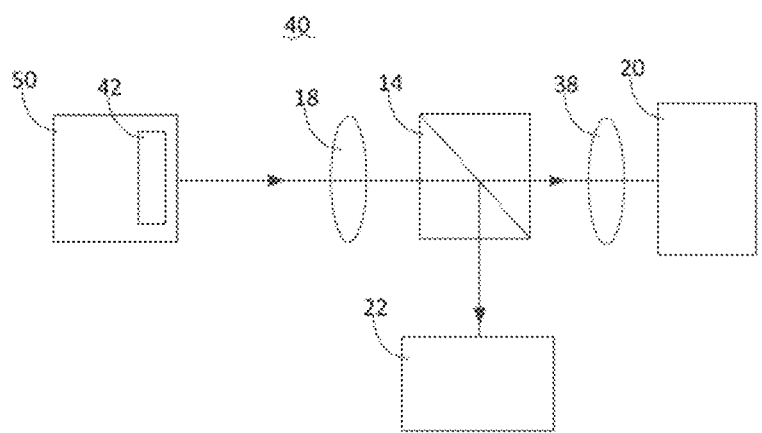
FIG. 38 is another structural schematic view of a light splitting module according to an embodiment of the present application during adjustment.

Referring to FIG. 38, the light splitting module 40 further comprises a compensation lens 38, wherein the compensation lens 38 is positioned between the first splitter 14 and the first camera 20, and the first camera 20 receives the second light beam passing through the compensation lens 38 to obtain the first image. Thus, the imaging of the first image shows good effect.

Figure 39:
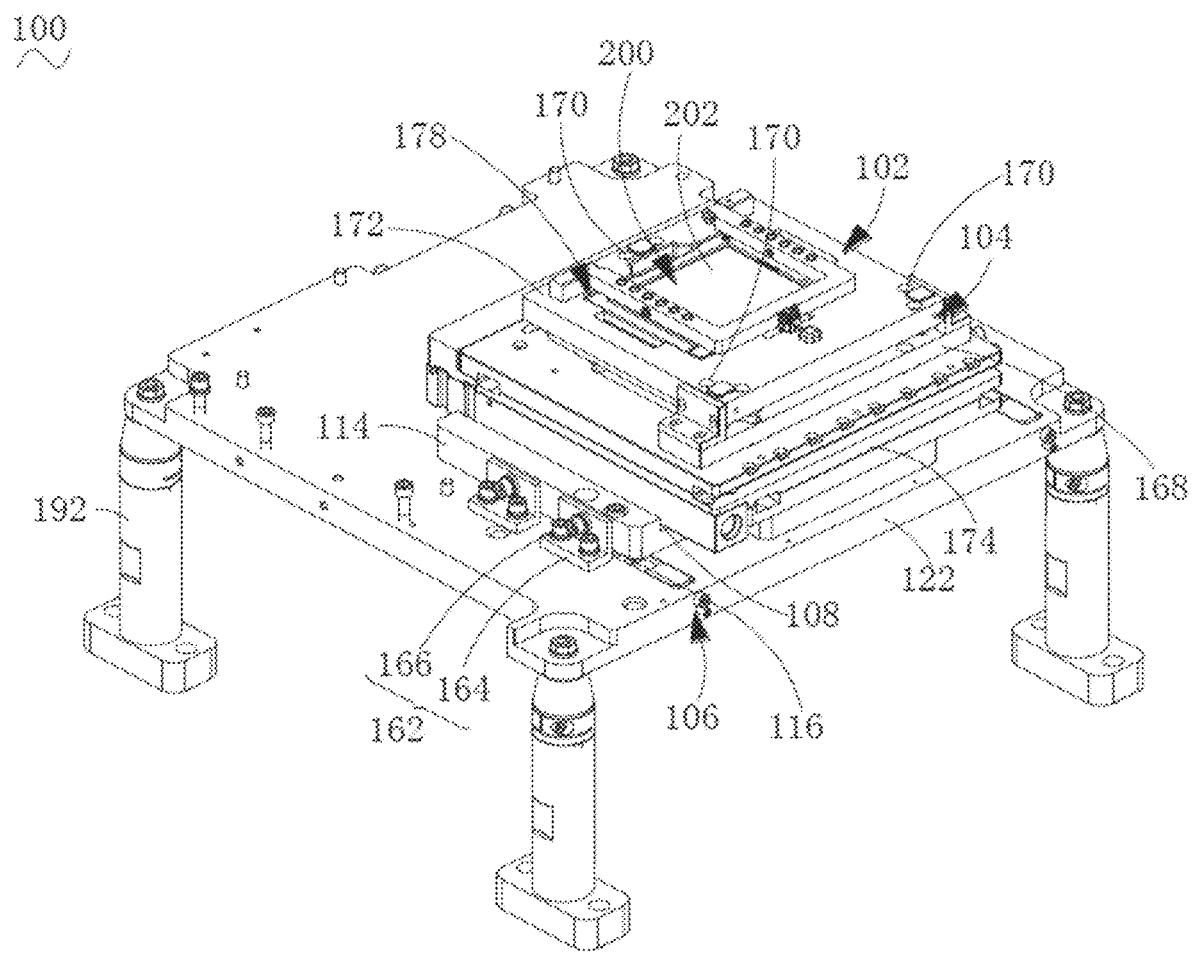
FIG. 39 is a three-dimensional perspective view of a carrier module according to an embodiment of the present application.
Figure 40:
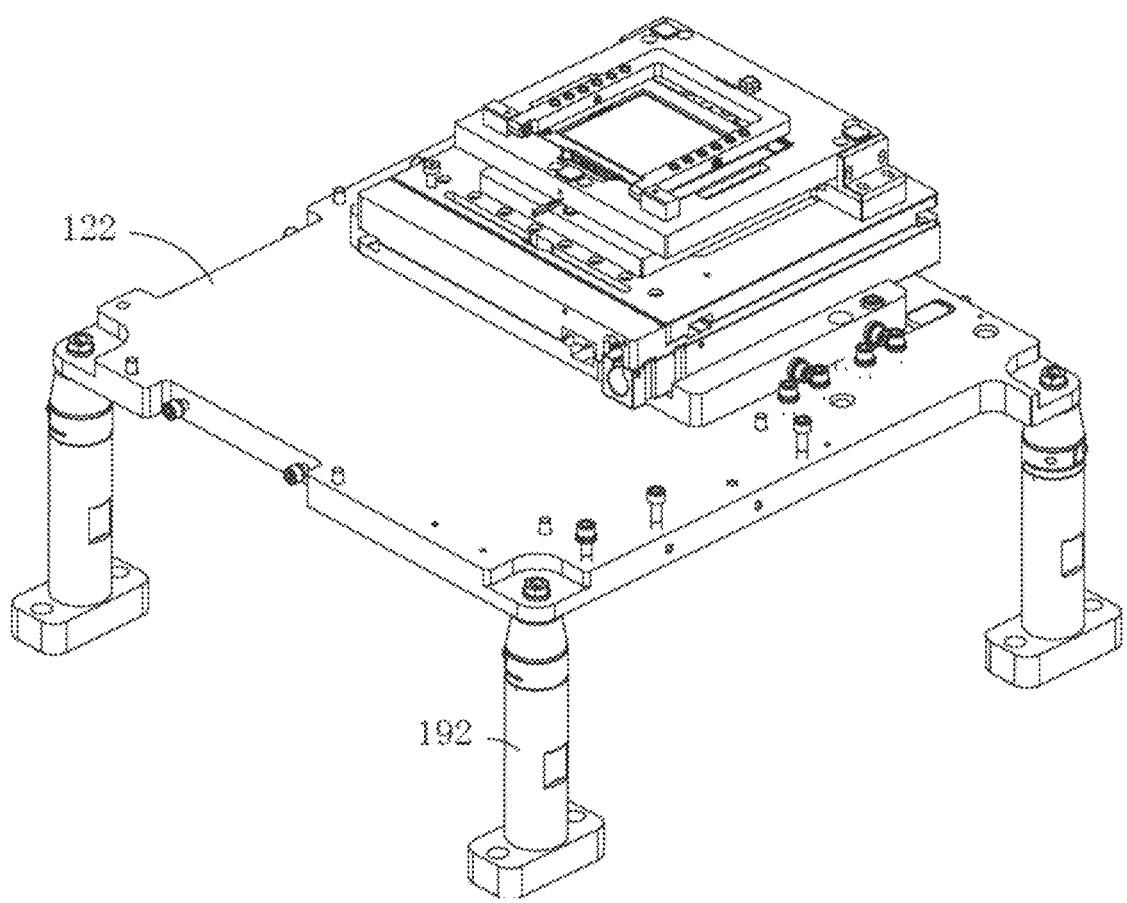
FIG. 40 is another three-dimensional perspective view of a carrier module according to an embodiment of the present application.

The position adjustment of the reaction device 200 by the carrier module 100:

Referring to FIGS. 39 and 40, a carrier module 100 according to an embodiment of the present application comprises a carrying module 102, a primary adjustment structure 104 and a secondary adjustment structure 106, wherein the carrying module 102 is provided on the primary adjustment structure 104, the primary adjustment structure 104 is provided on the secondary adjustment structure 106, the carrying module 102 is configured to carry a reaction device 200, the secondary adjustment structure 106 comprises a first plane 108, the secondary adjustment structure 106 is configured to adjust such that the first plane 108 and a preset axis satisfy a first preset positional relationship, and the primary adjustment structure 104 is configured to adjust such that a surface 202 of the reaction device 200 and the first plane 108 satisfy a second preset positional relationship.

The carrier module 100 above can adjust, by a two-stage adjustment structure, the plane 202 of the reaction device 200 to allow the plane to be in a preset positional relationship with a preset axis. Therefore, when other devices or assemblies are set based on the preset axis, the positional relationship between the plane 202 of the reaction device 200 and the other devices or assemblies can be adjusted to a desired one, thereby satisfying the requirements for sequencing, including optically detecting a specific position of the reaction device 200 during sequencing and optically detecting a plurality of specific positions of the reaction device 200 during a dynamic process.

Specifically, the preset axis may be a reference axis on a sequencing system 300. For example, referring to FIG. 6, the sequencing system 300 comprises an imaging module 10, the preset axis may be a lens optical axis OP of the imaging module 10, and the plane 202 of the reaction device 200 may be an upper surface of the reaction device 200. Generally, the imaging module 10 comprises a camera (not shown) and a microscope 112, the camera is located at an image side of lens of the microscope 112, and the reaction device 200 is located at an object side of lens of the microscope 112. When the upper surface of the reaction device 200 and the lens optical axis OP need to satisfy a perpendicular position relationship, the primary adjustment structure 104 with the reaction device 200 is detached from the secondary adjustment structure 106, the secondary adjustment structure 106 is adjusted so that the first plane 108 and the lens optical axis OP satisfy a perpendicular relationship, and then the primary adjustment structure 104 with the reaction device 200 is mounted on the secondary adjustment structure 106, and the primary adjustment structure 104 is adjusted so that the upper surface of the reaction device 200 and the first plane 108 satisfy a parallel relationship. As such, the upper surface of the reaction device 200 and the lens optical axis OP can satisfy a perpendicular relationship through the two-stage adjustment structure, and the reaction device 200 and the lens optical axis OP can still maintain a perpendicular relationship during a relative movement process of the two. Thus, in this example, the first preset positional relationship is a perpendicular relationship, and the second preset positional relationship is a parallel relationship. The reaction device 200 is, for example, a flowcell.

It would be appreciated that, in other examples, the first preset positional relationship and the second preset positional relationship may be different when the selected preset axis is different from the plane of the reaction device 200. For example, if the preset axis is an axis perpendicular to the lens optical axis OP, and the plane 108 of the reaction device 200 is the upper surface, the first preset relationship is a parallel relationship, and the second preset relationship is a parallel relationship, or if the preset axis is an axis inclining to the lens optical axis OP, and the plane 108 of the reaction device 200 is the upper surface, the first preset relationship is an inclining relationship, and the second preset relationship is a parallel relationship. For another example, if the preset axis is an axis perpendicular to the lens optical axis OP, and the plane 108 of the reaction device 200 is a side perpendicular to the upper surface of the reaction device 200, the first preset position is a parallel relationship, and the second preset relationship is a perpendicular relationship, or if the preset axis is an axis inclining to the lens optical axis OP, and the plane 108 of the reaction device 200 is a side perpendicular to the upper surface of the reaction device 200, the first preset relationship is an inclining relationship, and the second preset relationship is a perpendicular relationship and the like. In the above example, the positional relationship between the preset axis and the lens optical axis OP is generally constant. In other examples, the preset axis may be an axis parallel to the lens optical axis.

In summary, the first preset positional relationship is a perpendicular, parallel or inclining relationship, and/or the second preset positional relationship is a perpendicular, parallel or inclining relationship.

Figure 41:
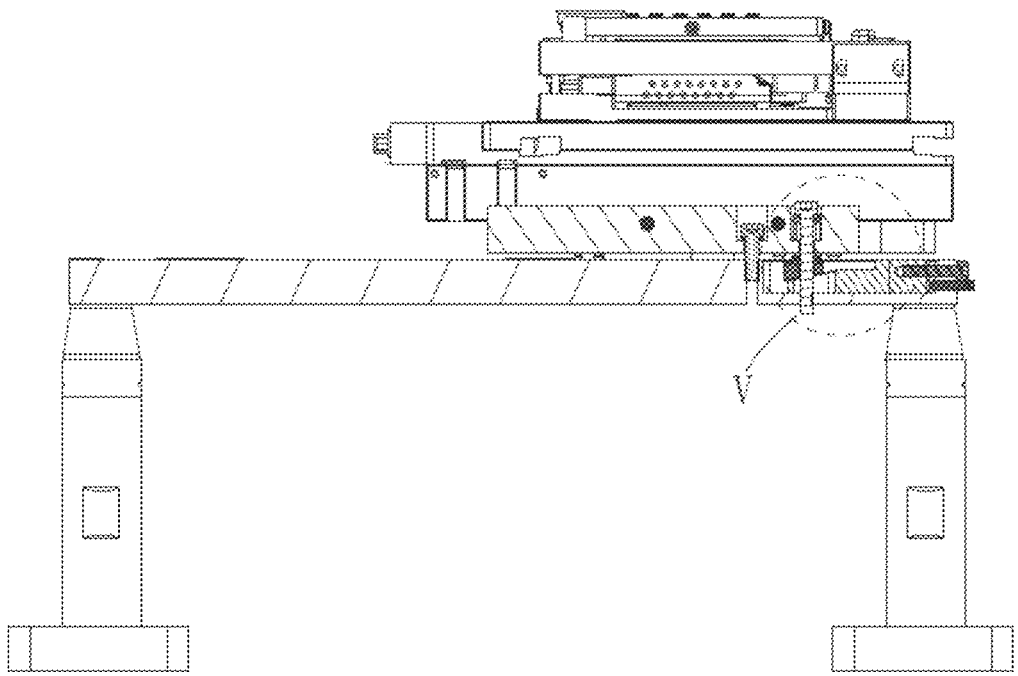
FIG. 41 is a cross-sectional schematic view of a carrier module according to an embodiment of the present application.

It should be noted that the inclining relationship refers to a non-perpendicular and non-parallel relationship. In addition, in other embodiments, the preset axis may be other axes irrelevant to the lens optical axis OP. In some embodiments, referring to FIG. 41 to FIG. 43, the secondary adjustment structure 106 comprises a first adjustment plate 114, a first adjustment member 116 and a supporting member 118, wherein the first adjustment plate 114 has a first plane 108, the supporting member 118 has a slope 120, the first adjustment plate 114 is disposed on the slope 120, and the first adjustment member 116 is connected to the supporting member 118 and is configured to drive the supporting member 118 to move so as to adjust the position of the first adjustment plate 114 on the slope 120. Thus, the position of the first adjustment plate 114 on the slope 120 is adjusted to make the first plane 108 and the preset axis satisfy the first preset positional relationship, and the adjustment method is simple and easy to implement. The first plane 108 may be an upper surface of the first adjustment plate 114.

Specifically, the secondary adjustment structure 106 comprises a substrate 122, a first adjustment member 116 and a supporting member 118 are disposed on the substrate 122, the first adjustment plate 114 is located on the substrate 122, and the first adjustment member 116 drives the supporting member 118 to adjust a pitch angle of the first plane 108 relative to the substrate 122.

In one example, the first adjustment member 116 is a screw, the first adjustment member 116 is in threaded connection with the supporting member 118, the substrate 122 is provided with a limiting slot 124, the supporting member 118 is provided in the limiting slot 124, and the limiting slot 124 is configured to limit the rotation of the supporting member 118 relative to the first adjustment member 116. When the first adjustment member 116 rotates, the supporting member 118 can only move linearly back and forth along the length direction of the first adjustment member 116 due to the limiting slot 124, so that the position of the first adjustment plate 114 on the slope 120 is adjusted.

In this embodiment, the secondary adjustment structure 106 comprises a cushion 126, a first elastic member 128, a connection screw 130 and a mating assembly 132, wherein the connection screw 130 comprises a head 134 and a post 136, the head 134 comprising a flange projecting from the post. The first adjustment plate 114 is provided with a first connecting through hole 138, and the first connecting through hole 138 is stepped. The connection screw 130 is inserted into the first connecting through hole 138, with the head 134 and a portion of the post 136 received in a larger section of the first connecting through hole 138 and another portion of the post 136 extending through a smaller section of the first connecting through hole 138 and connected to the substrate 122. The first elastic member 128 is received between the head 134 and a bottom surface of the larger section of the first connecting through hole 138, so that the substrate 122 can be elastically connected to the first adjustment plate 114.

Figure 42:
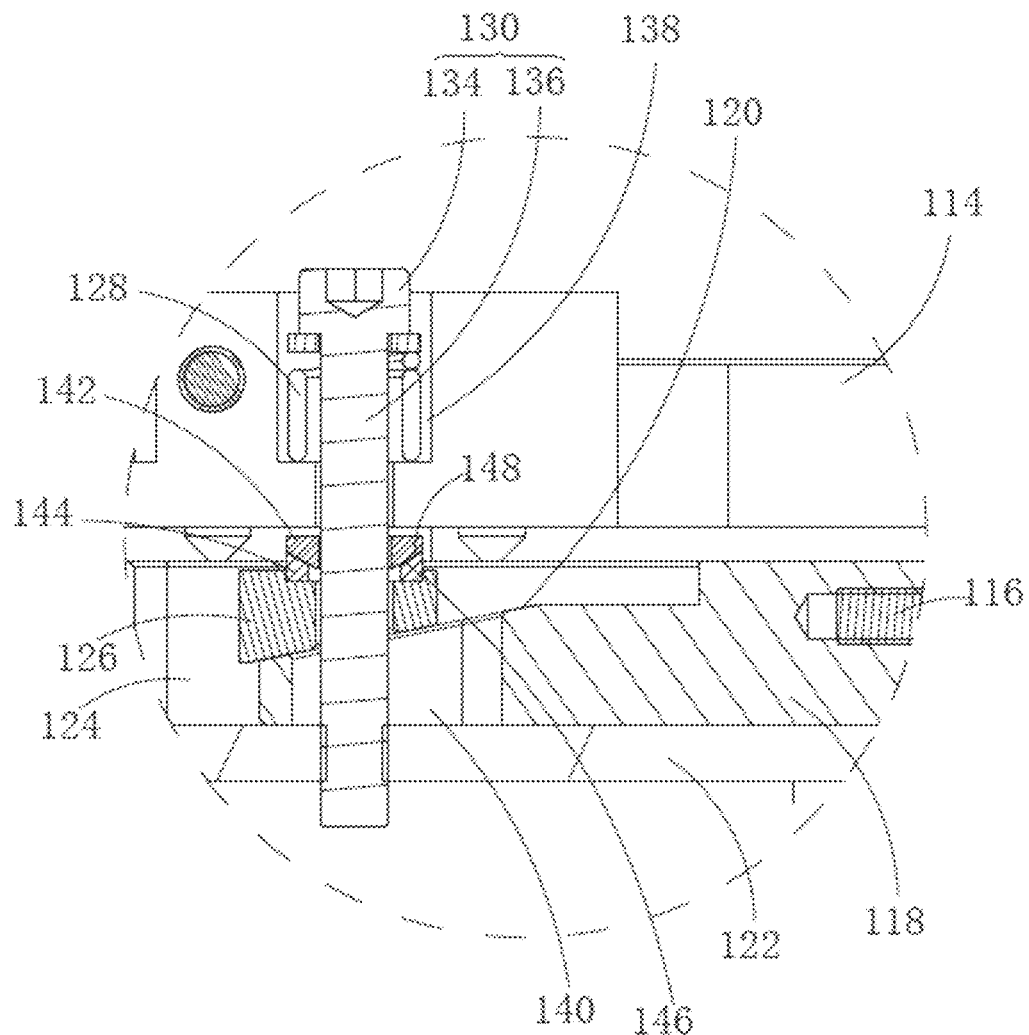
FIG. 42 is an enlarged schematic view of the portion V of the carrier module of FIG. 41.
Figure 43:
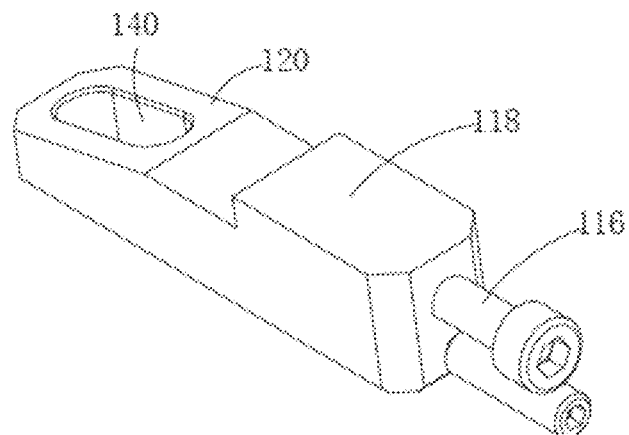
FIG. 43 is a schematic view of the connection between a supporting member and a first adjustment member according to an embodiment of the present application.

The cushion 126 is sandwiched between the mating assembly 132 and the slope 120. The supporting member 118 is provided with a through hole 140 passing through the slope 120 and penetrating through the supporting member, and the post 136 of the connection screw 130 is inserted into the through hole 140. Referring to FIG. 42, the space between the left and right sidewalls of the through hole 140 and the post 136 of the connection screw 130 is large enough so that the connection screw 130 does not obstruct the desired displacement of the supporting member 118 when moving back and forth along the axis of the first adjustment member 116.

In order to make the pitch angle of the first adjustment plate 114 smoother, the mating assembly 132 comprises a first mating member 142 and a second mating member 144, wherein the first mating member 142 is disposed on the bottom surface of the first adjustment plate 114, and the second mating member 144 is disposed in a recess on the top surface of the cushion 126. The first mating member 142 comprises a first mating surface 146 having a circular arc shape, the second mating member 144 comprises a second mating surface 148 having a circular arc shape, and the first mating surface 146 and the second mating surface 148 are rotatably connected.

In FIG. 39, the first adjustment plate 114 is provided, at both left and right sides thereof, with the first adjustment member 116, the supporting member 118, the cushion 126, the first elastic member 128, the connection screw 130 and the mating assembly 132, so as to achieve more accurate pitch adjustment. It would be appreciated that in other embodiments, it is possible that only one side of the first adjustment plate 114 is provided with the first adjustment member 116 and the supporting member 118. If elastic support and smoother angular adjustment are desired, the cushion 126, the first elastic member 128, the connection screw 130 and the mating assembly 132 can be added.

Figure 44:
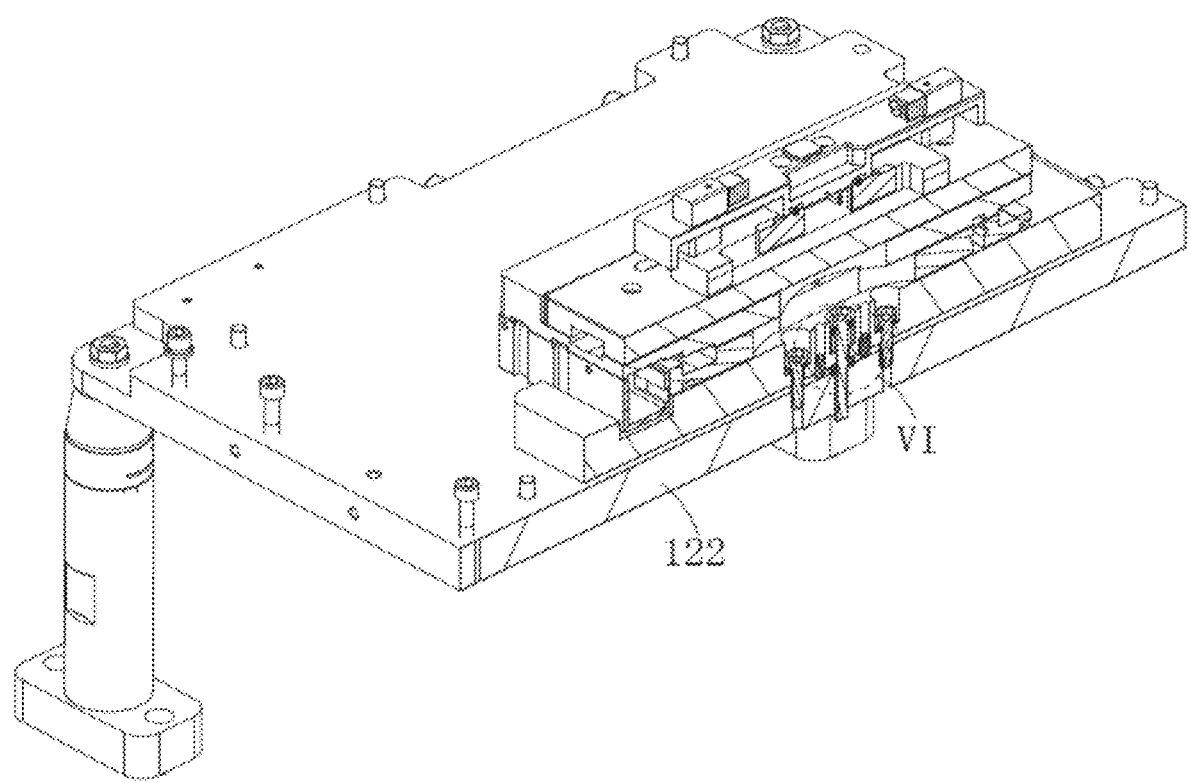
FIG. 44 is another cross-sectional schematic view of a carrier module according to an embodiment of the present application.
Figure 45:
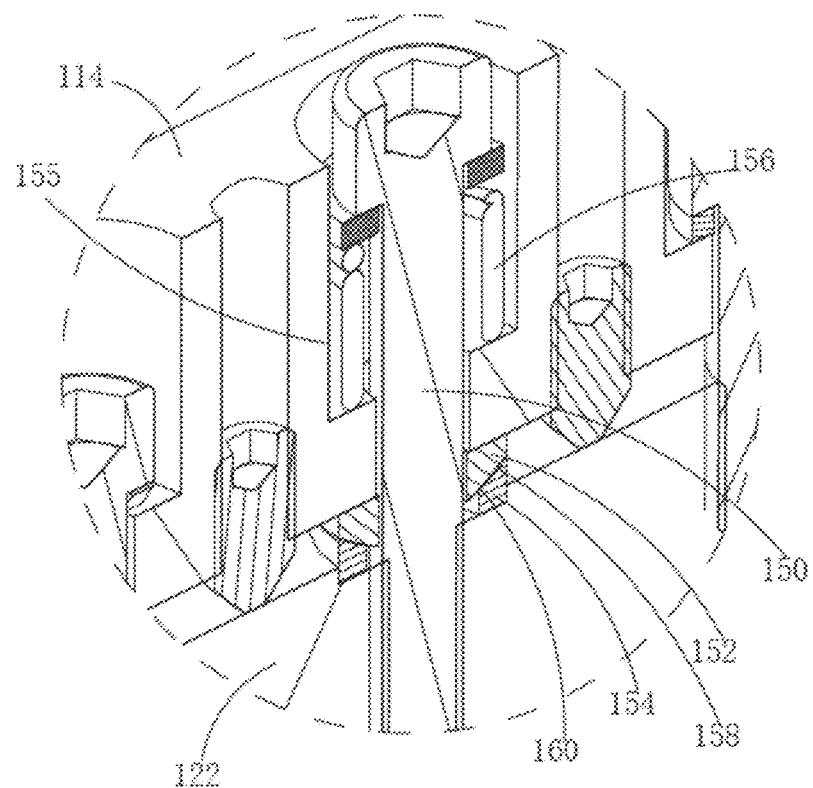
FIG. 45 is an enlarged schematic view of the portion VI of the carrier module of FIG. 44.

Further, referring to FIGS. 44 and 45, the secondary adjustment structure 106 comprises a connecting member 150, a third mating member 152 and a fourth mating member 154, wherein the connecting member 150 connects the first adjustment plate 114 and the substrate 122, the third mating member 152 and the fourth mating member 154 are rotatably connected relative to each other and are located between the first adjustment plate 114 and the substrate 122, the third mating member 152 is disposed on the first adjustment plate 114, and the fourth mating member 154 is disposed on the substrate 122.

Specifically, in FIG. 39, the first adjustment member 116 and the supporting member 118 are located at the left and/or right side of the first adjustment plate 114 closer to the front side of the carrier module 100, and the connecting member 150, the third mating member 152 and the fourth mating member 154 are located at the rear side of the first adjustment plate 114, thus obtaining an adjusting scheme that the pitch angle can be adjusted at the front side and the rear side serves as a rotation point.

The connecting member 150 may be a screw, and the first adjustment plate 114 is provided with a second connecting through hole 155, wherein the second connecting through hole 155 is stepped, and the connecting member 150 comprises a head and a post, the head comprising a flange protruding from the post. The connecting member 150 is inserted into the second connecting through hole 155, with the head and a portion of the post of the connecting member 150 received in a larger section of the second connecting through hole 155, and another portion of the post of the connecting member 150 extending through a smaller section of the second connecting through hole 155 and connected to the first adjustment plate 114. A second elastic member 156 is received between the head of the connecting member 150 and a bottom surface of the larger section of the second connecting through hole 155, so that the substrate 122 can be elastically connected to the first adjustment plate 114.

In order to make the pitch angle of the first adjustment plate 114 smoother, the third mating member 152 comprises a third mating surface 158 having a circular arc shape, the fourth mating member 154 comprises a fourth mating surface 160 having a circular arc shape, and the third mating surface 158 and the fourth mating surface 160 are rotatably connected.

In some embodiments, referring to FIG. 39, the secondary adjustment structure 106 comprises a fixation assembly 162, wherein the fixation assembly 162 is configured to fix the first adjustment plate 114. Thus, after the first adjustment plate 114 is adjusted, the fixation assembly 160 can be used to fix the position of the first adjustment plate 114, ensuring that the first plane 108 and the preset axis satisfy the first preset positional relationship.

Specifically, the fixation assembly 162 comprises a fixation plate 164 and a fixation member 166, wherein the fixation plate 164 is L-shaped, one side plate of the fixation plate 164 is connected to an upper surface of the substrate 122, and the other side plate is connected to the side of the first adjustment plate 114. The fixation member 166 fixedly connects the fixation plate 164 to the first adjustment plate 114 and the substrate 122. The fixation member 166 may be a screw.

In FIG. 39, left and right sides of the first adjustment plate 114 are each provided with the fixation assembly 162.

This secures the stability of the first adjustment plate 114.

In some embodiments, the primary adjustment structure 104 comprises a second adjustment plate 168 and a plurality of second adjustment members 170, wherein the carrying module 102 comprises a base 172 disposed on the second adjustment plate 168, the plurality of second adjustment members 170 are spaced apart and movably connected to the base 172 and the second adjustment plate 168, and the second adjustment members 170 are configured to adjust the second adjustment plate 168 when moved to allow the surface 202 of the reaction device 200 and the first plane 108 to satisfy a second preset positional relationship. Thus, the plane 202 of the reaction device 200 and the first plane 108 are allowed to satisfy the second preset positional relationship by multi-point adjustment.

Specifically, the carrying module 100 comprises a movable platform 174, wherein the movable platform 174 is disposed on the first adjustment plate 114, the primary adjustment structure 104 is disposed on the movable platform 172, and the movable platform 174 can drive the primary adjustment structure 104 and the reaction device 200 to move in a direction perpendicular to the lens optical axis OP.

Figure 46:
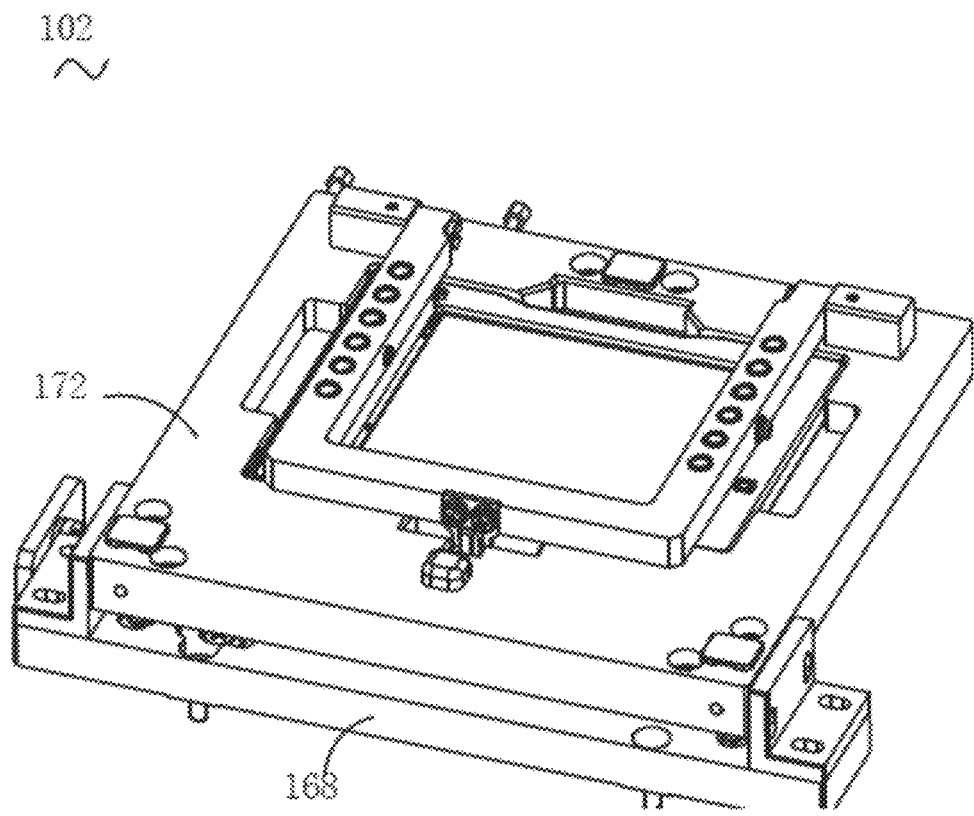
FIG. 46 is a schematic view of the connection between a primary adjustment structure and a carrying module according to an embodiment of the present application.
Figure 47:
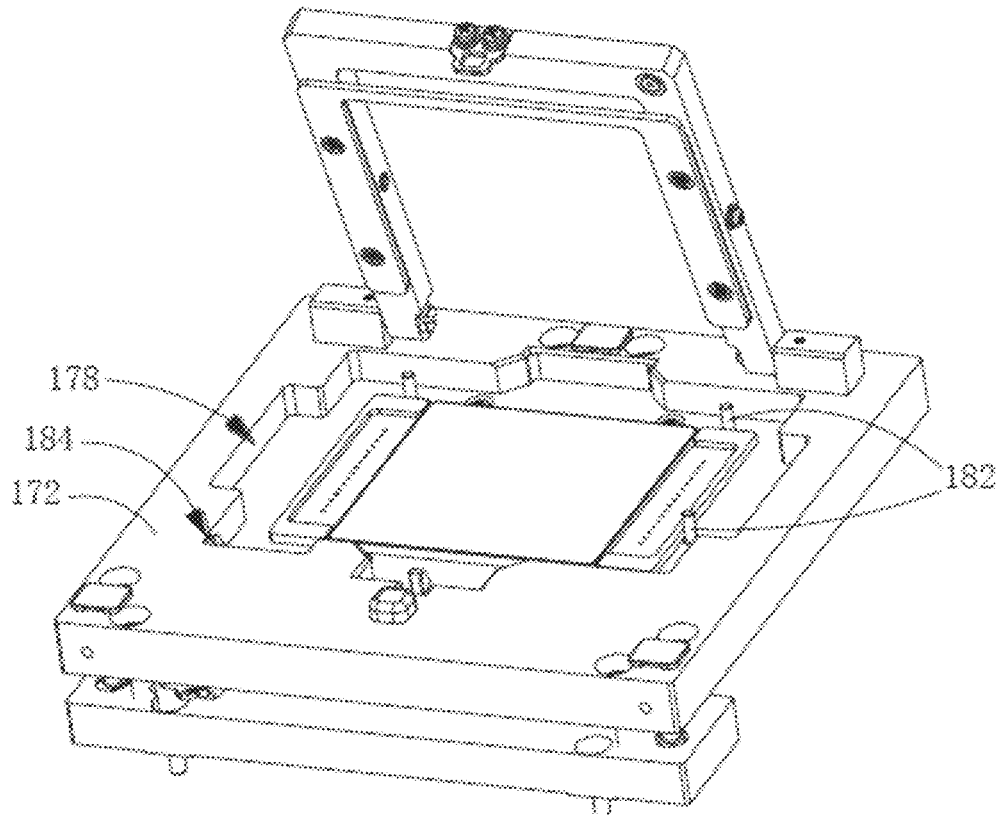
FIG. 47 is another schematic view of the connection between a primary adjustment structure and a carrying module according to an embodiment of the present application.
Figure 48:
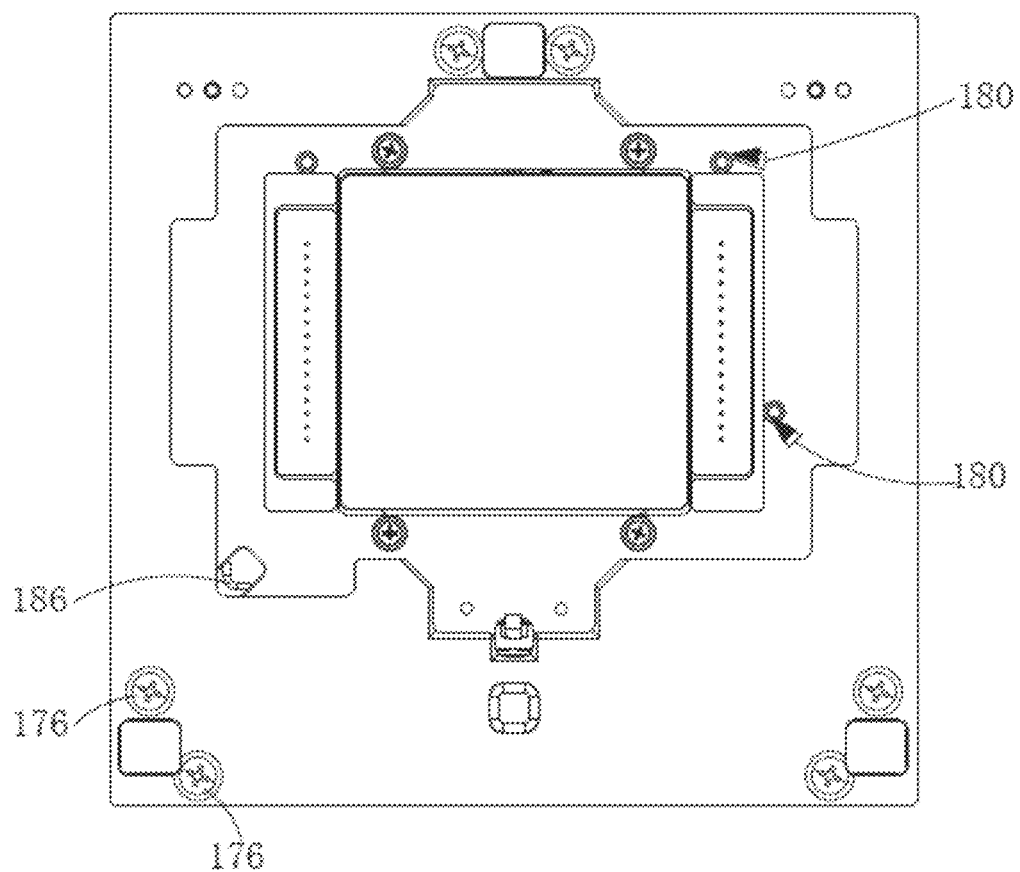
FIG. 48 is a schematic plan view of a primary adjustment structure and a carrying module according to an embodiment of the present application.

In this embodiment, referring to FIG. 46 to FIG. 48, the second adjustment member 170 comprises two adjustment screws 176, a third elastic member and a mating assembly. Reference can be made to the elastic connection between the substrate 122 and the first adjustment plate 114 for elastic connection between the second adjustment plate 168 and the base 172 by the adjustment screws 176 and the third elastic member, and reference can be made to the smoother adjustment of the first adjustment plate 114 described above for smoother adjustment of the base 172 by the mating assembly. Two adjustment screws 176 are located on an outer side of the mating assembly. The adjustment screws 176 connect the second adjustment plate 168 and the base 172, and the distance between the second adjustment plate 168 and the base 172 is adjusted by the adjustment screws 176. Specifically, for each second adjustment member 170, the distance between the second adjustment plate 168 and the base 172 is adjusted by screwing in and out the two adjusting screws 176, so that the plane 202 of the reaction device 200 and the first plane 108 can satisfy the second preset positional relationship by adjusting a plurality of second adjustment members 170.

In the example of FIG. 48, the number of the second adjustment members 170 is three, and the three second adjustment members 170 are distributed as an isosceles triangle.

Specifically, referring to FIG. 10, two second adjustment members 170 are disposed at left and right sides, respectively, of the second adjustment plate 168 closer to the front side of the carrier module 100, and another second adjustment member 170 is disposed at the rear side of the second adjustment plate. The connecting line of the two second adjustment members 170 is the base of the isosceles triangle, and the two connecting lines of the two second adjustment members 170 and the other second adjustment member 170 are the two sides of the isosceles triangle.

In some embodiments, the base 172 is provided with a receiving recess 178 thereon for receiving the reaction device 200, and the receiving recess 178 is provided with a positioning structure 180 for positioning the reaction device 200. Thus, by arranging the positioning structures 180 in the receiving recess 178, the positioning structure 180 can pre-position the reaction device 200 well when the reaction device 200 is received in the receiving recess 178, so as to ensure the establishment of a flow path.

Specifically, the positioning structure 180 comprises three positioning posts 182, and the three positioning posts 182 are distributed on two adjacent sides of the receiving recess 178. Thus, three-point positioning of the reaction device 200 can be achieved.

In FIG. 48, the planar shape of the receiving recess 178 is substantially square, two positioning posts 182 are located at the upper side of the receiving recess 178, and one positioning post 182 is located at the right side of the receiving recess 178. The two positioning posts 182 may be disposed in a direction parallel to the channel of the reaction device 200. The positioning posts 182 may be positioning pins.

In addition, the carrying module 102 comprises a side pushing mechanism 184 at the joint of the left side and lower side, and the side pushing mechanism 184 is telescopically disposed in the receiving recess 178 and is configured to ensure that the reaction device 200 is tightly attached to the positioning structure 180.

Thus, the side pushing mechanism 184 can be in cooperation with the waist hole of the reaction device 200, so that the reaction device 200 is prevented from being over-constrained in the receiving recess 178, and meanwhile, the side pushing mechanism 184 ensures that the reaction device 200 is tightly attached to the positioning structure 180, realizing positioning and fixing.

The side pushing mechanism 184 comprises a side pushing member 186 and a fourth elastic member (not shown), wherein the fourth elastic member is disposed in the base 172, and the side pushing member 186 is connected to the fourth elastic member and partially protrudes into the receiving recess 178, so that when the reaction device 200 is received in the receiving recess 178, the fourth elastic member can apply elastic force to the reaction device 200 through the side pushing member 186, allowing the reaction device 200 to be tightly attached to the positioning posts 182 on the upper side and the right side.

In addition, the sequencing system 300 comprises a reagent cartridge 188 for storing reagents, and a rotary valve, a three-way valve, a carrying module 102 and a power unit are provided in a flow direction of a liquid flowing from the reagent cartridge 188. The carrying module 102 receives the reaction device 200, and the channels of the reaction device 200 are connected to the flow paths of the sequencing system 300. By the rotary valve, different reagents can be introduced into the flow paths through the three-way valve to perform different reactions within the channels of the reaction device 200, including but not limited to extension, cleavage, capping, imaging, washing, and the like.

The power unit may be a pump to provide power for the liquid in the flow path. Referring to FIG. 40, the carrier module 100 is mounted to the sequencing system 300 via 4 supporting legs 192. In other embodiments, the three-way valve can be omitted in the sequencing system 300, and the rotary valve can directly introduce different reagents into the channels of the reaction device 200.

In the description of this specification, the description of the terms "one embodiment", "some embodiments", "schematic embodiments", "examples", "embodiments", "specific examples", "some examples" or the like, means that the particular features, structures, materials or characteristics comprised in the embodiments or examples are included in at least one embodiment or example of the present application. In this specification, the schematic description of the aforementioned terms do not necessarily refer to the same embodiment or example. Moreover, the particular features, structures, materials or characteristics described may be combined in any embodiment or example in any appropriate manner.

Logic and/or steps shown in the flowcharts or described herein in other manners, for example, may be considered as a program list of executable instructions that are used to implement logical functions, and may be specifically implemented on any computer-readable storage medium, for use by an instruction execution system, device, or apparatus (for example, a computer-based system, a system comprising a processor, or another system that can fetch instructions from the instruction execution system, device, or apparatus and execute the instructions), or for use in combination with the instruction execution system, device or apparatus. As used herein, the "computer-readable storage medium" may be any device that may comprise, store, communicate, propagate, or transmit a program for use by an instruction execution system, device, or apparatus, or for use in combination with the instruction execution system, device, or apparatus.

In addition, each functional unit in each embodiment of the present application may be integrated in one processing module, or each unit may physically exist alone, or two or more than two units may be integrated in one module. The above-mentioned integrated module may be implemented in the form of hardware or in the form of software functional module. The integrated module may also be stored in a computer-readable storage medium if it is implemented in the form of a software functional module and is sold or used as standalone products.

Although the embodiments of the present application have been shown and described above, it is to be understood that the aforementioned embodiments are exemplary and are not to be construed as limiting the present application, and that those of ordinary skill in the art may make changes, modifications, replacements and variations to such embodiments without departing from the scope of the present application.

What is claimed is:

1. A vibration damping structure for use in a detection system, wherein the vibration damping structure comprises a body and a support; the body is connected with the detection system through the support, and the body comprises an imaging module, an upper structure, a lower structure and an intermediate structure, wherein the imaging module is mounted on the upper structure, the lower structure carriers the upper structure through the intermediate structure, and a natural frequency of the body is greater than or equal to $\sqrt{2}$ times an internal excitation frequency.

2. The vibration damping structure according to claim 1, wherein the body comprises a carrier module for carrying and moving a reaction device, the carrier module being mounted on the lower structure and the reaction device being detachably mounted on the carrier module.

3. The vibration damping structure according to claim 1, wherein the intermediate structure comprises a first connecting member and a second connecting member, and the upper structure and the lower structure each have left and right sides, wherein the first connecting member and the second connecting member are a plate-shaped structure and a column-shaped structure, respectively;
one of the first connecting member and the second connecting member connects the left side of the lower structure and the left side of the upper structure, and the other connects the right side of the lower structure and the right side of the upper structure.

4. The vibration damping structure according to claim 1, wherein the intermediate structure comprises a first connecting member and a second connecting member, and the upper structure and the lower structure each have left and right sides, wherein the first connecting member and the second connecting member are both plate-shaped structures;
one of the first connecting member and the second connecting member connects the left side of the lower structure and the left side of the upper structure, and the other connects the right side of the lower structure and the right side of the upper structure.

5. The vibration damping structure according to claim 4, wherein the intermediate structure comprises a third connecting member, wherein the third connecting member is a plate-shaped structure, the upper structure and the lower structure each have a rear side, and the third connecting member connects the rear side of the lower structure and the rear side of the upper structure.

6. The vibration damping structure according to claim 5, wherein the first connecting member, the second connecting member and the third connecting member are each a part of an integrated structure.

7. The vibration damping structure according to claim 4, wherein the body has a center line, and the first connecting member and the second connecting member are symmetrically arranged along the center line.

8. The vibration damping structure according to claim 4, wherein the vibration damping structure comprises a reinforcing member capable of reinforcing the strength of the body, wherein the reinforcing member connects the first connecting member and the lower structure, and/or the reinforcing member connects the first connecting member and the second connecting member.

9. The vibration damping structure according to claim 8, wherein the reinforcing member connects an outer side of the first connecting member and an upper side of the lower structure.

10. The vibration damping structure according to claim 8, wherein the reinforcing member connects an inner side of the first connecting member, a lower side of the upper structure and an inner side of the second connecting member.

11. The vibration damping structure according to claim 1, wherein the support comprises vibration damping members and supporting legs, the detection system comprises a substrate, the body is mounted on the vibration damping members, and the vibration damping members are mounted on the substrate through the supporting legs.

12. The vibration damping structure according to claim 11, wherein a principal axis of the vibration damping member is parallel to an optical axis of the imaging module.

13. The vibration damping structure according to claim 1, wherein the upper structure comprises an upper plate, the lower structure comprises a lower plate, and the density of a material of the lower plate or the density of a material of the intermediate structure is greater than that of the upper plate.

14. The vibration damping structure according to claim 13, wherein the lower plate is heavier than the upper plate.

15. The vibration damping structure according to claim 1, wherein the natural frequency of the vibration damping structure is not equal to the external excitation frequency.

16. A detection system, comprising the vibration damping structure according to claim 1.

17. A sequencing system, comprising the vibration damping structure according to claim 1.

18. The sequencing system according to claim 17, wherein the imaging module comprises a first light source, a first lens, and a light splitting module comprising a first splitter, a second lens, a first camera and a second camera, wherein
   the first lens is configured to receive a first light beam from the first light source and allow the first light beam to be incident on a sample after being collimated, and to receive a light beam from the sample and collimate the light beam;
   the second lens is configured to converge the collimated light beam from the first lens;
   the first splitter is configured to split the converged light beam from the second lens into a second light beam and a third light beam;
   the first camera is configured to receive the second light beam;
   the second camera is configured to receive the third light beam.

19. The sequencing system according to claim 18, wherein the imaging module comprises a second splitter configured to receive the first light beam from the first light source and to divert the first light beam to the first lens.

20. The sequencing system according to claim 17, wherein the body comprises a carrier module comprising a carrying module, a primary adjustment structure and a secondary adjustment structure, wherein the carrying module is provided on the primary adjustment structure, the primary adjustment structure is provided on the secondary adjustment structure, the carrying module is configured to carry the reaction device, the secondary adjustment structure comprises a first plane, the secondary adjustment structure is configured to adjust such that the first plane and a preset axis satisfy a first preset positional relationship, and the primary adjustment structure is configured to adjust such that a surface of the reaction device and the first plane satisfy a second preset positional relationship.

* * * * *